United States Patent
Goto et al.

(10) Patent No.: US 9,406,910 B2
(45) Date of Patent: Aug. 2, 2016

(54) ORGANIC ELECTROLUMINESCENT ELEMENT AND MANUFACTURING METHOD THEREOF, AND PHOSPHORUS-CONTAINING ORGANIC COMPOUND AND MANUFACTURING METHOD THEREOF

(71) Applicants: Kyushu Electric Power Co., Inc., Fukuoka (JP); Daiden Co., Ltd, Fukuoka (JP)

(72) Inventors: Yasuyuki Goto, Fukuoka (JP); Mitsuharu Noto, Fukuoka (JP); Tsuyoshi Hayashida, Fukuoda (JP); Masanao Era, Saga (JP)

(73) Assignees: Daiden Co., Ltd, Fukuoka (JP); Kyushu Electric Power Co., Inc., Fukuoka (JP)

( * ) Notice: Subject to any disclaimer, the term of this patent is extended or adjusted under 35 U.S.C. 154(b) by 511 days.

(21) Appl. No.: 13/895,180

(22) Filed: May 15, 2013

(65) Prior Publication Data

US 2013/0295706 A1   Nov. 7, 2013

Related U.S. Application Data

(62) Division of application No. 10/599,334, filed as application No. PCT/JP2005/007551 on Apr. 20, 2005, now abandoned.

(30) Foreign Application Priority Data

Apr. 20, 2004   (JP) .................................. 2004-124712

(51) Int. Cl.
| | |
|---|---|
| *H01L 51/54* | (2006.01) |
| *H01L 51/56* | (2006.01) |
| *C07F 9/53* | (2006.01) |
| *H01L 51/00* | (2006.01) |
| *H01L 51/50* | (2006.01) |

(52) U.S. Cl.
CPC .............. *H01L 51/56* (2013.01); *C07F 9/5329* (2013.01); *H01L 51/005* (2013.01); *H01L 51/0058* (2013.01); *H01L 51/0007* (2013.01); *H01L 51/0037* (2013.01); *H01L 51/0039* (2013.01); *H01L 51/0042* (2013.01); *H01L 51/0085* (2013.01); *H01L 51/5012* (2013.01); *H01L 51/5048* (2013.01)

(58) Field of Classification Search
None
See application file for complete search history.

(56) References Cited

U.S. PATENT DOCUMENTS

| | | | |
|---|---|---|---|
| 3,895,074 A | | 7/1975 | Mrowca |
| 5,231,329 A | | 7/1993 | Nishikitani et al. |
| 5,389,444 A | * | 2/1995 | Hosokawa ............. C09K 11/06 252/301.16 |
| 5,811,834 A | * | 9/1998 | Tamano ................ C07C 211/50 257/103 |
| 7,033,680 B2 | | 4/2006 | Tanaka et al. |
| 2001/0012572 A1 | | 8/2001 | Araki |
| 2005/0106413 A1 | * | 5/2005 | Tanaka ................... C08G 61/12 428/690 |

FOREIGN PATENT DOCUMENTS

| | | |
|---|---|---|
| JP | 200263989 | 2/2002 |
| JP | 2002367785 | 12/2002 |
| JP | 2003317965 | 11/2003 |
| JP | 2003535869 | 12/2003 |
| JP | 2004095221 | 3/2004 |
| JP | 2004204140 | 7/2004 |
| WO | 0194359 | 12/2001 |
| WO | 0240491 | 5/2002 |
| WO | 03048173 | 6/2003 |
| WO | WO 03/046108 A1 * | 6/2003 |
| WO | 2004003110 | 4/2004 |

OTHER PUBLICATIONS

Machine translation of JP2003-317965. Date of publication: Nov. 7, 2003.*
Baldwin, Roger A., et al., Arylenebis (tertiary phosphines) and—(phosphinic acids), The Journal of Organic Chemistry, May 1967, 32 (5), 1572-1577.
Baldwin, Roger AL., et al., Organometallic Azides. I. Preparation and Reactions of Diarylphosphinic Azides, The Journal of Organic Chemistry, Nov. 1965, 30 (11), 3860-3866.
Chemical Abstract, 72:30819 (Entered STN: May 12, 1984).
Chemical Abstract, 67:3123 (Entered STN: May 12, 1984).
Polyhedron; 199; 18(16); pp. 2117-2127.
Chemische Berichte/Recueil; 1997; 130(2); pp. 299-305.
Canadian Journal of Chemistry; 1969; 47(24); pp. 4679-4684.

* cited by examiner

*Primary Examiner* — Andrew K Bohaty
(74) *Attorney, Agent, or Firm* — Stites & Harbison PLLC; Richard S. Myers, Jr.

(57) ABSTRACT

An organic electroluminescent element comprising an anode, a cathode and a plurality of organic compound layers sandwiched between the anode and cathode, the organic compound layers including: a hole-transporting layer made of an organic compound insoluble in alcohols; and an electron-transporting layer formed on the hole-transporting layer by a wet method, the electron-transporting layer being made of a phosphorus-containing organic compound soluble in the alcohols.

9 Claims, 6 Drawing Sheets

[Example 1]

[Comparative Example 1]

[Example 2]

[Comparative Example 2]

ORGANIC ELECTROLUMINESCENT ELEMENT AND MANUFACTURING METHOD THEREOF, AND PHOSPHORUS-CONTAINING ORGANIC COMPOUND AND MANUFACTURING METHOD THEREOF

RELATED APPLICATIONS

This is divisional patent application claiming priority to U.S. patent application Ser. No. 10/599,344, filed Jun. 28, 2007, which is a National Stage Entry of International Patent Application No. PCT/JP05/07551, filed Apr. 20, 2005, which claims priority to Japanese Patent Application No. 2004-124712, filed Apr. 20, 2004, the entire disclosures of which are incorporated herein by this reference.

TECHNICAL FIELD

The present invention relates to an organic electroluminescent element and a manufacturing method thereof, and a novel phosphorus-containing organic compound used for the formation of an electron-transporting layer of the organic electroluminescent element and a manufacturing method thereof. According to the present invention, it is possible to form the electron-transporting layer of the organic electroluminescent element on an underlying organic film by a wet method without damaging the underlying organic film.

BACKGROUND ART

Organic electroluminescent elements that use an organic material as a luminescent material act to recombine holes injected from their anodes and electrons injected from their cathodes and to form excited molecules (excitons), which radiate energy to emit light when returning to a ground state.

In 1987, C. W. Tang et al. of the Eastman Kodak Company announced an organic electroluminescent element having organic films laminated between its anode and cathode, and thus realized emission of high luminance light at a low driving voltage (C. W. Tang et al., Applied Physics Letters, 1987, Vol. 51, p. 913: Nonpatent document 1).

Since the announcement by Tang et al., eager studies have been conducted of organic electroluminescent elements, that is, of their luminescence in three RGB primary colors, luminance improvement, stability, laminate structure and manufacturing method. The organic electroluminescent elements have already been in some practical use as a component of a display for the mobile telephone or car audio, and are regarded as promising as a component of a next-generation flat display which is an alternative to the liquid crystal display.

Many organic electroluminescent elements use an electron-transporting material in combination with a luminescent material.

The electron-transporting material is used for efficient transportation of electrons injected from the cathode to a luminescent layer and also for blocking of holes. Usable electron-transporting materials include an oxadiazole derivative and Alq$_3$ (tris(8-hydroxyquinoline)aluminum), which is widely used as a green-color luminescent material.

Methods for forming an organic film for an organic electroluminescent element are roughly classified into two categories: dry methods and wet methods. The dry methods include a vacuum deposition method and a CVD method, while the wet methods include a spin coating method and an inkjet method.

The dry methods have an advantage of facilitating formation of a multi-layered film due to vacuum deposition. When used for the manufacture of organic electroluminescent elements, the dry methods facilitate formation of a multi-layered film comprising a hole-injecting layer, an electron-injecting layer, a hole-blocking layer and the like, to achieve an injection balance between holes and electrons. Thus, organic electroluminescent elements manufactured by the dry methods realize high efficiency and luminance, and display devices using such organic electroluminescent elements have already been in practical use. The thy methods, however, have a disadvantage of requiring large-scale apparatuses for the manufacture of elements having a large area, which lowers the productivity.

On the other hand, the wet methods have an advantage of permitting formation of a coating film having a large area, all at a time, which facilitates the manufacture of elements having a large area and increases the productivity. In terms of productivity and costs, therefore, the wet methods are superior to the dry methods. Especially for polymer materials, with which it is often difficult to form a thin film by vacuum deposition, the wet methods are mainly employed.

Japanese Unexamined Patent Publication No. 2002-63989 (Patent document 1) discloses a luminescent element containing an organic fluophor represented by the formula:

$R_3P=O$ wherein R, the same or different from each other, are substituents such as an aryl group, at least one of R being a fluorescent skeleton.

Also, Japanese Unexamined Patent Publication No. 2004-204140 (Patent document 2) discloses a material for luminescent element represented by the formula:

$(Ar)_3P=O$ wherein Ar, the same or different from each other, are an aryl group or a heteroaryl group, at least one of Ar being a naphthyl group linked at its α position, at least one of Ar containing either a fluorescent skeleton or a charge transport skeleton.

The above publication recites condensed rings such as phenanthryl, anthranyl, pyrenyl and perylenyl, as examples of fluorescent skeletons.

The structure of the phosphorus-containing organic compound of the present invention, however, is different from, though similar to, the structures of the organic fluophor and the material for luminescent element disclosed in the above publications, since it does not have a naphthyl group linked at its α position, a fluorescent skeleton or the like.

Patent document 1: Japanese Unexamined Patent Publication No. 2002-63989
Patent document 2: Japanese Unexamined Patent Publication No. 2004-204140
Nonpatent document 1: C. W. Tang et al., Applied Physics Letters, 1987,

DISCLOSURE OF THE INVENTION

Problem that the Invention is to Solve

However, conventional electron-transporting materials have the following problem when they are used for the manufacture of an organic film by a wet method.

With the wet methods that use a solution of an electron-transporting material in a solvent for film formation, the conventional electron-transporting materials permit the use of only limited solvents such as chloroform, toluene, THF (tetrahydrofuran) and the like. When a solvent other than the above is used, the electron-transporting material does not dissolve at all and a film itself cannot be formed or, even if it is formed, the electron-transporting material crystallizes after the film formation and the product obtained is not usable as an element.

Accordingly, if the electron-transporting layer is formed by the wet method on an underlying organic film which is soluble in chloroform, toluene, THF and the like, the underlying organic film dissolves in, and is damaged by, the same solvent that is used for the formation of the electron-transporting layer, and as a result, the organic film has an ununiform quality and pin-holes, making it impossible to manufacture an excellent organic electroluminescent element.

Since especially polymer materials used for the film formation by the wet method are soluble in only solvents such as chloroform, toluene, THF (tetrahydrofuran) and the like, it is impossible to form the electron-transporting layer on a film of a polymer material by the wet method.

Object of the Invention

It is an object of the present invention to provide a phosphorus-containing organic compound that can be used for formation of a smooth-surfaced electron-transporting layer of an organic electroluminescent element on an underlying organic film by a wet method without damaging the underlying organic film.

Means of Solving the Problem

The present inventors, as a result of eager studies to achieve the above object, have noted that, by using a specific phosphorus-containing organic compound as an electron-transporting material for an organic electroluminescent element, it is possible to form an electron-transporting layer on an underlying organic film by a wet method without damaging the underlying organic film, thereby completing the present invention.

In one aspect, the present invention provides an organic electroluminescent element comprising an anode, a cathode and a plurality of organic compound layers sandwiched between the anode and cathode, the organic compound layers including: a hole-transporting layer made of an organic compound insoluble in alcohols; and an electron-transporting layer formed on the hole-transporting layer by a wet method, the electron-transporting layer being made of a phosphorus-containing organic compound soluble in the alcohols.

In another aspect, the present invention provides a manufacturing method of an organic electroluminescent element including an anode, a cathode and a plurality of organic compound layers sandwiched between the anode and cathode, the method comprising the steps of forming a hole-transporting layer using an organic compound insoluble in alcohols; and forming an electron-transporting layer on the hole-transporting layer by a wet method using as an electron transporting layer material a phosphorus-containing organic compound to be dissolved in an alcohol.

In still another aspect, the present invention provides a phosphorus-containing organic compound as a condensation product of a compound represented by the general formula (4):

wherein $Ar^{11}$, the same or different from each other, represent a phenyl group or naphthyl group optionally substituted with a halogen atom, a lower alkyl group, a lower alkoxy group or a phenyl group, and either a compound represented by the formula:

$$Ar^{12}I$$

wherein $Ar^{12}$ represents benzene substituted with three halogen atoms, or benzene or biphenyl substituted with two halogen atoms or a compound represented by the general formula (5):

wherein $Ar^{13}$, the same or different from each other, are a phenyl group or biphenyl group optionally substituted with a halogen atom, at least two of $Ar^{13}$ being a phenyl group or biphenyl group substituted with at least one halogen atom.

In yet another aspect, the present invention provides a phosphorus-containing organic compound having at least three partial structures represented by a diarylphosphine oxide skeleton, the diarylphosphine oxide skeleton represented by either the formula (9):

wherein $Ar^{11}$ has the same meaning as defined in the general formula (4) or the formula (10):

wherein $Ar^{13'}$, the same or different from each other, are a phenyl group or a biphenyl group, or a phenylene group or biphenylene group linked to the formula (9).

In a further aspect, the present invention provides a manufacturing method of a phosphorus-containing organic compound, comprising the step of condensing, in a solvent, in the presence of a condensing catalyst and a base, a compound of the general formula (4) with either a compound of the formula: ArI or a compound of the general formula (5).

Effect of the Invention

According to the present invention, the organic electroluminescent element is manufactured by forming the electron-transporting layer on the hole-transporting layer of the organic compound insoluble in the alcohols, by the wet method, using the solution of the electron-transporting material in the alcohol. Since the underlying hole-transporting layer does not dissolve in the alcohol used for formation of the overlying electron-transporting layer, it is possible to form the electron-transporting layer on the underlying organic film by the wet method without damaging the underlying organic film. As a result, the organic compound layer can have a uniform quality and can be free from pin-holes, making it possible to manufacture a long-life organic electroluminescent element that provides excellent luminescence at a low voltage.

The above-described phosphorus-containing organic compound has satisfactory properties in ionization potential, band gap, glass transition temperature and the like, and possesses good electron-transporting capability, hole-blocking capability and heat resistance. Accordingly, use of the above-described phosphorus-containing organic compound leads to a long-life organic electroluminescent element that provides excellent luminescence at a low voltage.

EXPLANATION OF REFERENCE NUMERALS

Figure 1:
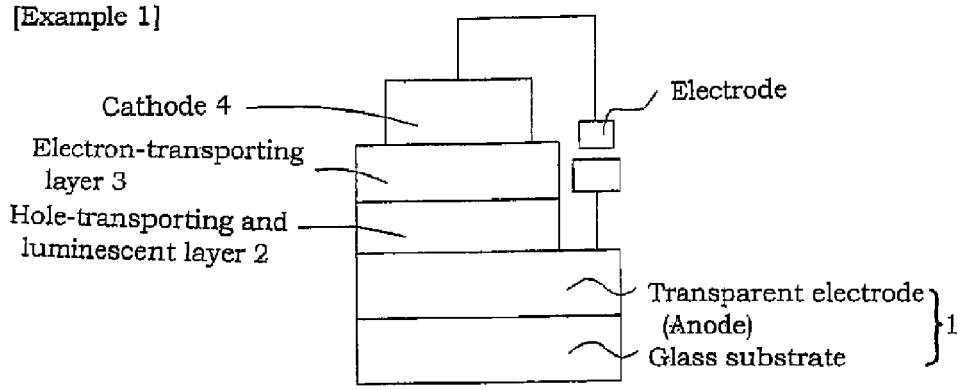
FIG. 1 is an explanatory view showing an organic electroluminescent element according to Example 1 of the present invention.

1 Glass substrate having a transparent electrode
2 Hole-transporting and luminescent layer
3 Electron-transporting layer
4 Cathode
5 Hole-injecting layer

BEST MODE FOR CARRYING OUT THE INVENTION

The organic electroluminescent element of the present invention comprises an anode, a cathode and a plurality of organic compound layers sandwiched between the anode and cathode, the organic compound layers including: a hole-transporting layer made of an organic compound insoluble in alcohols; and an electron-transporting layer formed on the hole-transporting layer by a wet method, the electron-transporting layer being made of a phosphorus-containing organic compound soluble in the alcohols.

The term "soluble" in the present specification means soluble enough for the solution obtained to be actually used with a wet method for forming a film, the solubility being preferably 0.1 g per liter or higher, for example.

The material of the electron-transporting layer is an organic compound soluble in alcohols when it is used with a wet method, while when it is used with a dry method, it is an organic compound that has a capability of being vapor-deposited under $10^{-3}$ Pa or lower. It is preferably a nonionic organic compound, particularly preferably a phosphorus-containing organic compound.

Usable as the phosphorus-containing organic compound are compounds represented by the general formulae (1)-(3):

(1)

wherein $Ar^1$-$Ar^3$, the same or different from each other, represent an aromatic ring residue optionally containing a substituent.

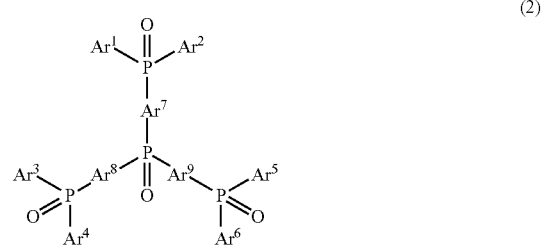

(2)

wherein $Ar^1$-$Ar^6$, the same or different from each other, represent an aromatic ring residue optionally containing a substituent; and Ar⁷-Ar⁹, the same or different from each other, represent an arylene group optionally containing a substituent.

(3)

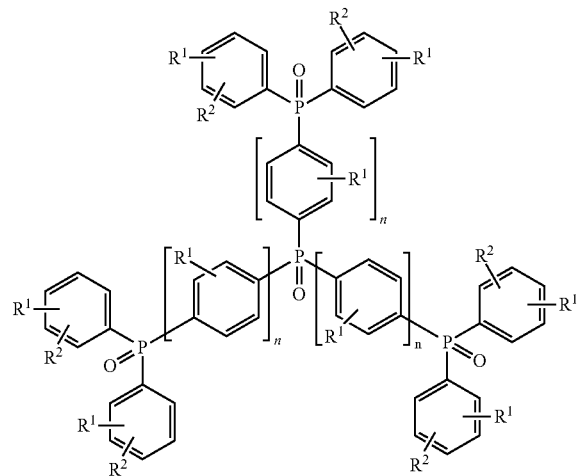

wherein $R^1$ or $R^2$, the same or different from each other, represents a hydrogen atom, an alkyl group, a halogen atom, cyano group, nitro group, amino group, an aryl group or a diarylphosphinyl group, and $R^1$ and $R^2$ can form, together with a carbon atom of a benzene ring to which they are linked, a substituted or unsubstituted aromatic ring; and n is 1 or 2.

Examples of the "aromatic ring residue" in the general formulae (1) and (2) include monocyclic aromatic ring residues and heterocycles such as a benzene ring, a thiophene ring, a triazine ring, a furan ring, a pyrazine ring and a pyridine ring; condensed polycyclic aromatic ring residues and heterocycles such as a naphthalene ring, an anthracene ring, a thieno[3,2-b]thiophene ring, a phenanthrene ring, a fluorene ring and a furo[3,2-b]furan ring; ring-aggregated aromatic ring residues and heterocycles such as a biphenyl ring, a terphenyl ring, a bithiophene ring and a bifuran ring; and aromatic ring residues and heterocycles such as a acridine ring, an isoquinoline ring, an indole ring, a carbazole ring, a carboline ring, a quinoline ring, a dibenzofuran furan ring, a cinnoline ring, a thionaphthene ring, a 1,10-phenanthroline ring, a phenothiazine ring, a purine ring, a benzofuran ring and a silol ring.

Examples of the "arylene group" in the general formala (2) include aromatic hydrocarbon groups such as a phenylene group, a naphthylene group, a biphenylene group, a phenanthrene group, a terphenylene group and a pyrenylene group. These may be substituted or unsubstituted.

Examples of the "aryl group" in the general formula (3) include aromatic hydrocarbon groups such as a phenyl group, a naphthyl group, a biphenyl group, a phenanthryl group, a terphenyl group and a pyrenyl group. These may be substituted or unsubstituted.

Examples of substituents in the "aryl group" and "aromatic ring residue" include an alkyl group, an alkoxy group, a halogen atom, cyano group, nitro group, amino group, an aryl group and a diarylphosphinyl group.

The phosphorus-containing organic compound of the present invention is preferably a nonionic organic compound which has a high electrochemical stability, is reluctant to crystallize and has a long life when used for the organic electroluminescent element.

The phosphorus-containing organic compound of the present invention preferably has a molecular weight of 300-5000, more preferably, in view of its solubility in alcohols and its capability of being vapor-deposited, 300-1500 when it is used with a wet method and 300-1200 when it is used with a dry method.

The present invention provides a manufacturing method of an organic electroluminescent element including an anode, a cathode and a plurality of organic compound layers sandwiched between the anode and cathode, comprising the steps of: forming a hole-transporting layer using an organic compound insoluble in alcohols; and forming an electron-transporting layer on the hole-transporting layer by a wet method using as an electron transporting layer material a phosphorus-containing organic compound to be dissolved in an alcohol.

The electron-transporting layer surface of the organic electroluminescent element manufactured by the method of the present invention preferably has a arithmetical mean roughness (Ra) of 10 nm or less, more preferably 1 nm or less in view of an improvement in the luminescence of the organic electroluminescent element.

The phosphorus-containing organic compounds represented by the general formulae (1)-(3) are used as an electron transporting layer material that is soluble in alcohols.

Examples of alcohols include linear or branched $C_1$-$C_6$ aliphatic alcohols such as methanol, ethanol, 1-propanol, 2-propanol, 1-butanol, 2-butanol, 2-methyl-1-propanol and 2-methyl-2-propanol; and glycol-type solvents such as ethylene glycol monomethyl ether and ethylene glycol monoethyl ether, among which preferable are the linear or branched $C_1$-$C_6$ aliphatic alcohols. These may be used in a combination of two or more.

Examples of the wet methods include a spin coating method, an inlet method, an a spraying method, a dip coating method, a blade coating method, a wire bar coating method, a casting method, a roll coating method, and printing methods such as screen printing, gravure printing, offset printing and the like.

When the electron-transporting layer is formed by the wet method, the above-mentioned alcohols may be used in combination with a solvent other than the above-mentioned alcohols.

Other steps in the manufacture of the organic electroluminescent element are not particularly limited and may be performed with known methods.

Examples of the dry methods include a vacuum deposition method, a CVD method and the like.

There will be described the present organic electroluminescent element that uses the electron-transporting material.

The organic electroluminescent element has a layer structure exemplified as follows:
(1) A substrate; an anode; a luminescent layer; and a cathode (rear electrode)
(2) A substrate; an anode; a luminescent layer; one or more organic compound layers containing an electron-transporting material; and a cathode
(3) A substrate; an anode; one or more organic compound layers containing a hole-transporting material; a luminescent layer; and a cathode
(4) A substrate; an anode; one or more organic compound layers containing a hole-transporting-material; a luminescent layer; one or more organic compound layers containing an electron-transporting material; and a cathode Each of the above layer structures (1)-(4) may include a hole-injecting layer and/or an electron-injecting layer.

The choice of materials depends on whether it is the substrate side or the cathode side from which light is taken out. When light is taken out from the substrate side, the substrate and the anode are formed of a transparent material, while when light is taken out from the cathode side, the cathode is formed of a transparent material.

The organic electroluminescent element may further include a hole-blocking layer and/or an electron-injecting layer.

Further, the luminescent layer may contain either a hole-transporting material or an electron-transporting material, and may function either as a hole-transporting and luminescent layer or as an electron-transporting and luminescent layer.

In addition, the luminescent layer may be doped with a luminescent material at its hole-transporting layer side and/or at its electron-transporting layer side.

The material of the substrate is not particularly limited and may be a known material. Known materials include glass, plastic, a thin metal film, silicon, quartz and the like. Also, the substrate may have a fluorescent-color conversion filter film, a color filter film, a dielectric reflective film and the like, for control of the luminescent color.

The material of the anode is not particularly limited and may be a known material. Known materials include indium tin oxide (ITO), titanium oxide, tin oxide, metals such as gold, platinum, nickel, palladium, cobalt, selenium, vanadium and the like, and alloys thereof; and conductive polymers such as polyaniline, polypyrrol, polythiophene, polyphenylene sulfide and the like. These electrode materials may be used alone or in combination.

The method of forming the electrode is not particularly limited and may be a known method. Known methods include thin-film formation methods such as a vacuum deposition method, a sputtering method, a sol-gel method, a spin coating method, an inkjet method and the like.

The material of the cathode is not particularly limited and may be a known material. Known materials include metals such as lithium, aluminum, magnesium, sodium, potassium, calcium, indium, silver, lead, tin, chromium and the like, and alloys thereof; and metal oxides such as indium tin oxide (ITO) and the like.

The cathode may have a single-layered or multilayered structure.

The method of forming the electrode is not particularly limited and may be a known method.

The material of the hole-transporting layer is not particularly limited and may be a known material. When the hole-transporting layer is formed by a wet method, the material is selected from ones that do not dissolve in the alcohol used with the wet method for the formation of the electron-transporting layer.

Materials of the hole-transporting layer include conductive polymers, low-molecular organic semiconductors, and composite materials prepared by dispersing a low-molecular organic semiconductor in an insulative polymer such as poly(methyl acrylate), poly(butyl acrylate) or polycarbonate, as well as composite materials of two or more of these.

Examples of the conductive polymers include poly(dioctyl-fluorene) (POF), polyvinyl carbazole (PVK), polyphenylene (PP), polyfluorene (PF), polythiophene (PT), polyparaphenylene vinylene (PPV) and polyacetylene (PA), as well as composite materials of two or more of these, derivatives and copolymers of these conductive polymers, and copolymers of one or more of these conductive polymers with a polyacene or with a fluorescent pigment.

Examples of the low-molecular organic semiconductors include phenylenediamine derivatives (e.g., N,N'-bis(3-methylphenyl)-N,N'-bis(phenyl)-benzidine(TPD) and the like), triphenylamine derivatives, carbazole derivatives and phenyl styrene derivatives, as well as composite materials of two or more of these.

The material of the hole-injecting layer is not particularly limited and may be a known material. Known materials include PEDT/PSS (polyethylenedioxythiophene/polystyrene sulfonic acid), copper phthalocyanine and the like.

The material of the electron-injecting layer is not particularly limited and may be a known material. Known materials include alkali metal fluorides such as lithium fluoride, cesium fluoride and the like; alkali earth metal fluorides such as magnesium fluoride, calcium fluoride and the like; lithium complexes such as acetylacetosodium, lithium quinolilate and the like; and composite films of vasophenanthroline or bathocuproin doped with metal sodium or metal lithium.

The present invention provides a phosphorus-containing organic compound as a condensation product of a compound represented by the general formula (4):

(4)

wherein $Ar^{11}$, the same or different from each other, represent a phenyl group or naphthyl group optionally substituted with a halogen atom, a lower alkyl group, a lower alkoxy group or a phenyl group, and either
a compound represented by the formula:

$$Ar^{12}$$

wherein $Ar^{12}$ represents benzene substituted with three halogen atoms, benzene or biphenyl substituted with two halogen atoms
or
a compound represented by the general formula (5):

(5)

wherein $Ar^{13}$, the same or different from each other, are a phenyl group or biphenyl group optionally substituted with a halogen atom, at least two of $Ar^{13}$ being a phenyl group or biphenyl group substituted with at least one halogen atom.

Preferable examples of the above-mentioned condensation product include compounds represented by the following subformulae (6)-(8):

(6)

wherein Ar¹¹ has the same meaning as defined in the general formula (4); and Ar¹²' represents a phenylene group or biphenylene group when n=2 and a benzenetriyl group when n=3.

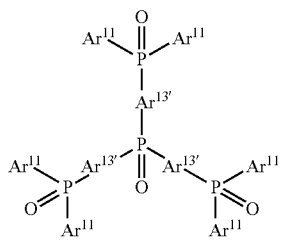
(7)

wherein Ar¹¹ has the same meaning as defined in the general formula (4); and Ar¹³', the same or different from each other, represent a phenylene group or a biphenylene group.

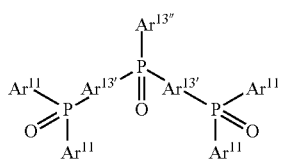
(8)

wherein Ar¹¹ has the same meaning as defined in the general formula (4); Ar¹³', the same or different from each other, represent a phenylene group or a biphenylene group; and Ar¹³'' represents a phenyl group or a biphenyl group.

Ar¹¹, Ar¹², Ar¹²', Ar¹³, Ar¹³' and Ar¹³'' in the subformulae (6)-(8) are substantially the same as, though partially different from, Ar¹-Ar³ in the general formula (1) and Ar¹-Ar⁹ in the general formulae (2) and (3).

Examples of the "halogen atom" in substituent Ar¹ include fluorine, chlorine, bromine, iodine and the like.

Examples of the "lower alkyl group" in substituent Ar¹¹ include methyl group, ethyl group, n-propyl group, iso-propyl group, n-butyl group, iso-butyl group, tert-butyl group (also referred to as t-butyl), and the like.

Examples of the "lower alkoxy group" in the substituent Ar¹¹ include methoxy group, ethoxy group, propoxy group, butoxy group and the like.

Particularly preferable examples of the substituent Ar¹¹ include an unsubstituted phenyl group; and a phenyl group, biphenyl or naphthyl group substituted with methyl group, t-butyl group or methoxy group.

In the case where the substituents Ar¹¹ in the subformulae (6)-(8) include a phenyl group and a naphthyl group, the phenyl group and the naphthyl group may be linked to the same phosphorus atom.

Specific examples of the phosphorus-containing organic compound represented by the subformula (6) (n=6) include compounds represented by the following formulae. In the following formulae, only skeletons are illustrated, and substituents in substituted Ar¹¹ are omitted.

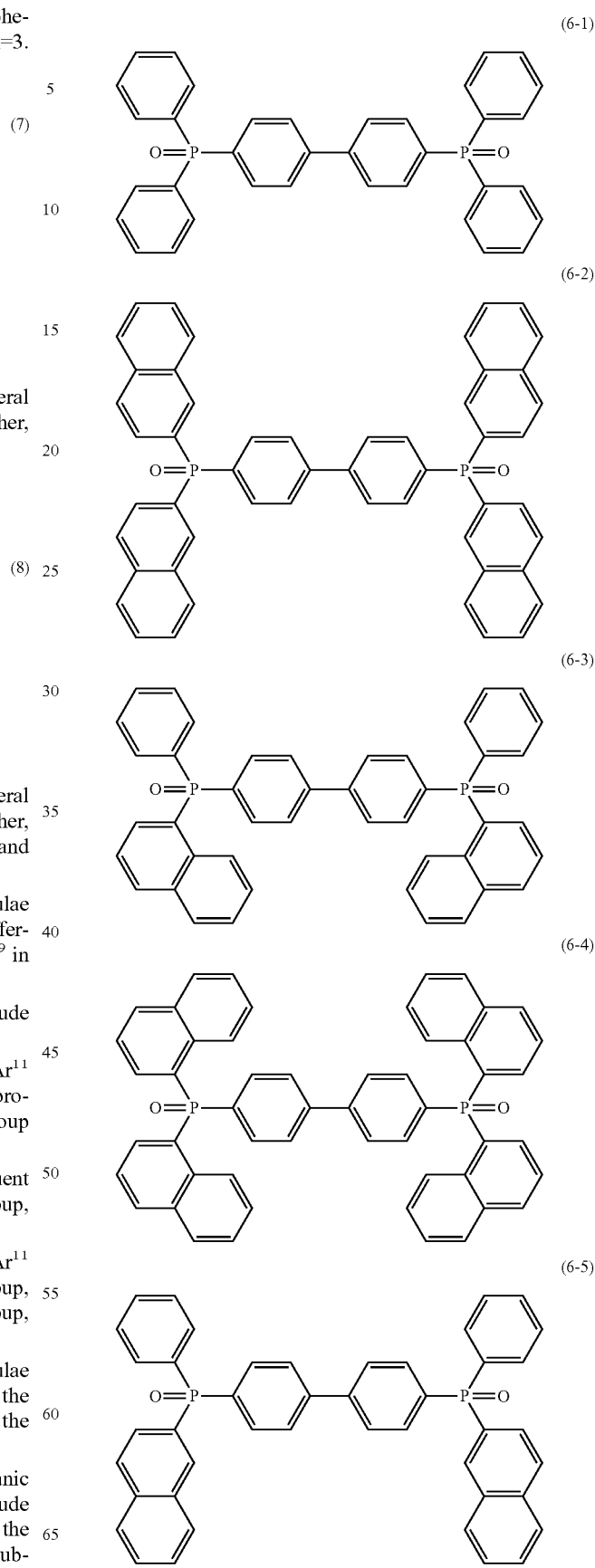

(6-6)
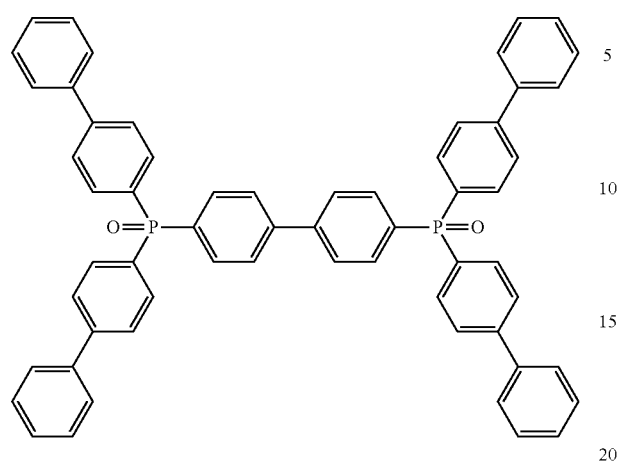
(6-3)
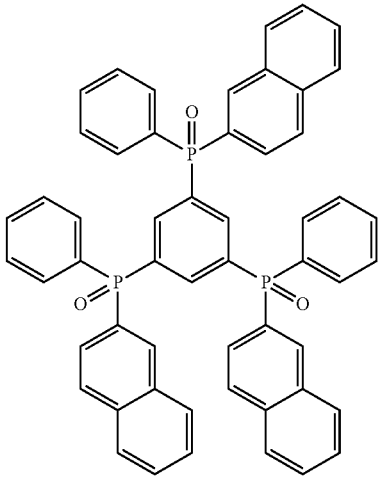
Specific examples of the phosphorus-containing organic compounds represented by subformula (6) (n=3) include the following compounds:
(6-1)
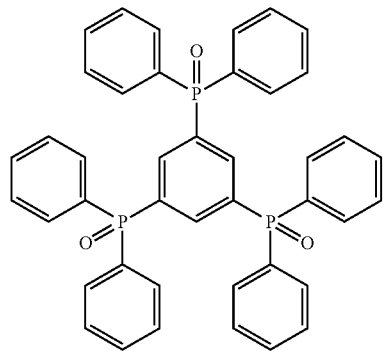
(6-4)
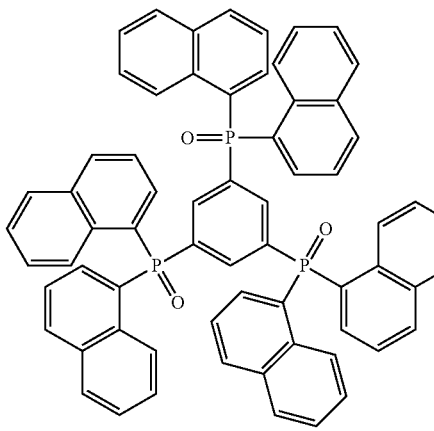
(6-5)
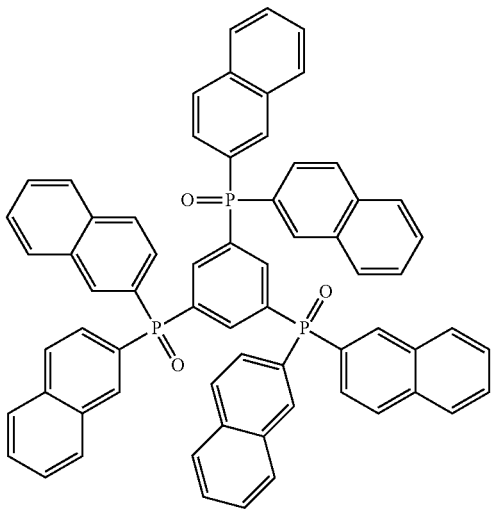
(6-2)
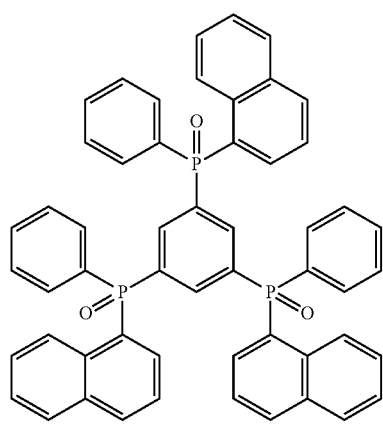
Specific examples of the phosphorus-containing organic compounds represented by the subformula (7) include the following compounds:

(7-1)
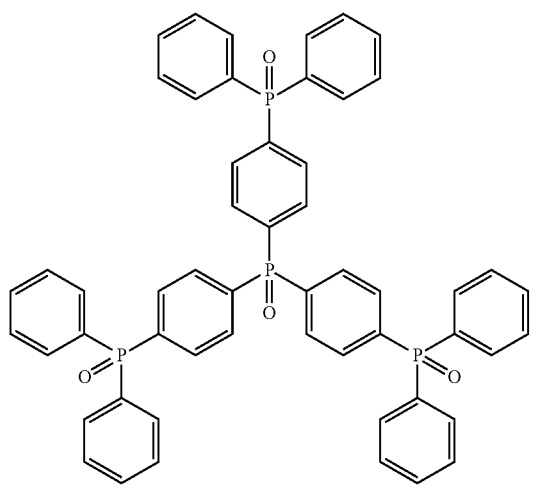
(7-4)
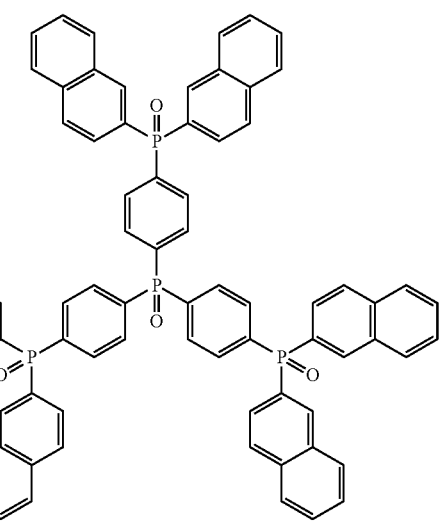
(7-2)
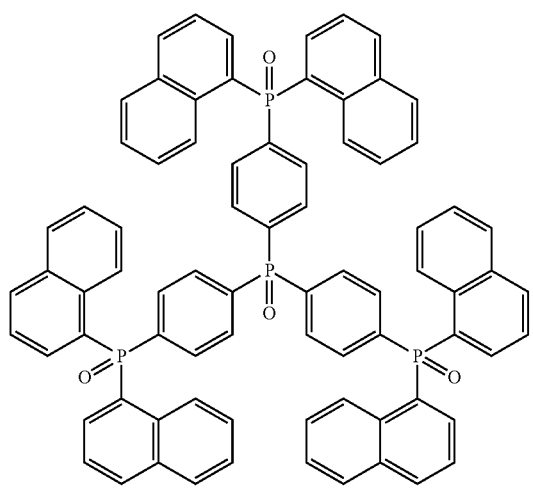
(7-5)
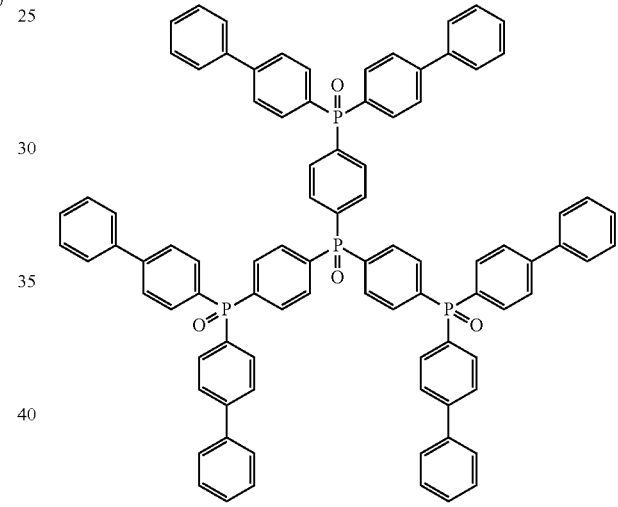
(7-3)
(7-6)
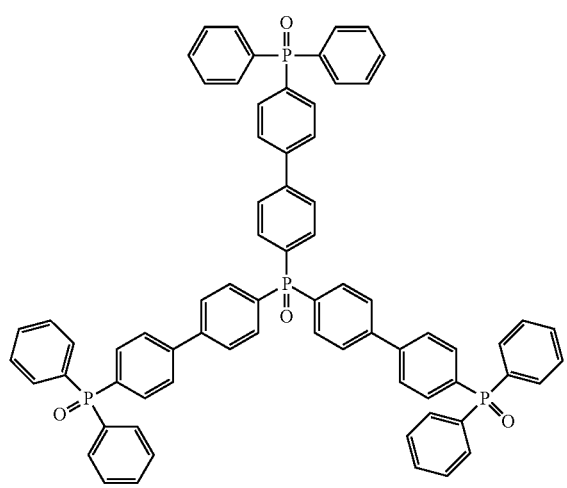

(7-7)
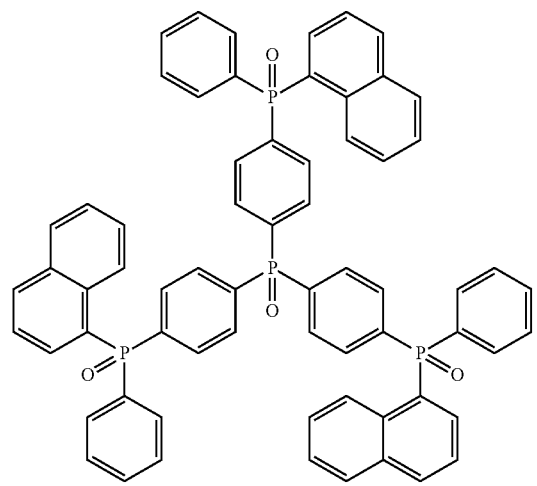
(7-8)
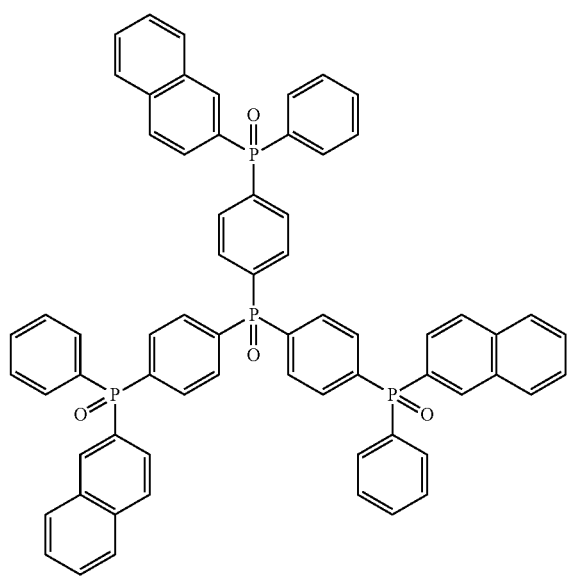
Specific examples of the phosphorus-containing organic compounds represented by the subformula (8) include the following compounds:
(8-1)
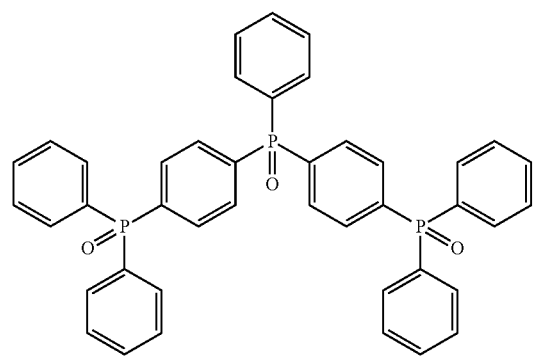
(8-2)
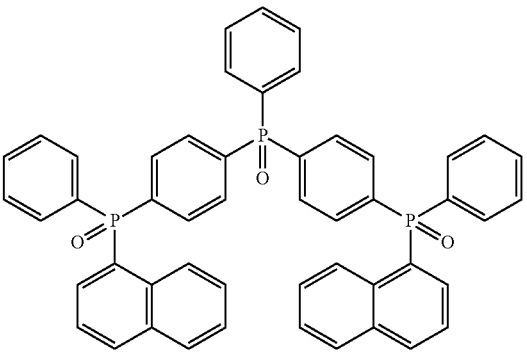
(8-3)
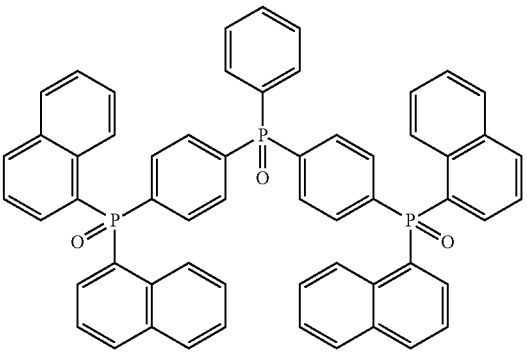
(8-4)
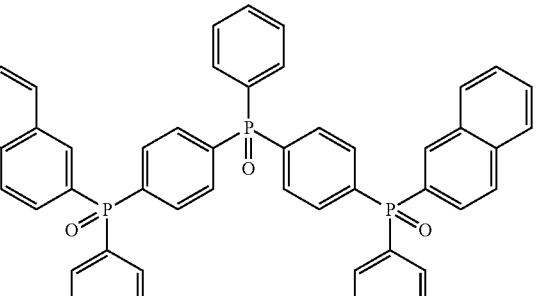
(8-5)
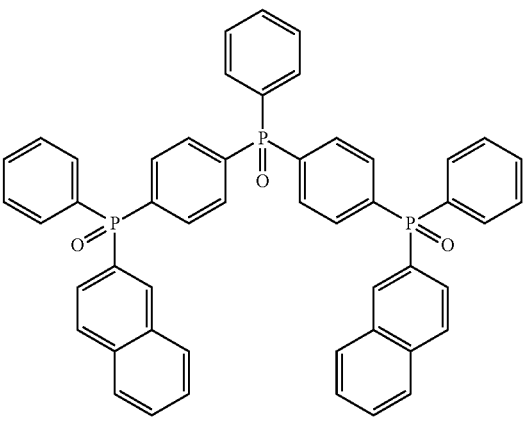

Specific examples of phosphorus-containing organic compounds other than the above include the following compounds:
(0-1)
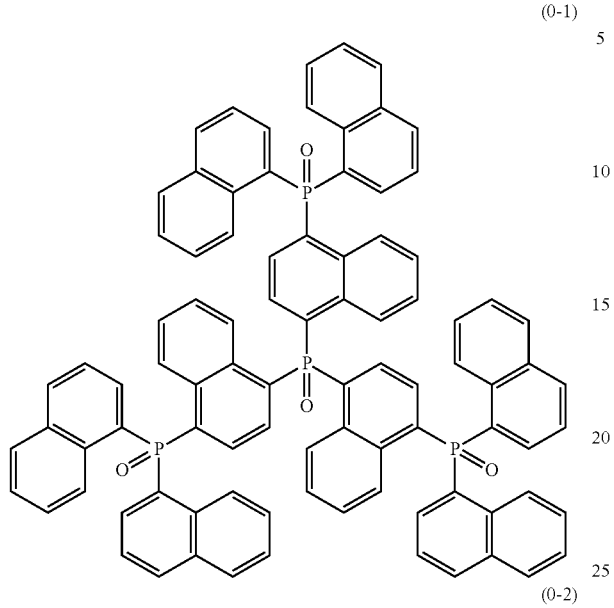
(0-2)
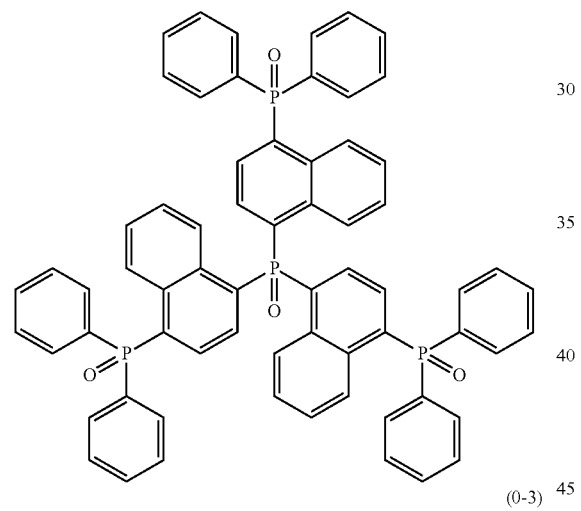
(0-3)
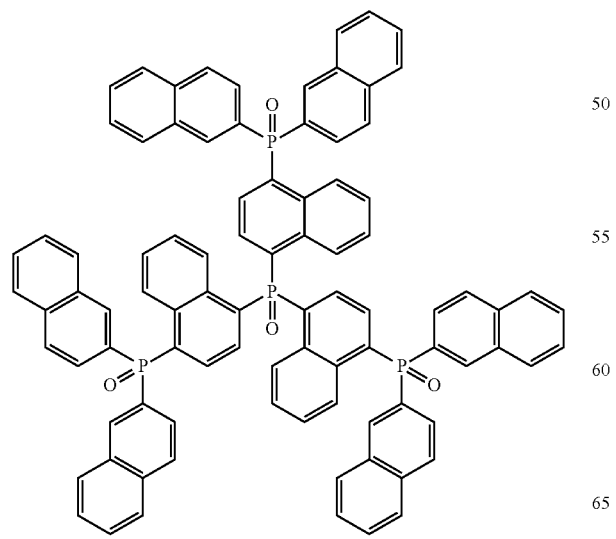
(0-4)
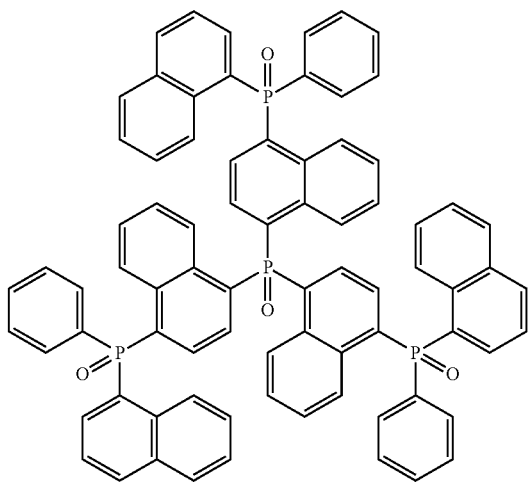
(0-5)
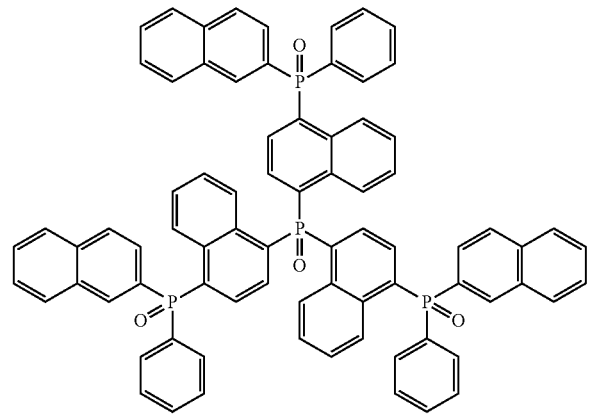
(0-6)
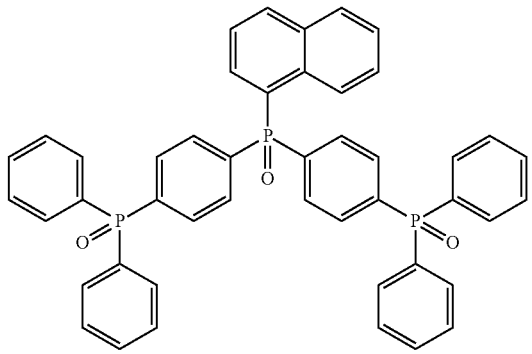

(0-7)
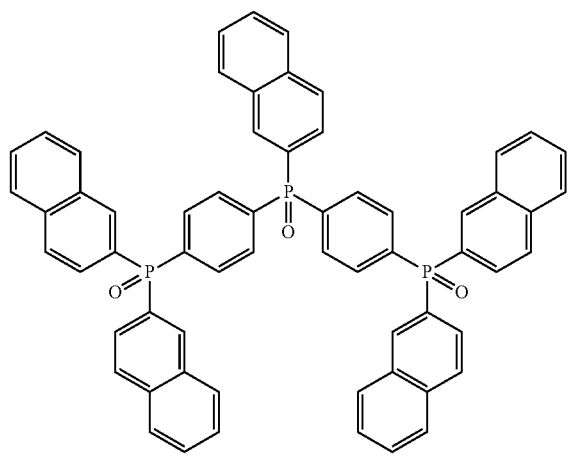
(0-8)
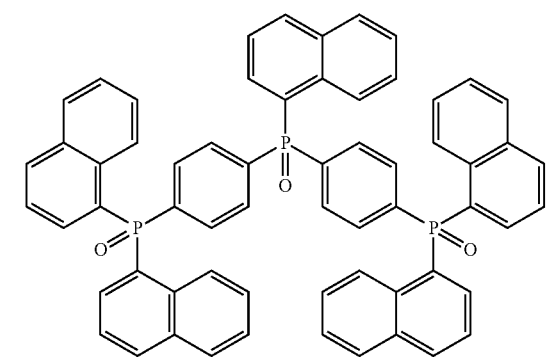
(0-9)
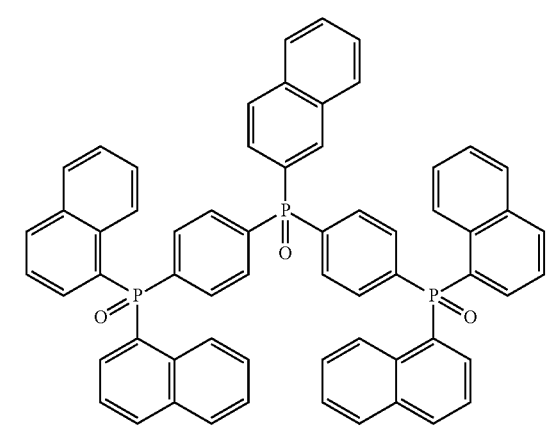
(0-10)
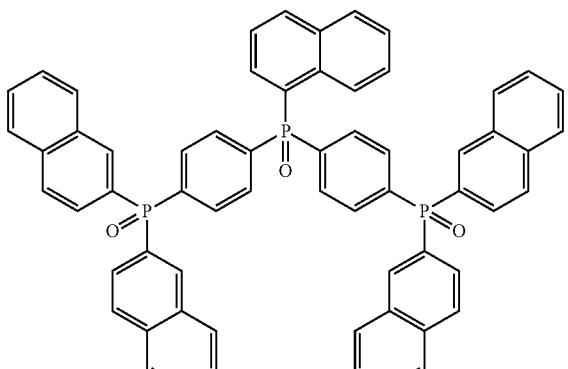
(0-11)
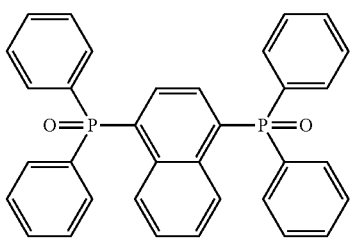
(0-12)
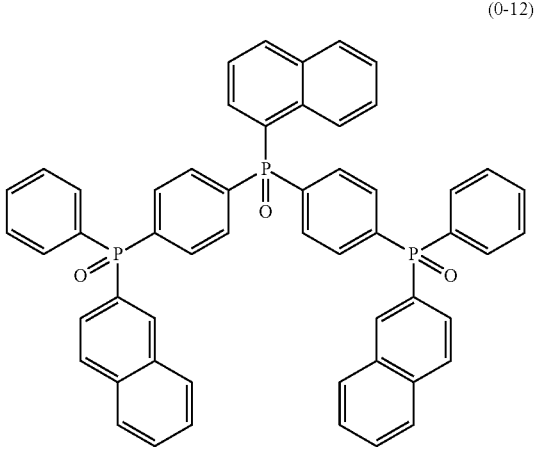 [SMILES: O=P(c1ccccc1)(c1ccc(P(=O)(c2ccccc2)c2ccc3ccccc3c2)cc1)c1ccc(P(=O)(c2ccccc2)c2ccc3ccccc3c2)cc1]
(0-13)
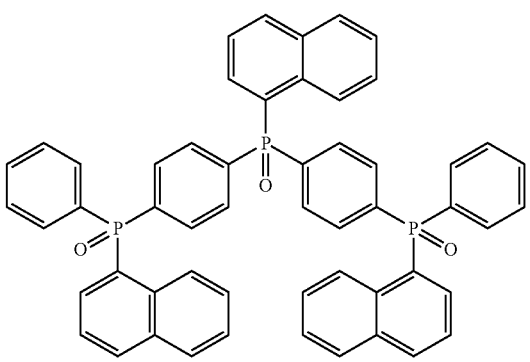

-continued (0-14)
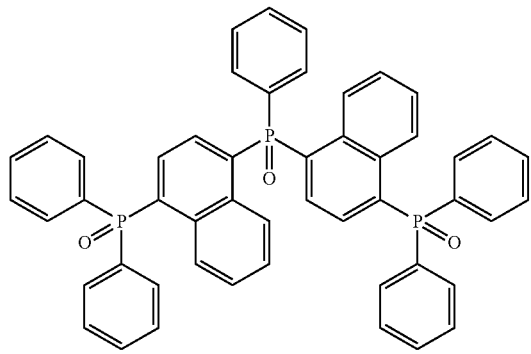

(0-15)
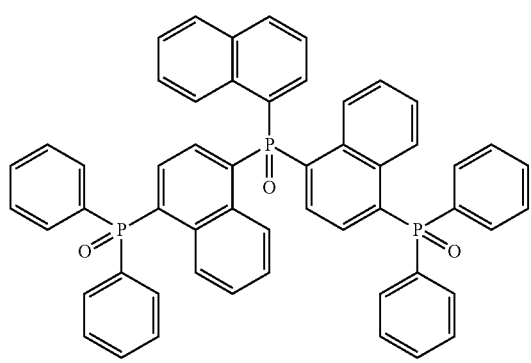

(0-16)
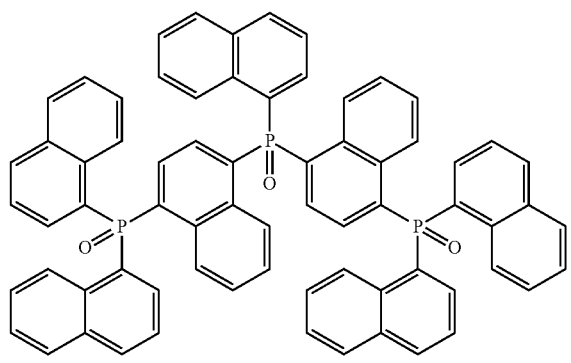

(0-17)
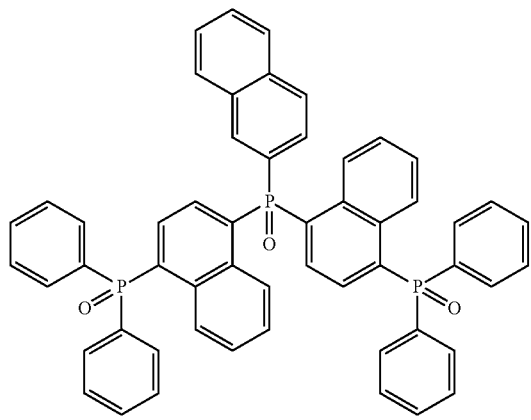

However, the above specific examples are merely for an illustrative purpose and the phosphorus-containing organic compound of the present invention is not limited to the above.

The phosphorus-containing organic compound of the present invention preferably has at least three partial structures represented by a diarylphosphine oxide skeleton, the diarylphosphine oxide skeleton represented by either the formula (9):

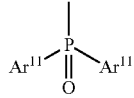
(9)

wherein $Ar^{11}$ has the same meaning as defined in the general formula (4) or the formula (10):

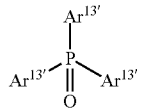
(10)

wherein $Ar^{13'}$, the same or different from each other, are a phenyl group or a biphenyl group, or a phenylene group or biphenylene group linked to the formula (9).

The phosphorus-containing organic compound having said at least three partial structures has an excellent effect of transporting electrons, as the electron transporting layer material for the organic electroluminescent element.

The phosphorus-containing organic compound of the present invention may be synthesized by a known method.

The phosphorus-containing organic compound of the present invention can be manufactured by condensing (dehydrohalogenating), in a solvent, in the presence of a condensing catalyst and a base, a compound of the general formula (4) (compound 4) with either a compound of the formula: $Ar^{12}$ or a compound of the general formula (5) (compound 5).

For example, the use amount of the compound 4 for manufacture of the compound of the subformula (6) (n=2) is about 2.0-4.5 moles with respect to one mole of the compound $Ar^{12}$.

The amount of the compound 4 to be used for manufacture of the compound of the subformula (6) (n=3) is about 3.0-7.5 moles with respect to one mole of the compound $Ar^{12}$.

The amount of the compound 4 to be used for manufacture of the compound of the subformula (7) is about 3.0-7.5 moles with respect to one mole of the compound 5.

The amount of the compound 4 to be used for manufacture of the compound of the subformula (8) is about 2.0-4.5 moles with respect to one mole of the compound 5.

Examples of the above solvent include dimethyl sulfoxide (DMSO), dimethylformamide (DMF), tetrahydrofuran (THF), dioxane, pyridine, benzene, toluene, xylene and the like, among which preferable is DMSO in terms of yield.

Examples of the above condensing catalyst include palladium acetate [Pd(OAc)$_2$], nickel acetate[Ni(OAc)$_2$], and complex compounds of elements belonging to the platinum family and bisphosphinoalkanes such as Pd(OAc)$_2$-1,3-bis (diphenylphosphino)propane[dppp], Pd(OAc)$_2$-1,2-bis (diphenylphosphino)ethane[dppb], Pd(OAc)$_2$-1,4-bis(diphenylphosphino)butane[dppb], Ni(OAc)$_2$-dppe and Ni(OAc)$_2$-dppp. Among these, preferable are Pd(OAc)$_2$, Pd(OAc)$_2$-dppp and Pd(OAc)$_2$-dppb in terms of yield.

The amount of the catalyst to be used is about 0.005-0.1 moles with respect to one mole of the compound 4.

The base has a function to capture hydrogen halide generated by the condensation.

Examples of the base include trialkylamines such as triethylamine, tripropylamine and tributylamine; aliphatic tertiary amines such as N-ethyldiisopropylamine[edpa]; and aromatic tertiary amines such as pyridine and N,N'-dimethylaminopyridine[DMAP]. Among these, preferable are edpa and DMAP in terms of boiling point.

The amount of the base to be used is an amount sufficient to capture the theoretical amount of hydrogen halogenide generated. That is, it is about 1.0-1.2 moles with respect to one mole of the compound 4.

The reaction temperature in the condensation reaction according to the present invention is preferably 60-180° C., more preferably 80-130° C.

The reaction time depends on conditions such as reaction temperature, and typically a reaction time of 1-48 hours is sufficient.

After the reaction, the target compound is separated from the reaction solution obtained, by a known method. For example, the target compound is extracted with chloroform/distilled water from the reaction solution, and the chloroform phase is separated and concentrated. The target compound obtained may further be purified. For example, the remaining viscous liquid is dissolved in a small amount of chloroform, and the resulting solution is subjected to column chromatography that uses silica gel as a filler, to separate the target compound. After the separation, the target compound is recrystallized, and further purified by sublimation in a vacuum.

The phosphorus-containing organic compound thus obtained can be used as the electron-transporting material for the organic electroluminescent element.

Among the aforementioned examples of the present phosphorus-containing organic compound, preferable as the electron-transporting material for the organic electroluminescent element are the following compounds:

Compounds of the subformula (6):

(A)

(B)

(C)

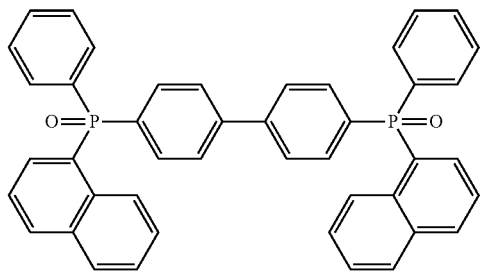

(D)

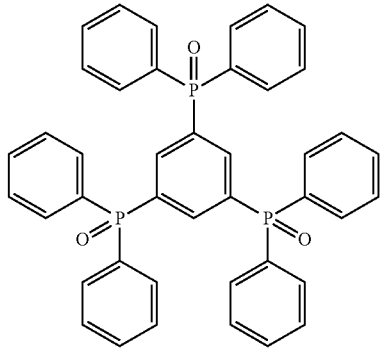

Compounds of the subformula (7):

(E)

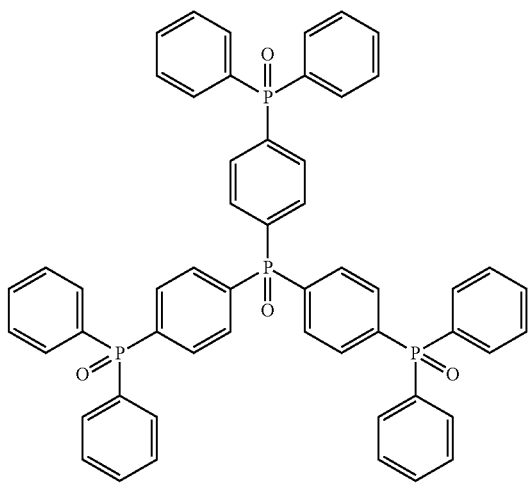

(F)

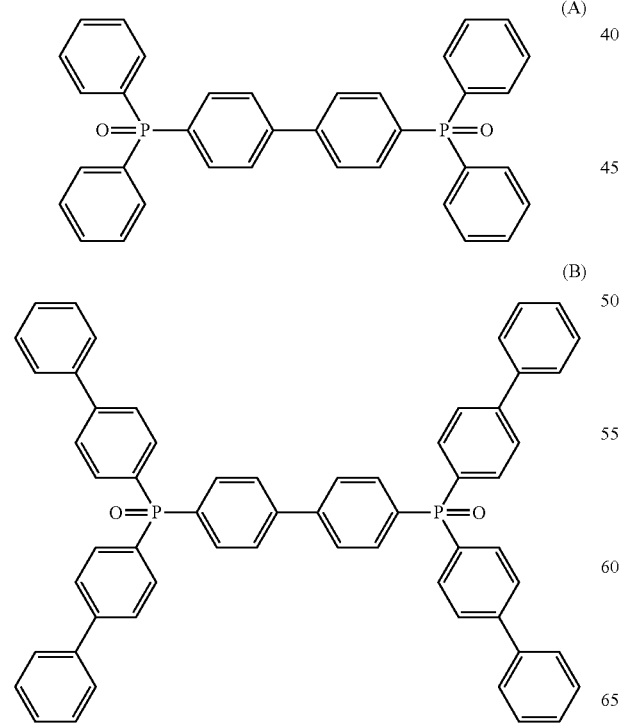

(G)
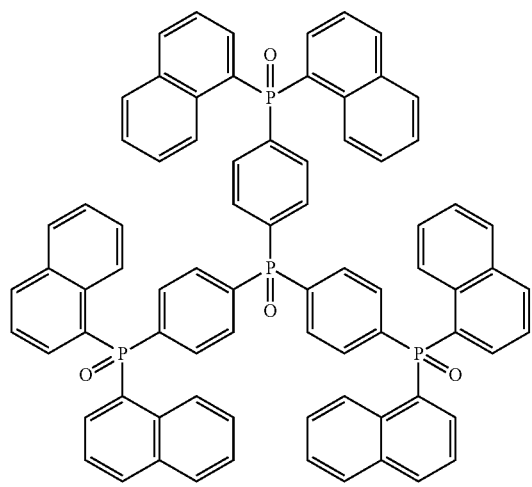
(H)
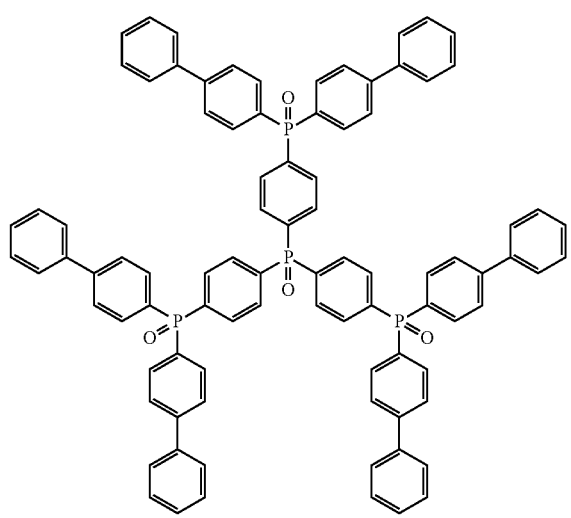
(I)
(J)
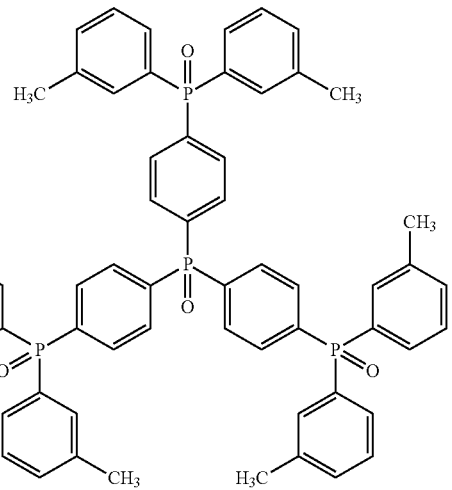
(K)
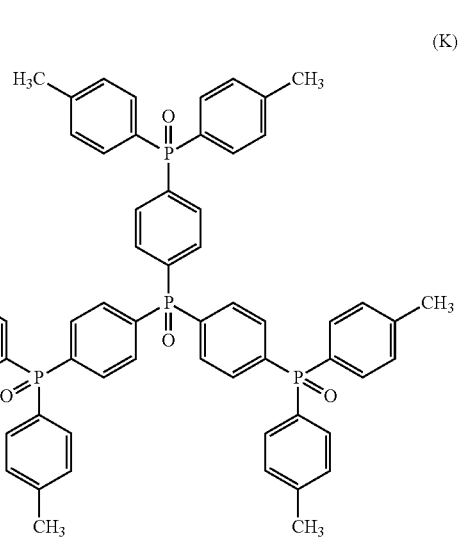
(L)
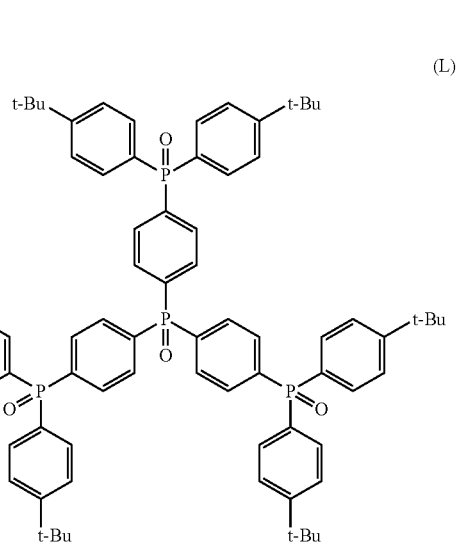

Compounds of the subformula (8):

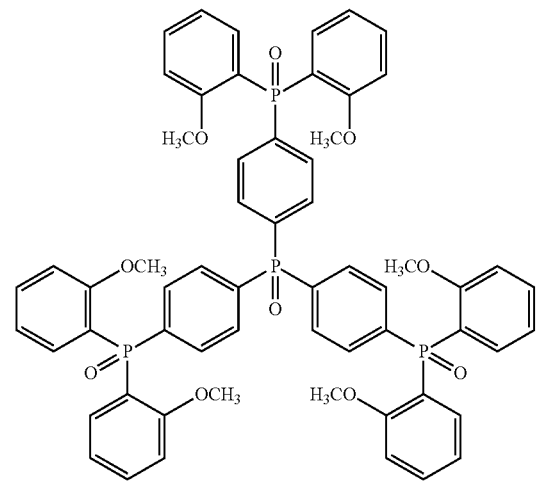

(M)

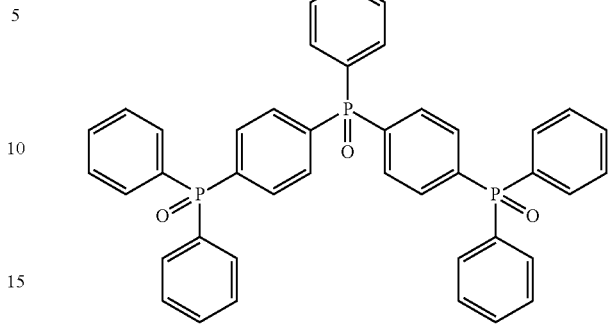

(P)

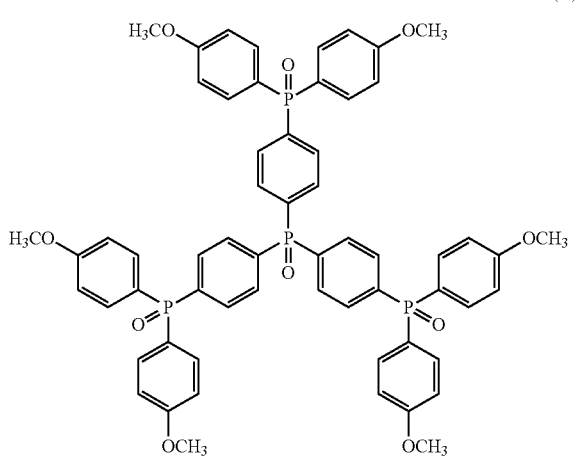

(N)

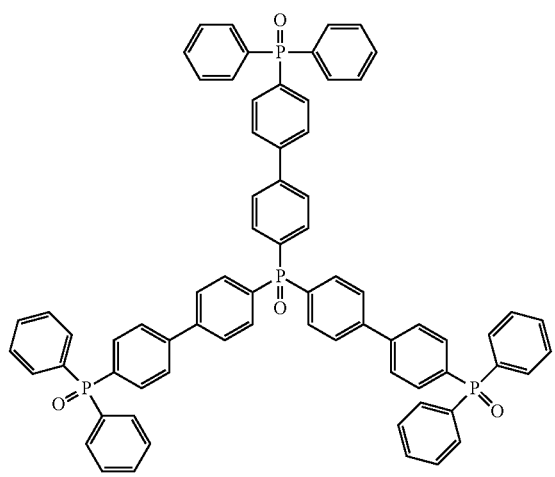

(O)

The phosphorus-containing organic compound of the present invention is considered to have the same properties as those of organic semiconductors in general use, and its application to devices is expected. Examples of devices to which the compound of the present invention is expected to be applied include organophotoreceptors, organic thin film lasers, organic solar cells, organic field-effect transistors, organic volatile memories, organic nonvolatile memories, antistatic agents and the like. Examples of products to which these devices are expected to be applied include TFT substrates for liquid crystal display, TFT substrates for organic EL, organic integrated circuits, copying machines, facsimiles, mobile telephones, non-contact IC cards and tags, personal computers and the like.

The phosphorus-containing organic compound of the present invention has a partial structure represented by a diarylphosphine oxide skeleton, and is also referred to as a "triarylphosphine oxide compound" in the present specification.

Hereafter, the present invention will be described by way of Examples. However, the present invention should not be construed as being limited by these Examples.

EXAMPLE 1

(1) Synthesis of 4,4',4"-tris(diphenylphosphinyl)-triphenylphosphine oxide (also referred to as "TPPO-Burst")

In Example 1, TPPO-Burst represented by the following formula was synthesized.

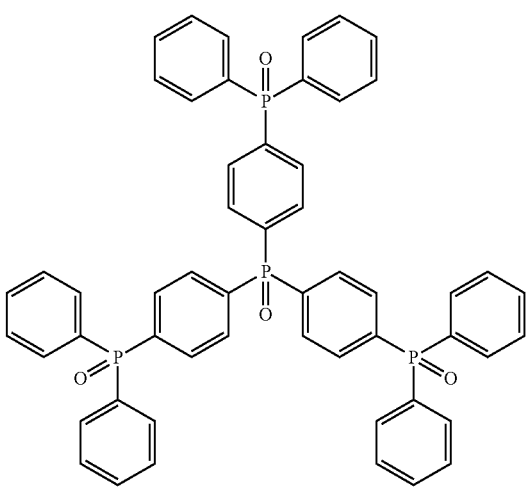 [SMILES: O=P(c1ccccc1)(c1ccccc1)c1ccc(P(=O)(c2ccc(P(=O)(c3ccccc3)c3ccccc3)cc2)c2ccc(P(=O)(c3ccccc3)c3ccccc3)cc2)cc1]

TPPO-Burst (product) was synthesized as shown in the following reaction scheme. First, triphenylphosphine oxide (intermediate 6) and diphenylphosphine oxide (intermediate 7) were synthesized and then, from the intermediate 6 and the intermediate 7, the TPPO-Burst was synthesized.

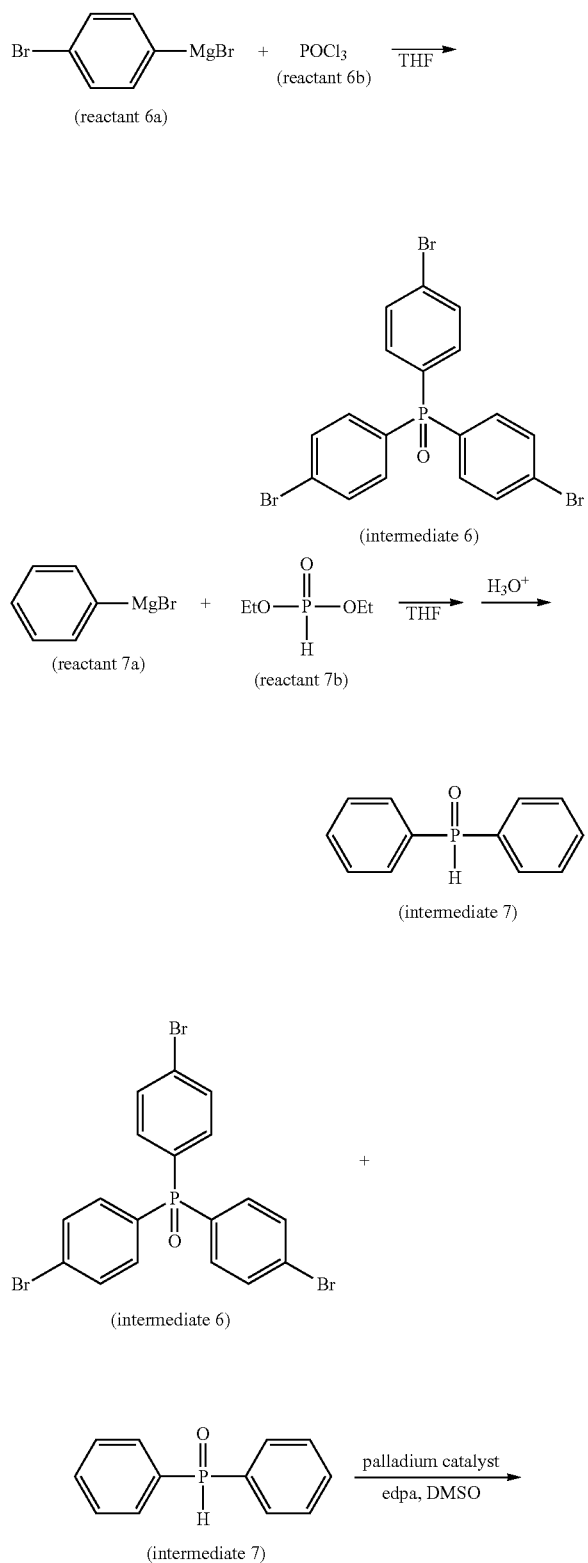

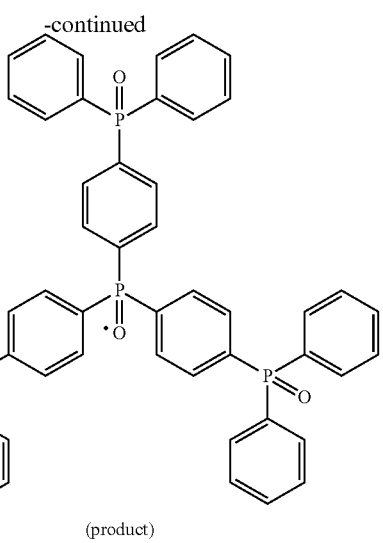

(1-1) Synthesis of Triphenylphosphine Oxide (Intermediate 6)

A solution of 26.0 g (110 mmol) of 1,4-dibromobenzene in absolute THF was dripped onto 2.40 g (98.8 mmol) of a magnesium metal piece in an atmosphere of nitrogen, to prepare a Grignard reagent (reactant 6a). To the solution, a solution of 4.6 g (30 mmol) of phosphorus oxychloride (reactant 6b) in absolute THF was slowly dropwise added. After completion of the addition, the resulting solution was stirred overnight. To the solution, 17 mL of a hydrochloric acid solution (concentration 36%) was added dropwise. The target compound was extracted with distilled water/chloroform from the solution, and the chloroform phase was separated, and concentrated by a rotary evaporator. The remaining viscous liquid was dissolved in a small amount of chloroform, and the resulting solution was subjected to column chromatography that used silica gel as a filler, to separate the target compound. After the separation, the target compound was further recrystallized. The crystals obtained were subjected to FAB mass analysis, whereby it was confirmed that (molecular weight)=515, (molecular weight)+2=517, and (molecular weight)+4=519, and that the crystals obtained were the target intermediate 6 (yield 5.21 g (10.1 mmol), 34%).

(1-2) Synthesis of Diphenylphosphine Oxide (Intermediate 7)

A solution of 17.2 g (110 mmol) of bromobenzene in absolute THF was dripped onto 2.4 g (98.8 mmol) of a magnesium metal piece in an atmosphere of nitrogen while cooling the solution to prevent reflux of the solvent, to prepare a Grignard reagent (reactant 7a). To the solution, a solution of 5.18 g (37.5 mmol) of diethylphosphite (reactant 7b) in absolute THF was slowly dropwise added. After completion of the addition, the resulting solution was stirred overnight. To the solution, 1 mol/l hydrochloric acid was added dropwise. The target compound was extracted with distilled water/chloroform from the solution, and the chloroform phase was separated, and concentrated by a rotary evaporator. The remaining viscous liquid was dissolved in a small amount of chloroform, and the resulting solution was subjected to column chromatography that used silica gel as a filler, to separate the target compound. After the separation, the target compound was further recrystallized. The crystals obtained were subjected to FAB mass analysis, whereby it was confirmed that (molecular weight)+1=203, and that the crystals obtained were the target intermediate 7 (yield 3.57 g (17.7 mmol), 47%).

(1-3) Synthesis of TPPO-Burst as the Product from the Intermediate 6 and the Intermediate 7

The intermediate 7 of 2.55 g (12.6 mmol) was reacted with 1.06 g (2.05 mmol) of triphenylphosphine oxide serving as an intermediate b, in 20 ml of DMSO serving a solvent at 100° C. in the presence of 93.3 mg (0.416 mmol) of Pd(OAc)$_2$, 257 mg (0.623 mmol) of dppp and 3.7 ml of edpa. The target compound was extracted with distilled water/chloroform from the solution and concentrated. The remaining viscous liquid was dissolved in a small amount of chloroform, and the resulting solution was subjected to column chromatography that used silica gel as a filler, to separate the target compound. After the separation, the target compound was recrystallized, and further purified by sublimation at a degree of vacuum of $2\times10^{-4}$ Pa. The crystals obtained were subjected to FAB mass analysis, whereby it was confirmed that (molecular weight)=879, and that the crystals obtained were the target TPPO-Burst (yield 1.39 g (1.58 mmol), 77%, Tm: 399 r, Tg: 149° C.).

(2) Properties of the TPPO-Burst (2-1) Ionization Potential and Band Gap

The ionization potential of the TPPO-Burst was measured by an ultraviolet-ray electron spectrometer (AC-2) manufactured by RIKENKEIKI Co., Ltd. and found to be beyond 6.8 eV because the threshold was not detected up to the measurement limit of 6.8 eV. The band gap was 3.96 eV. Thus, it was noted that the TPPO-Burst had a higher ionization potential and a larger band gap than the ionization potential and band gap of bathocuproin which was in general use as an electron-transporting material, as an hole-blocking material and as an exciton-confining material (the ionization potential of bathocuproin: 6.8 eV, the band gap thereof: 3.7 eV). This indicates that TPPO-Burst has a high capability to block holes and a great effect of confining excitons and is promising as a hole-blocking material and as an exciton-confining material for a phosphorescent element.

(2-2) Glass Transition Temperature

The Tg of the TPPO-Burst obtained was measured by DSC-6200 manufactured by Seiko Instruments & Electronics Ltd. according to differential thermal analysis, and found to be as high as 149° C. The Tg of 149° C. is higher than the Tg (63° C.) of N,N'-bis(3-methylphenyl)-N,N'-bis(phenyl)-benzidine (TPD) which is in general use as a hole-transporting material. This indicates that TPPO-Burst has excellent heat resistance.

(3) Manufacture of an Organic Electroluminescent Element Using TPPO-Burst

FIG. 1 is an explanatory view showing an organic electroluminescent element according to Example 1. The element according to Example 1 was manufactured using TPPO-Burst as an electron-transporting material. The following are details of the constitution of the element (see FIG. 1).

transparent electrode (ITO)/hole-transporting and luminescent layer (POF)/electron-transporting layer (TPPO-Burst)/cathode (MgAg)

A glass substrate 1 having a transparent electrode (100 nm) of indium tin oxide (ITO) was cleaned ultrasonically sequentially with an alkaline detergent, distilled water, acetone, isopropyl alcohol (IPA) twice each, and dried.

POF (poly(dioctyl-fluorene)) as a conductive polymer was dissolved in methylene chloride, to prepare a solution having a POF content of 10 mg per milliliter of methylene chloride. The solution was dripped onto the ITO electrode and spin-coated onto it at 4000 rpm for 30 seconds, to form a hole-transporting and luminescent layer 2. The POF film obtained had a thickness of 50 nm.

Next, TPPO-Burst as an electron-transporting material was dissolved in methanol to prepare a solution having a TPPO-Burst content of 16 mg per milliliter of methanol. The solution was dripped onto the hole-transporting and luminescent layer of POF and spin-coated onto it at 4000 rpm for 30 seconds, to form an electron-transporting layer 3. The underlying hole-transporting and luminescent layer showed no change in thickness before and after the spin-coating, and received no damage. The electron-transporting layer obtained had a thickness of 50 nm.

Mg and Ag were co-deposited on the electron-transporting layer, to form a cathode 4 (Mg:Ag=10:1). The MgAg electrode had a thickness of 100 nm.

(4) Manufacture of an Organic Electroluminescent Element According to Comparative Example 1.

Figure 2:
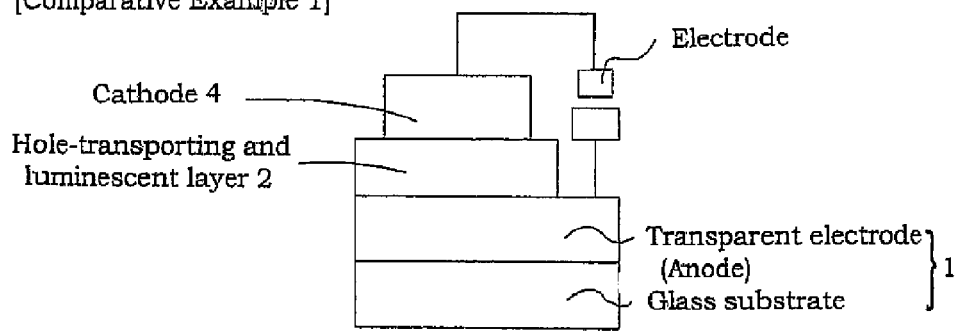
FIG. 2 is an explanatory view showing an organic electroluminescent element according to Comparative Example 1.

FIG. 2 is an explanatory view showing an organic electroluminescent element according to Comparative Example 1. The element according to Comparative Example 1 shown in FIG. 2 was manufactured in the same manner as used to obtain the element according to Example 1, except that no electron-transporting layer was formed on the hole-transporting and luminescent layer. However, in Comparative Example 1, the POF as the conductive polymer was dissolved in 16 mg per milliliter of the methylene chloride to prepare the spin-coating solution, and the POF film after the spin-coating had a thickness of 100 nm.

(5) Voltage-luminance Characteristics and Current-luminance Characteristics of the Organic Electroluminescent Elements A voltage was applied to each of the elements according to Example 1 and Comparative Example 1, to evaluate their voltage-luminance characteristics and current-luminance characteristics.

Figure 3:
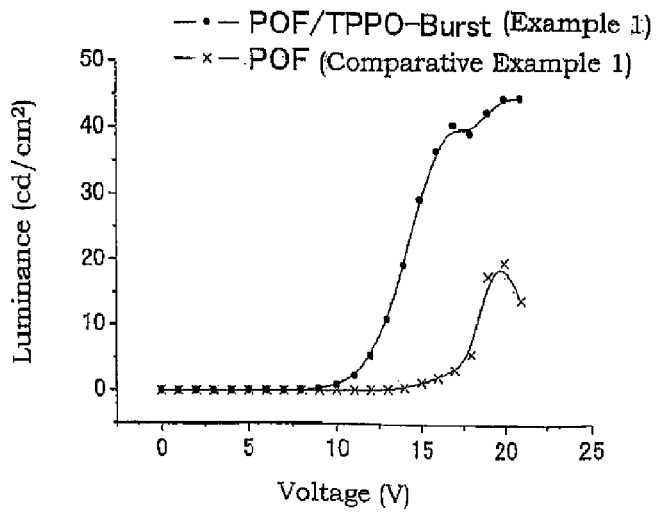
FIG. 3 is a characteristic view showing the voltage-luminance relationships of the elements according to Example 1 and Comparative Example 1.

FIG. 3 is a characteristic view showing the voltage-luminance relationships of the elements according to Example 1 and Comparative Example 1.

Figure 4:
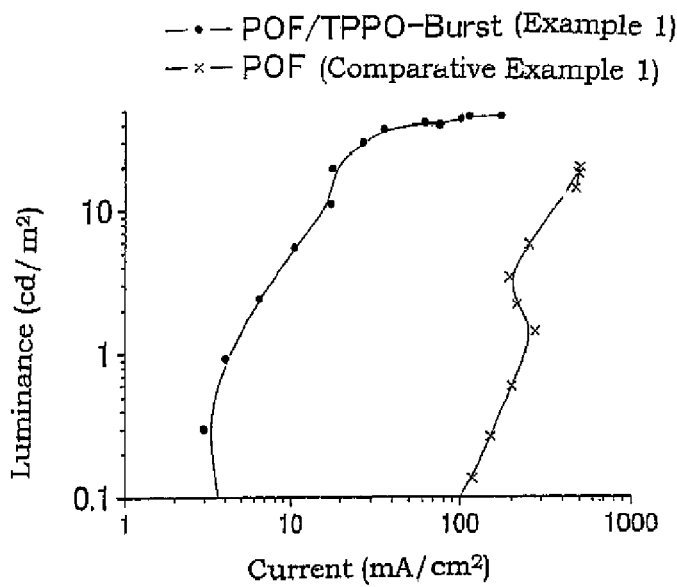
FIG. 4 is a characteristic view showing the current-luminance relationships of the elements according to Example 1 and Comparative Example 1.

FIG. 4 is a characteristic view showing the current-luminance relationships of the elements according to Example 1 and Comparative Example 1.

As seen from the voltage-luminance characteristics shown in FIG. 3, the use of the TPPO-Burst as the electron-transporting material significantly decreased the driving voltage, presumably by promoting the injection of electrons from the MgAg electrode.

Also, as seen from the current-luminance characteristics shown in FIG. 4, the use of the TPPO-Burst as the electron-transporting material significantly improved the luminance of the element in relation to the current, presumably by improving the injection balance between electrons and holes due to the exciton-confining effect of the TPPO-Burst.

EXAMPLE 2

Figure 5:
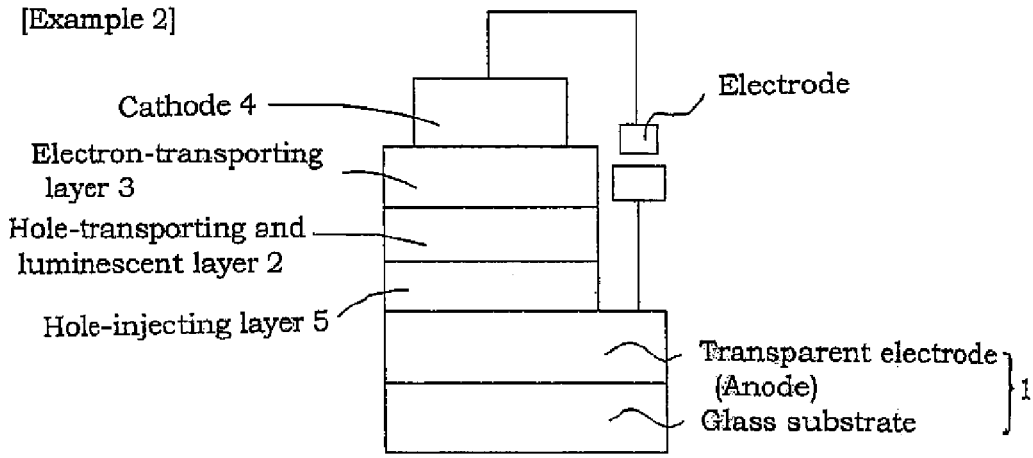
FIG. 5 is an explanatory view showing an organic electroluminescent element according to Example 2 of the present invention.

(1) Manufacture of an Organic Electroluminescent Element Having a Hole-injecting Layer FIG. 5 is an explanatory view showing an organic electroluminescent element according to Example 2 of the present invention.

The organic electroluminescent element according to Example 2 shown in FIG. 5 was manufactured in the same manner as used to obtain the element according to Example 1, except that a hole-injecting layer 5 was formed between the transparent electrode and the hole-transporting and luminescent layer. The following are details of the constitution of the organic electroluminescent element according to Example 2.

transparent electrode (ITO)/hole-injecting layer (PEDT/PSS)/hole-transporting and luminescent layer (POF)/electron-transporting layer (TPPO-Burst)/cathode (MgAg)

An aqueous solution of PEDT/PSS (polyethylene dioxythiophene/polystyrene sulfonic acid) manufactured by Bayer AG. was used as a hole-injecting material. The solution was dripped onto the transparent electrode and spin-coated onto it at 1000 rpm for 180 seconds to form the hole-injecting layer 5. Further, as in Example 1, the hole-transporting and luminescent layer, the electron-transporting layer and the cathode were sequentially laminated to manufacture the element. The hole-transporting and luminescent layer and the hole-injecting layer showed no change in thickness before and after the spin-coating conducted for the lamination of the electron-transporting layer on the hole-transporting and luminescent layer, and received no damage. This is attributable to the fact that the POF as the hole-injecting layer material and the PEDT/PSS as the luminescent layer material were insoluble in alcohols (in this Example, methanol).

(2) Manufacture of an Organic Electroluminescent Element According to Comparative Example 2

Figure 6:
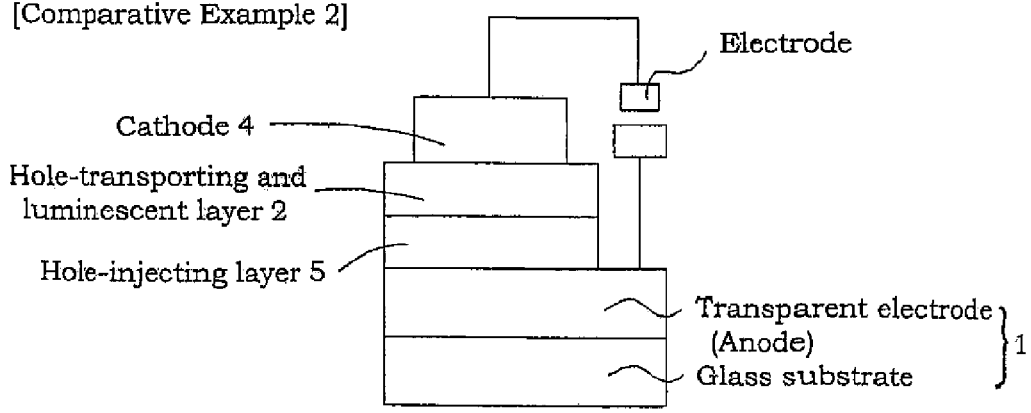
FIG. 6 is an explanatory view showing an organic electroluminescent element according to Comparative Example 2.

FIG. 6 is an explanatory view showing an organic electroluminescent element according to Comparative Example 2.

The organic electroluminescent element according to Comparative Example 2 shown in FIG. 6 was manufactured in the same manner as used to obtain the element according to Example 1, except that no electron-transporting layer was formed on the hole-transporting and luminescent layer 2.

(3) Voltage-luminance Characteristics and Current-luminance Characteristics of the Organic Electroluminescent Elements A voltage was applied to each of the elements of Example 2 and Comparative Example 2 to evaluate their voltage-luminance characteristics and current-luminance characteristics.

Figure 7:
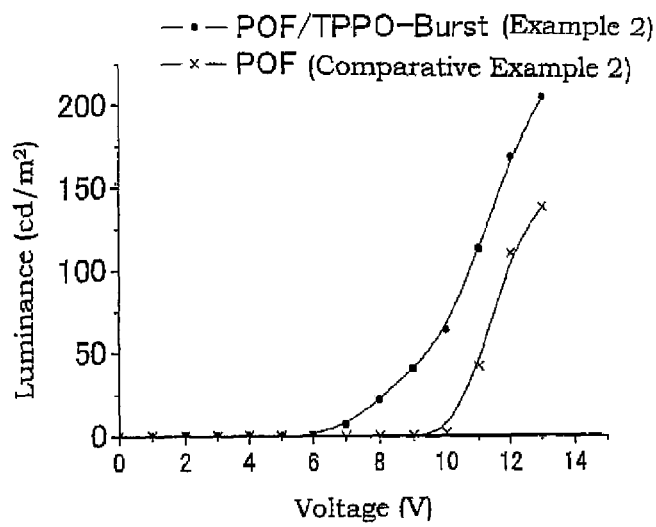
FIG. 7 is a characteristic view showing the voltage-luminance relationships of the elements according to Example 2 and Comparative Example 2.

FIG. 7 is a characteristic view showing the voltage-luminance relationships of the elements according to Example 2 and Comparative Example 2.

Figure 8:
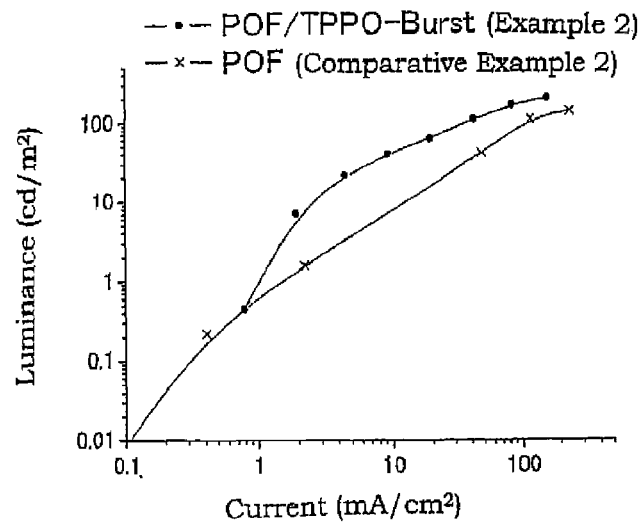
FIG. 8 is a characteristic view showing the current-luminance relationships of the elements according to Example 2 and Comparative Example 2.

FIG. 8 is a characteristic view showing the current-luminance relationships of the elements according to Example 2 and Comparative Example 2.

As seen from the voltage-luminance characteristics shown in FIG. 7, the use of TPPO-Burst as the electron-transporting material decreased the driving voltage by about 3V. Also, as seen from the current-luminance characteristics shown in FIG. 8, the elements according to Example 2 and Comparative Example 2 that had the hole-injecting layer of PEDT/PSS, unlike the element according to Example 1 that has no hole-injecting layer (see FIG. 4), were not subject to instability in current-luminance characteristics, presumably because the hole-injecting layer of PEDT/PSS increased the total thickness of the organic compound layers and as a result, prevented contact and electrical continuity between the transparent electrode (anode) and the rear electrode.

Figure 9:
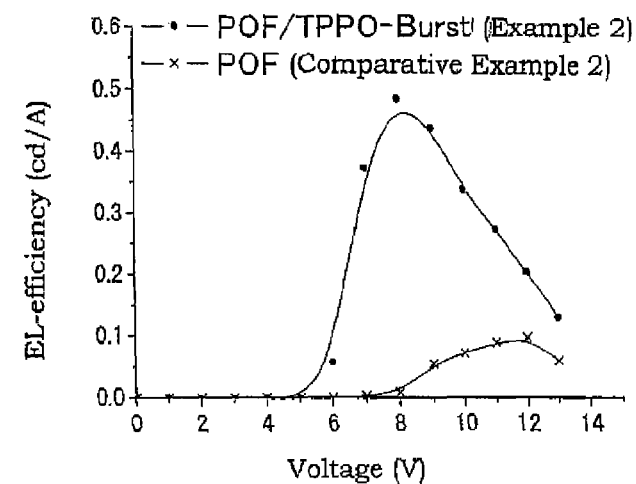
FIG. 9 is a characteristic view showing the voltage-vs.-EL-efficiency relationships of the elements according to Example 2 and Comparative Example 2.

(4) Voltage-vs.-EL-efficiency Characteristics of the Organic Electroluminescent Elements The voltage-vs.-EL-efficiency characteristics of the elements of Example 2 and Comparative Example 2 were evaluated. FIG. 9 is a characteristic view showing the voltage-vs.-EL-efficiency relationships of the elements according to Example 2 and Comparative Example 2.

As seen in FIG. 9, the lamination of the electron-transporting layer of TPPO-Burst improved the EL efficiency about fivefold.

EXAMPLE 3

(1) Manufacture of an Organic Electroluminescent Element

An organic electroluminescent element according to Example 3 was manufactured in the same manner as used to obtain the element according to Example 2 shown in FIG. 2, except that PVK (polyvinyl carbazole) and Ir(ppy)$_3$ (tris(2-phenylpyridine)iridium) were used as the materials of the hole-transporting and luminescent layer. The following are details of the constitution of the element.

transparent electrode (ITO)/hole-injecting layer (PEDT/PSS)/hole-transporting and luminescent layer (PVK: Ir(ppy)$_3$)/electron-transporting layer (TPPO-Burst)/cathode (MgAg)

The hole-transporting and luminescent layer was formed as follows. First, a predetermined amount of PVK was fed into a vial, and next, 10 parts by weight of Ir(ppy)$_3$ with respect to 100 parts by weight of the PVK were fed into it. After that, the PVK and Ir(ppy)$_3$ were dissolved in 1 ml of THF serving as a solvent to prepare a solution having a PVK content of 14 mg per milliliter of THF serving as the solvent. The solution was dripped onto the hole-injecting layer and spin-coated onto it at 4000 rpm for 30 seconds to form the hole-transporting and luminescent layer. The hole-transporting and luminescent layer had a thickness of 60 nm.

As in Example 2, the electron-transporting layer and the cathode were sequentially laminated to manufacture the element. However, the electron-transporting layer had a thickness of 60 nm. As in Example 2, the hole-transporting and luminescent layer and the hole-injecting layer showed no change in thickness before and after the spin-coating conducted for the lamination of the electron-transporting layer on the hole-transporting and luminescent layer, and received no damage.

TPPO-Burst films were formed by a wet method and a dry method and the arithmetical mean roughnesses (Ra) of their surfaces were measured as follows. Methanol, ethanol, 2-propanol, 1-propanol, 1-butanol, 2-butanol, 2-methyl-1-propanol, and 2-methyl-2-propanol were used as solvents to dissolve the TPPO-Burst. Solutions with a TPPO-Burst content of 16 mg per milliliter of each solvent were spin-coated at 4000 rpm for 30 seconds to form thin films. Some of the thin films obtained were dried at room temperature and the other at 105° C. for 1 hour. Further, as contrasts, TPPO-Burst thin films were formed by a vacuum deposition method. The surface conditions of the thin films were observed through a scanning probe microscope (SPI4000N) manufactured by Seiko Instruments Inc. and an atomic force microscope (AFM), and quantitatively evaluated using the arithmetical mean roughness (Ra) as an indicator of the surface conditions.

The surface conditions of thin films were assumed to be subject to their underlying substrates, and two types of substrates were prepared: substrates of quartz and substrates comprising a transparent electrode (ITO)/a hole-injecting layer (PEDT/PSS)/a hole-transporting and luminescent layer (PVK: Ir(ppy)$_3$). Each of the substrates comprising the transparent electrode (ITO)/the hole-injecting layer (PEDT/PSS)/the hole-transporting and luminescent layer (PVK: Ir(ppy)$_3$) was produced as follows. An aqueous solution was prepared using PEDT/PSS (polyethylenedioxythiophene/polystyrene sulfonic acid) manufactured by Bayer AG. as the hole-injecting material. The solution was dripped onto the transparent electrode and spin-coated onto it at 1000 rpm for 180 seconds to form the hole-injecting layer (PEDT/PSS). After that, the hole-transporting and luminescent layer was formed as follows. First, a predetermined amount of PVK was fed into a vial and next, 10 parts by weight of Ir(ppy)$_3$ with respect to 100 parts by weight of the PVK were fed into it. Then, the PVK and Ir(ppy)$_3$ were dissolved in 1 ml of THF serving as a solvent to prepare a solution having a PVK content of 14 mg per milliliter of THF serving as the solvent. The solution was dripped onto the hole-injecting layer and spin-coated onto it at 4000 rpm for 30 seconds to form the hole-transporting and luminescent layer.

The tables below show the arithmetical mean roughnesses (Ra) obtained, together with: the drying conditions; the underlying substrates; and the solvents to dissolve the TPPO-Burst.

TABLE 1

| Drying condition | Underlying substrate | Solvent to dissolve TPPO-Burst | Arithmetical mean roughness *1 Unit: nm |
|---|---|---|---|
| No drying by heating | Quartz substrate | Methanol | 0.35 |
| No drying by heating | Quartz substrate | Ethanol | 0.27 |
| No drying by heating | Quartz substrate | 2-propanol | 0.39 |
| No drying by heating | Quartz substrate | 1-propanol | 0.35 |
| No drying by heating | Quartz substrate | 1-butanol | 0.37 |
| No drying by heating | Quartz substrate | 2-butanol | 0.40 |
| No drying by heating | Quartz substrate | 2-methyl-1-propanol | 0.39 |
| No drying by heating | Quartz substrate | 2-methyl-2-propanol | 0.34 |
| 105° C., 1 h | Quartz substrate | Methanol | 0.65 |
| 105° C., 1 h | Quartz substrate | Ethanol | 0.79 |
| 105° C., 1 h | Quartz substrate | 2-propanol | 0.43 |
| 105° C., 1 h | Quartz substrate | 1-propanol | 0.55 |
| 105° C., 1 h | Quartz substrate | 1-butanol | 0.64 |
| 105° C., 1 h | Quartz substrate | 2-butanol | 0.61 |
| 105° C., 1 h | Quartz substrate | 2-methyl-1-propanol | 0.45 |
| 105° C., 1 h | Quartz substrate | 2-methyl-2-propanol | 0.46 |
| — | Quartz substrate | (Film is made by vacuum deposition) | 0.33 |

*1 Calculated for a length of about 15 nm on a line made in parallel to a scaning direction.

TABLE 2

| Drying condition | Underlying condition | Solvent to dissolve TPPO-Burst | Arithmethical mean roughness *1 Unit: nm |
|---|---|---|---|
| No dryng by heating | ITO/PEDOT/PVK: Ir(ppy)$_3$ | Methanol | 9.00 |
| No dryng by heating | ITO/PEDOT/PVK: Ir(ppy)$_3$ | Ethanol | 0.20 |
| No dryng by heating | ITO/PEDOT/PVK: Ir(ppy)$_3$ | 2-propanol | 0.57 |
| No dryng by heating | ITO/PEDOT/PVK: Ir(ppy)$_3$ | 1-propanol | 0.43 |
| No dryng by heating | ITO/PEDOT/PVK: Ir(ppy)$_3$ | 1-butanol | 0.52 |
| No dryng by heating | ITO/PEDOT/PVK: Ir(ppy)$_3$ | 2-butanol | 0.53 |
| No dryng by heating | ITO/PEDOT/PVK: Ir(ppy)$_3$ | 2-methyl-1-propanol | 0.58 |
| No dryng by heating | ITO/PEDOT/PVK: Ir(ppy)$_3$ | 2-methyl-2-propanol | 0.64 |
| 105° C., 1 h | ITO/PEDOT/PVK: Ir(ppy)$_3$ | Methanol | 9.18 |
| 105° C., 1 h | ITO/PEDOT/PVK: Ir(ppy)$_3$ | Ethanol | 0.18 |
| 105° C., 1 h | ITO/PEDOT/PVK: Ir(ppy)$_3$ | 2-propanol | 0.28 |
| 105° C., 1 h | ITO/PEDOT/PVK: Ir(ppy)$_3$ | 1-propanol | 0.34 |
| 105° C., 1 h | ITO/PEDOT/PVK: Ir(ppy)$_3$ | 1-butanol | 0.52 |
| 105° C., 1 h | ITO/PEDOT/PVK: Ir(ppy)$_3$ | 2-butanol | 0.47 |
| 105° C., 1 h | ITO/PEDOT/PVK: Ir(ppy)$_3$ | 2-methyl-1-propanol | 0.46 |
| 105° C., 1 h | ITO/PEDOT/PVK: Ir(ppy)$_3$ | 2-methyl-2-propanol | 0.52 |

*1 Calculated for a length of about 15 nm on a line made in parallel to a scaning direction.

Shown in the table below for reference are the properties of underlying substrate materials.

TABLE 3

| Method/material | Drying Condition | Underlying substrate | Solvent to dissolve material | Arithmetical mean roughness *1 (Unit: nm) |
|---|---|---|---|---|
| Spin coating Method/ (PEDT-PSS) | 105° C., 1 h | ITO glass | Water | 1.05 |
| Spin coating Method/ (PVK: Ir(ppy)$_3$) | 105° C., 1 h | (ITO)/(PEDT/PSS) | THF | 0.55 |

*1: Calculated for a length of about 15 nm on a line made in parallel to a scaning direction.

As shown in Table 1, the surfaces of the thin films formed on the quartz substrates by spin-coating the TPPO-Burst solutions in the alcohols had arithmetical mean roughnesses Ra of 1 nm or less, indicating that the surfaces of these films were smooth enough to permit manufacture of organic electroluminescent elements.

Table 2 shows the arithmetical mean roughnesses Ra of the thin films formed by spin-coating the TPPO-Burst solutions in the alcohols on the film of conductive polymer PVK: Ir(ppy)$_3$ which was actually used as the hole-transporting and luminescent layer of the organic electroluminescent element. It was noted that the Ra were 10 nm or less, indicating that the surfaces of the thin films were smooth enough to permit manufacture of organic electroluminescent elements. Also, it is noted that while the surfaces of thin films formed by spin-coating solutions in methanol had Ra of about 9 nm, the surfaces of the other thin films formed by spin-coating solutions in the other solvents had an Ra of 0.7 nm or less, about an order of magnitude smaller. This indicates that the solvents other than methanol are more suitable for spin-coating than methanol.

(3) Manufacture of an Organic Electroluminescent Element According to Comparative Example 3

An element according to Comparative Example 3 was manufactured in the same manner as used to obtain the element according to Example 3, except that no electron-transporting layer was formed on the hole-transporting and luminescent layer. It is to be noted that the hole-transporting and luminescent layer was formed on the hole-injecting layer by spin-coating at 2000 rpm for 30 seconds the same PVK: Ir(ppy)₃ solution in THF as used in Example 3. The hole-transporting and luminescent layer had a thickness of 90 nm.

(4) Voltage-luminance Characteristics and Current-luminance Characteristics of the Organic Electroluminescent Elements A voltage was applied to each of the elements of Example 3 and Comparative Example 3 to evaluate their voltage-luminance characteristics and current-luminance characteristics.

Figure 10:
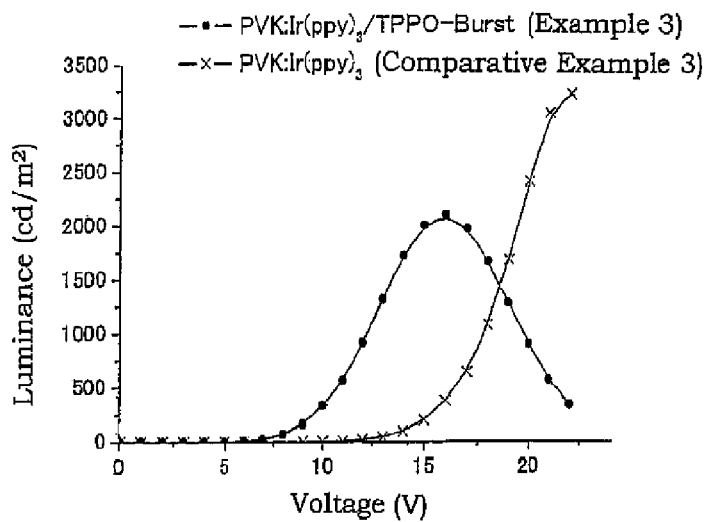
FIG. 10 is a characteristic view showing the voltage-luminance relationships of the elements according to Example 3 and Comparative Example 3.

FIG. 10 is a characteristic view showing the voltage-luminance relationships of the elements according to Example 3 and Comparative Example 3.

Figure 11:
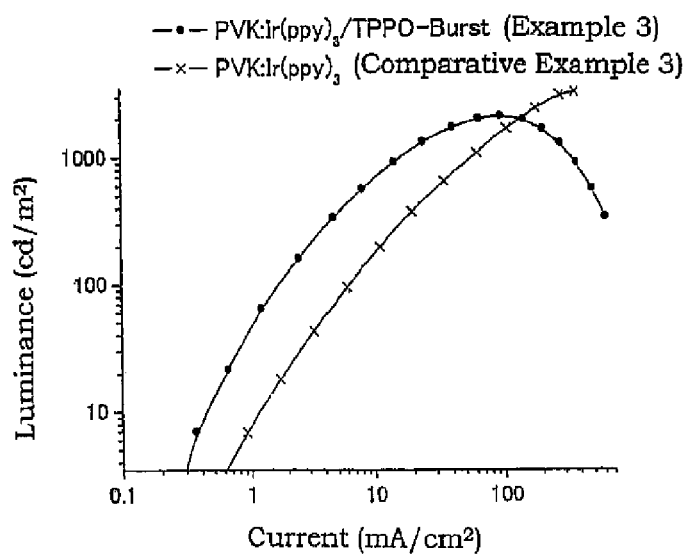
FIG. 11 is a characteristic view showing the current-luminance relationships of the elements according to Example 3 and Comparative Example 3.

FIG. 11 is a characteristic view showing the current-luminance relationships of the elements according to Example 3 and Comparative Example 3.

As seen from the voltage-luminance characteristics shown in FIG. 10, the use of the TPPO-Burst as the electron-transporting material decreased the driving voltage by about 6 V. Also, as seen from the current-luminance characteristics shown in FIG. 11, the use of the TPPO-Burst improved the luminance of the element in relation to the current.

Figure 12:
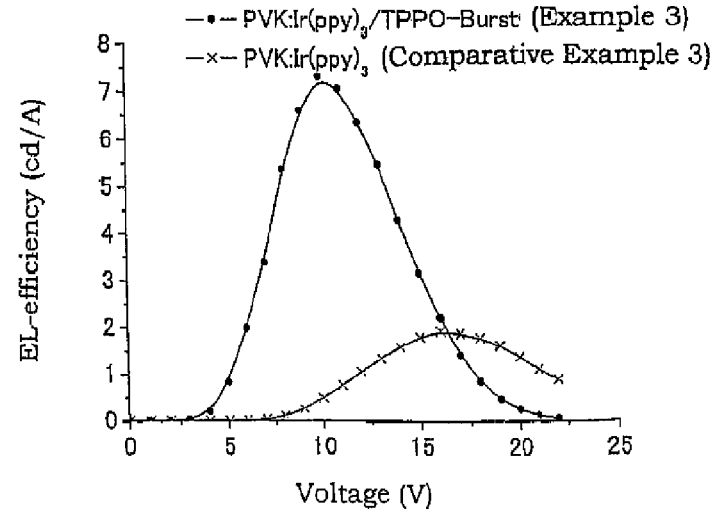
FIG. 12 is a characteristic view showing the voltage-vs.-EL-efficiency relationships of the elements according to Example 3 and Comparative Example 3.

(5) Voltage-vs.-EL-efficiency Characteristics of the Organic Electroluminescent Elements The voltage-vs.-EL-efficiency characteristics of the elements according to Example 3 and Comparative Example 3 were evaluated. FIG. 12 is a characteristic view showing the voltage-vs.-EL-efficiency relationships of the elements according to Example 3 and Comparative Example 3.

As seen in FIG. 12, the lamination of the TPPO-Burst as the electron-transporting layer improved the EL efficiency about 3.8-fold.

EXAMPLE 4

Synthesis of 4,4'-bis(diphenylphosphinyl)-triphenylphosphine oxide [TPPO-Trimer]

TPPO-Trimer was synthesized as shown in the following reaction scheme. First, phosphine oxide (intermediate) was synthesized and then, from this intermediate, the TPPO-Trimer was synthesized.

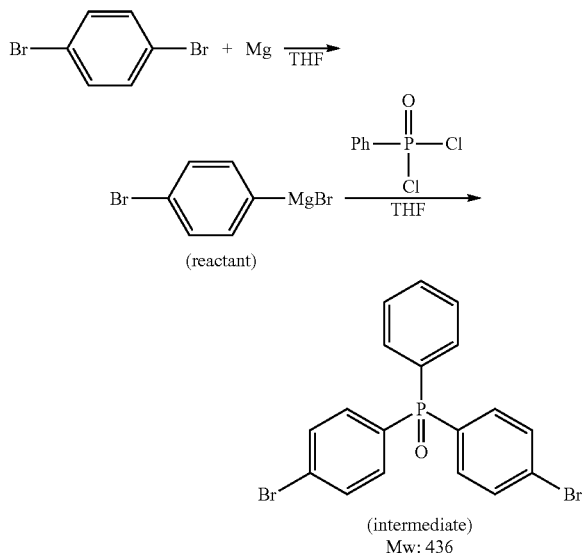

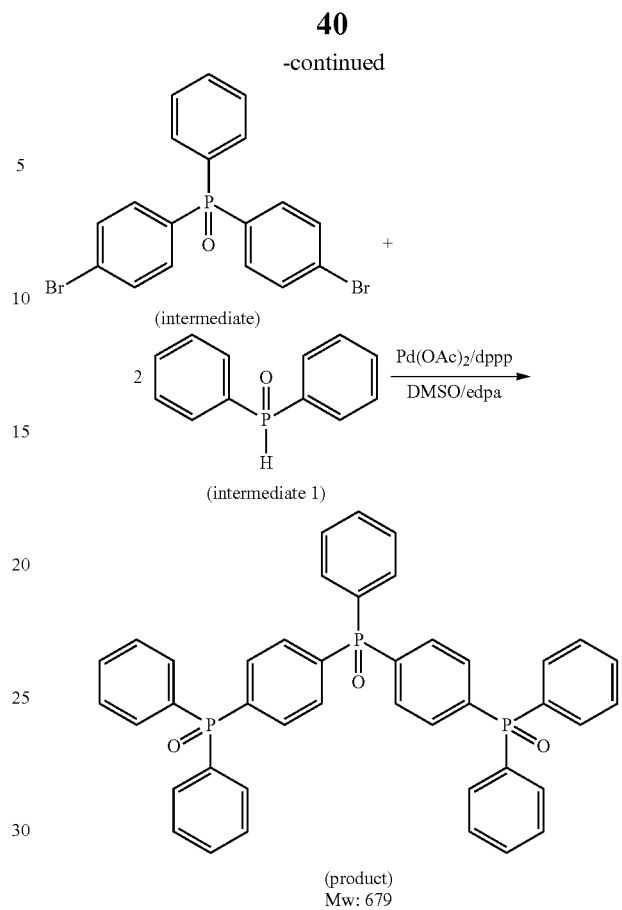

(Synthesis of the Intermediate)

A solution of 29.3 g (124 mmol) of 1,4-dibromobenzene in absolute tetrahydrofuran (hereafter, referred to as THF) was dripped onto 2.54 g (105 mmol) of a magnesium metal piece in an atmosphere of nitrogen, to prepare a Grignard reagent (reactant 7b). To the solution, a solution of 6.99 g (35.9 mmol) of dichlorophenylphosphine oxide in absolute diethyl ether was slowly dropwise added. After completion of the addition, the resulting solution was stirred overnight. To the solution, 14 ml of a hydrochloric acid solution (concentration 36%) was added dropwise. The target compound was extracted with distilled water/chloroform from the solution, and the chloroform phase was separated, and concentrated by a rotary evaporator. The remaining viscous liquid was dissolved in a small amount of chloroform, and the resulting solution was subjected to column chromatography that used silica gel as a filler, to separate the target compound. After the separation, the target compound was recrystallized from cyclohexane. The crystals obtained were subjected to FAB mass analysis, whereby it was confirmed that (molecular weight)=436, (molecular weight)+2=438, and (molecular weight)+4=440 and that the crystals obtained were the target intermediate (yield 4.93 g (11.30 mmol), 31.6%).

Synthesis from the Intermediate

The intermediate of 2.42 g (5.55 mmol) was reacted with 4.48 g (22.1 mmol) of diphenylphosphine oxide serving as an intermediate 1, in 55.6 ml of dimethyl sulfoxide (hereafter, referred to as DMSO) serving as a solvent at 100° C. in the presence of 250 mg (1.11 mol) of palladium acetate (hereafter, referred to as Pd(OAc)₂), 688 mg (1.67 mmol) of 1,3-bis (diphenylphosphino) propane (hereafter, referred to as dppp), and 10 ml of N-ethyldiisopropylamine (edpa). The target compound was extracted with distilled water/chloroform from the solution and concentrated. The remaining viscous liquid was dissolved in a small amount of chloroform, and the resulting solution was subjected to column chromatography that used silica gel as a filler, to separate the target compound. The target compound was recrystallized, and purified by sublimation in a vacuum at 330-340° C., to obtain a white crystal. The crystals obtained were subjected to FAB mass analysis, whereby it was confirmed that (molecular weight)=679 and that the crystals obtained were the target TPPO-Trimer (yield 2.12 g (3.12 mmol), 56%, Tm: 346° C., Tg: 105° C.).

EXAMPLE 5

Synthesis of 4,4',4''-tris-(di-p-tolyl-phosphinyl)-triphenylphosphine oxide [TPPO-(p-CH₃) Burst]

TPPO-(p-CH₃) Burst was synthesized as shown in the following reaction scheme. First, di-p-tolyl-phosphine oxide(intermediate a) was synthesized, and then from this intermediate a and the intermediate b, the TPPO-(p-CH₃) Burst was synthesized.

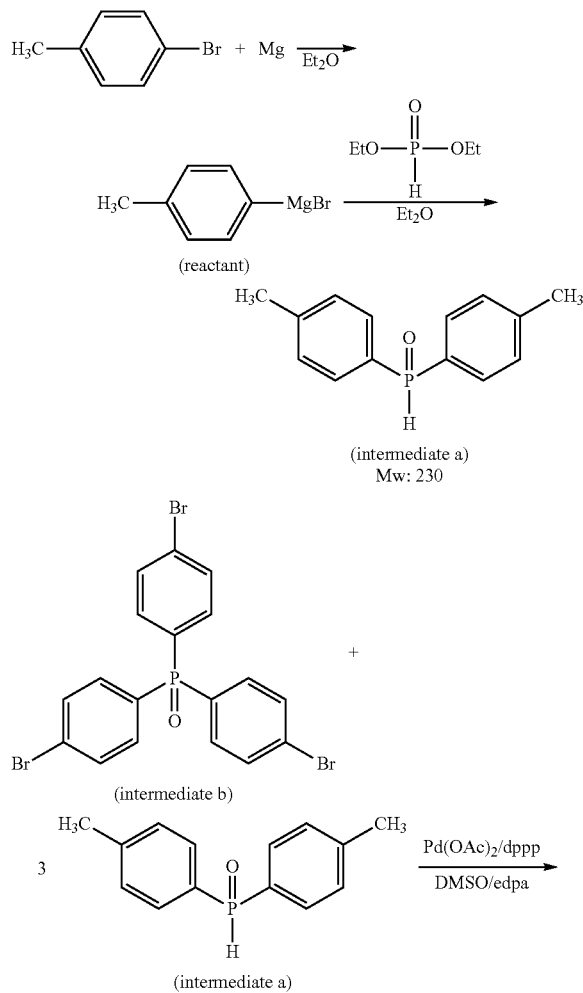

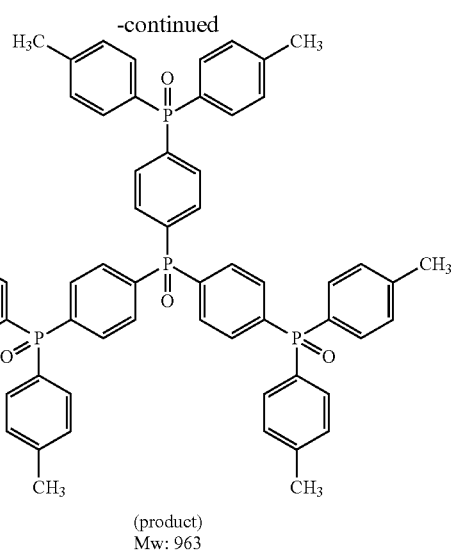

(product)
Mw: 963

Synthesis of the Intermediate a

A solution of 25 g (145.9 mmol) of p-bromotoluene in absolute diethyl ether was dripped onto 3.0 g (123.5 mmol) of a magnesium metal piece in an atmosphere of nitrogen, to prepare a Grignard reagent (reactant). To the solution, a solution of 8.64 g (62.59 mmol) of diethylphosphite in absolute diethyl ether was slowly dropwise added. After completion of the addition, the resulting solution was stirred overnight. To the solution, 14 ml of a hydrochloric acid solution (concentration 36%) was added dropwise. The target compound was extracted with distilled water/chloroform from the solution, and the chloroform phase was separated, and concentrated by a rotary evaporator. The remaining viscous liquid was dissolved in a small amount of chloroform, and the resulting solution was subjected to column chromatography that used silica gel as a filler, to separate the target compound. After the separation, the target compound was recrystallized from diethyl ether. The crystals obtained were subjected to FAB mass analysis, whereby it was confirmed that (molecular weight)+1=231 and that the crystals obtained were the target intermediate a (yield 5.76 g (25.02 mmol),40%)

Synthesis from the Intermediates a and b

The intermediate a of 2.88 g (12.51 mmol) was reacted with 1.07 g (2.08 mmol) of triphenylphosphine oxide serving as the intermediate b, in 20.8 ml of DMSO serving as a solvent at 100° C. in the presence of 93.3 mg (0.416 mmol) of Pd(OAc)₂, 257 mg (0.624 mmol) of dppp, and 3.7 ml of edpa. The target compound was extracted with distilled water/chloroform from the solution and concentrated. The remaining viscous liquid was dissolved in a small amount of chloroform, and the resulting solution was subjected to column chromatography that used silica gel as a filler, to separate the target compound. After the separation, the target compound was recrystallized from methanol/toluene, to obtain a white crystal. The crystals obtained were subjected to FAB mass analysis, whereby it was confirmed that (molecular weight)=963 and that the crystals obtained were the target TPPO-(p-CH₃) Burst (yield 1.17 g (1.22 mmol), 59%, Tm:335° C., Tg:133° C.).

EXAMPLE 6

Synthesis of 4,4',4''-tris-(di-o-tolyl-phosphinyl)-triphenylphosphine oxide[TPPO-(o-CH₃)Burst]

TPPO-(o-CH₃)Burst was synthesized as shown in the following reaction scheme. First, di-o-tolyl-phosphine oxide (intermediate a) was synthesized, and then from this intermediate a and the intermediate b, the TPPO-(o-CH₃)Burst was synthesized.

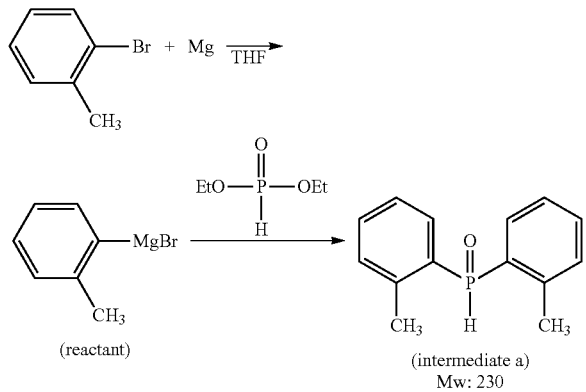

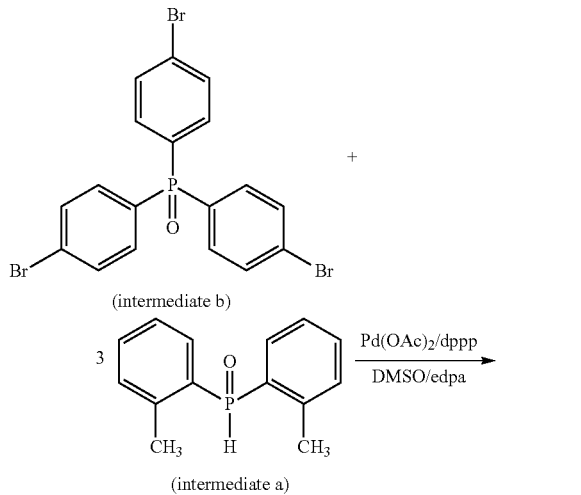

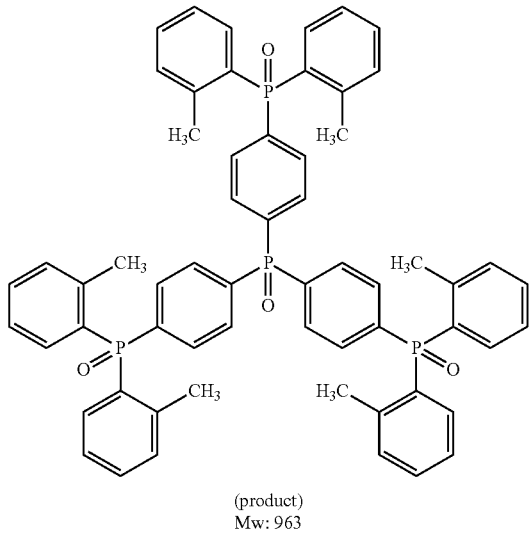

Synthesis of the Intermediate a

A solution of 25 g (145.9 mmol) of o-bromotoluene in absolute diethyl ether is dripped onto 3.0 g (123.5 mmol) of a magnesium metal piece in an atmosphere of nitrogen, to prepare a Grignard reagent (reactant). To the solution, a solution of 8.64 g (62.59 mmol) of diethylphosphite in absolute diethyl ether was slowly dropwise added. After completion of the addition, the resulting solution was stirred overnight. To the solution, 14 ml of hydrochloric acid solution (concentration 36%) was added dropwise. The target compound was extracted with distilled water/chloroform from the solution, and the chloroform phase was separated, and concentrated by a rotary evaporator. The remaining viscous liquid was dissolved in a small amount of chloroform, and the resulting solution was subjected to column chromatography that used silica gel as a filler, to separate the target compound. After the separation, the target compound was recrystallized from diethyl ether. The crystals obtained were subjected to FAB mass analysis, whereby it was confirmed that (molecular weight)+1=231 and that the crystals obtained were the target intermediate a (yield 6.67 g (29.0 mmol), 46%).

Synthesis from the Intermediates a and b

The intermediate a of 2.89 g (12.6 mmol) was reacted with 1.07 g (2.08 mmol) of triphenylphosphine oxide serving as the intermediate b, in 20.8 ml of DMSO serving as a solvent at 100° C. in the presence of 93.3 mg (0.416 mmol) of Pd(OAc)₂, 257 mg (0.624 mmol) of dppp, and 3.7 ml of edpa. The target compound was extracted with distilled water/chloroform from the solution and concentrated. The remaining viscous liquid was dissolved in a small amount of chloroform, and the resulting solution was subjected to column chromatography that used silica gel as a filler, to separate the target compound. After the separation, the target compound was recrystallized. The crystals obtained were subjected to FAB mass analysis, whereby it was confirmed that (molecular weight)=963, and that the crystals obtained were the target TPPO-(o-CH₃)Burst (yield 1.50 g (1.56 mmol), 75%, Tm: 310° C., Tg:133° C.).

EXAMPLE 7

Synthesis of 4,4',4''-tris-(di-m-tolyl-phosphinyl)-triphenylphosphine oxide[TPPO-(m-CH₃)Burst]

TPPO-(m-CH₃)Burst was synthesized as shown in the following reaction scheme. First, di-m-tolyl-phosphine oxide (inter mediate a) was synthesized, and then from the intermediate a and the intermediate b, the TPPO-(m-CH₃)Burst was synthesized.

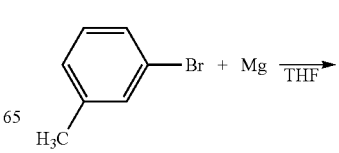

45
-continued

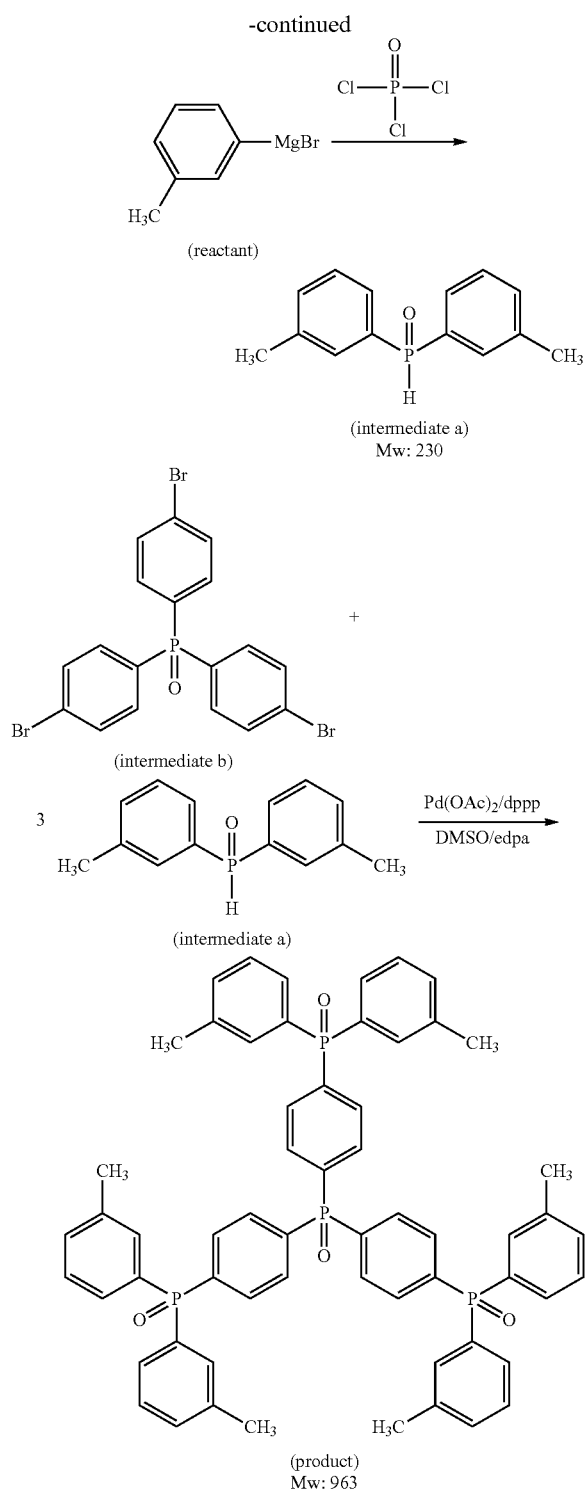

Synthesis of the Intermediate a

A solution of 12.5 g (72.9 mmol) of m-bromotoluene in absolute diethyl ether was dripped onto 1.63 g (67.1 mmol) of a magnesium metal piece in an atmosphere of nitrogen, to prepare a Grignard reagent (reactant). To the solution, a solution of 5.96 g (38.90 mmol) of phosphoryl chloride in absolute THF was slowly dropwise added. After completion of the addition, the resulting solution was stirred overnight. To the solution, 30 ml of a hydrochloric acid solution (concentration 36%) was added dropwise. The target compound was extracted with distilled water/chloroform from the solution, and the chloroform phase was separated, and concentrated by a rotary evaporator. The remaining viscous liquid was dissolved in a small amount of chloroform, and the resulting solution was subjected to column chromatography that used silica gel as a filler, to separate the target compound. After the separation, the target compound was recrystallized from diethyl ether. The crystals obtained were subjected to FAB mass analysis, whereby it was confirmed that (molecular weight)+1=231 and that the crystals obtained were the target intermediate a (yield 4.13 g (17.9 mmol), 56%).

Synthesis from the Intermediates a and b

The intermediate a of 2.90 g (12.6 mmol) was reacted with 1.10 g (2.14 mmol) of triphenylphosphine oxide as the intermediate b, in 21.0 ml of DMSO serving as a solvent at 100° C. in the presence of 93 mg (0.42 mmol) of Pd(OAc)$_2$, 260 mg (0.63 mmol) of dppp, and 4 ml of edpa. The target compound was extracted with distilled water/chloroform from the solution and concentrated. The remaining viscous liquid was dissolved in a small amount of chloroform, and the resulting solution was subjected to column chromatography that used silica gel as a filler, to separate the target compound. After the separation, the target compound was recrystallized from methanol/toluene to obtain a white crystal. The crystals obtained were subjected to FAB mass analysis, whereby it was confirmed that (molecular weight)=963, and that the crystals obtained were the target TPPO-(m-CH$_3$)Burst (yield 1.32 g (1.37 mmol), 64%).

EXAMPLE 8

Synthesis of 4,4',4''-tris-(bis-(4-methoxy-phenyl)-phosphinyl)-triphenylphosphine oxide[TPPO-(p-OCH$_3$)Burst]

TPPO-(p-OCH$_3$)Burst was synthesized as shown in the following reaction scheme. First, di(4-methoxy-phenyl) phosphine oxide (intermediate a) was synthesized, and then from the intermediate and the intermediate b, the TPPO-(p-OCH$_3$)Burst (product) was synthesized.

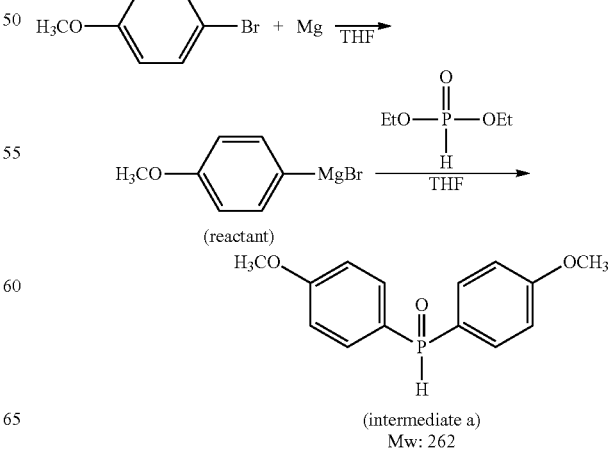

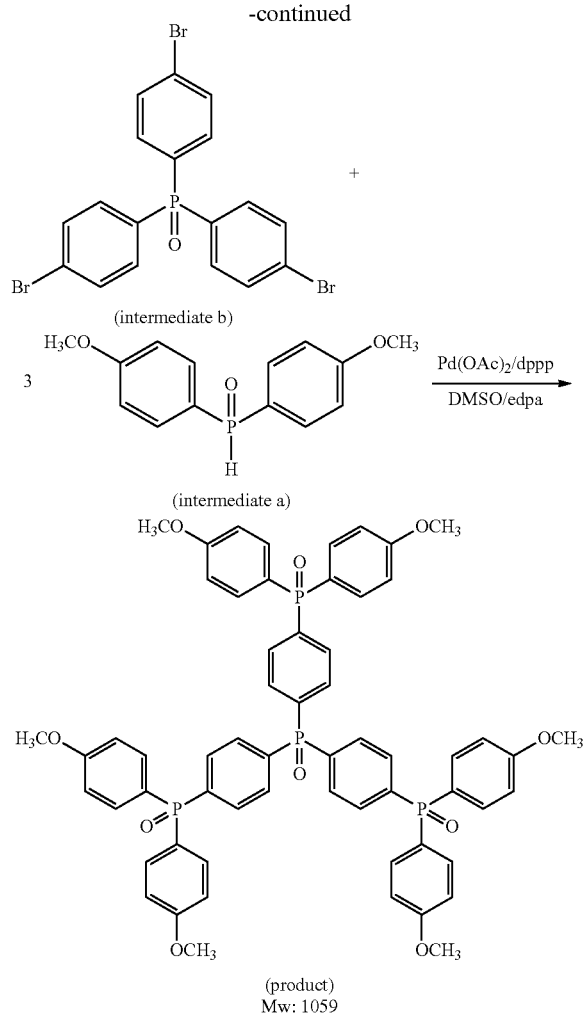

(intermediate b)

(intermediate a)

(product) Mw: 1059

Synthesis of the Intermediate a

A solution of 25.0 g (134 mmol) of p-bromoanisole in absolute THF was dripped onto 2.92 g (120.2 mmol) of a magnesium metal piece in an atmosphere of nitrogen, to prepare a Grignard reagent (reactant). To the solution, a solution of 8.69 g (60.3 mmol) of diethylphosphite in absolute THF was slowly dropwise added. After completion of the addition, the resulting solution was stirred overnight. To the solution, a 14 ml of a hydrochloric acid solution (concentration 36%) was added dropwise. The target compound was extracted with distilled water/chloroform from the solution, and the chloroform phase was separated, and concentrated by a rotary evaporator. The remaining viscous liquid was dissolved in a small amount of chloroform, and the resulting solution was subjected to column chromatography that used silica gel as a filler, to separate the target compound. After the separation, the target compound was recrystallized from cyclohexane. The crystals obtained were subjected to FAB mass analysis, whereby it was confirmed that (molecular weight)+1=263, and that the crystals obtained were the target inter mediate (yield 8.20 g (31.3 mmol), 52%).

Synthesis from the Intermediates a and b

The intermediate a of 3.30 g (12.6 mmol) was reacted with 1.07 g (2.08 mmol) of triphenylphosphine oxide as the intermediate b, in 20.8 ml of DMSO serving as a solvent at 100° C. in the presence of 93.3 mg (0.624 mmol) of Pd(OAc)$_2$, 257 mg (0.416 mmol) of dppp, and 3.7 ml of edpa. The target compound was extracted with chloroform/distilled water from the solution, and the chloroform phase was separated and concentrated. The remaining viscous liquid was dissolved in a small amount of chloroform, and the resulting solution was subjected to column chromatography that used silica gel as a filler, to separate the target compound. After the separation, the target compound was recrystallized from methanol/toluene to obtain a white crystal. The crystals obtained were subjected to FAB mass analysis, whereby it was confirmed that (molecular weight)=1059, and that the crystals obtained were the target TPPO-(p-OCH$_3$)Burst (yield 1.56 g (1.47 mmol), 71%, Tm: 378° C., Tg: 127° C.).

EXAMPLE 9

Synthesis of 4,4',4''-tris-(bis-(2-methoxy-phenyl)-phosphinyl)-triphenylphosphine oxide[TPPO-(o-OCH$_3$)Burst]

TPPO-(o-OCH$_3$)Burst was synthesized as shown in the following reaction scheme. First, di(2-methoxy-phenyl) phosphine oxide (intermediate a) was synthesized, and then from the intermediate a and the intermediate b, the TPPO-(o-OCH$_3$)Burst was synthesized.

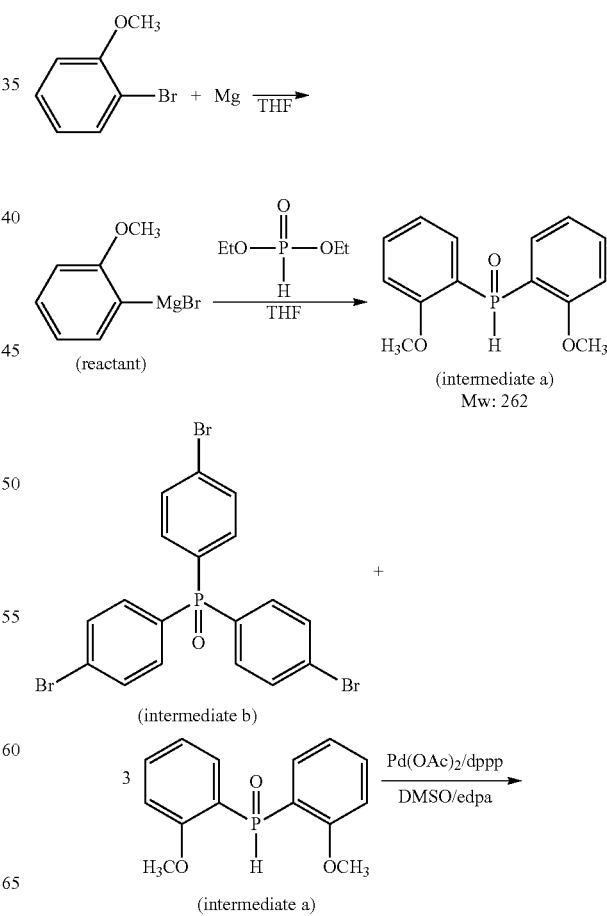

-continued

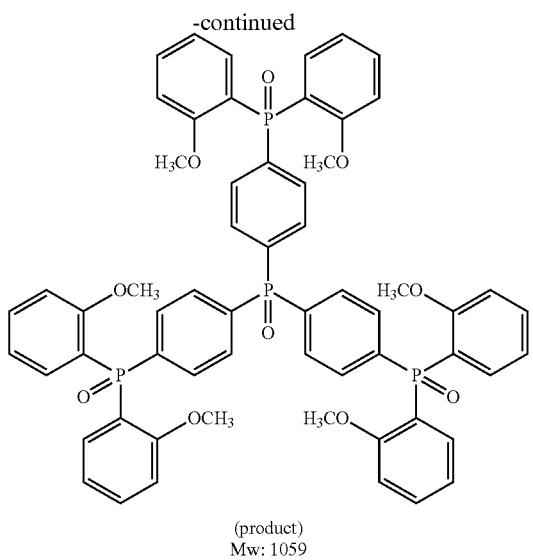

(product)
Mw: 1059

Synthesis of the Intermediate a

A solution of 12.5 g (66.8 mmol) of o-bromoanisole in absolute THF was dripped onto 1.51 g (62.1 mmol) of a magnesium metal piece in an atmosphere of nitrogen, to prepare a Grignard reagent (reactant). To the solution, a solution of 4.43 g (32.1 mmol) of diethylphosphite in absolute THF was slowly dropwise added. After completion of the addition, the resulting solution was stirred overnight. To the solution, 8 ml of a hydrochloric acid solution (concentration 36%) was added dropwise. The target compound was extracted with distilled water/chloroform from the solution, and the chloroform phase was separated, and concentrated by a rotary evaporator. The remaining viscous liquid was dissolved in a small amount of chloroform, and the resulting solution was subjected to column chromatography that used silica gel as a filler, to separate the target compound. After the separation, the target compound was recrystallized from cyclohexane. The crystals obtained were subjected to FAB mass analysis, whereby it was confirmed that (molecular weight)+1=263, and that the crystals obtained were the target intermediate (yield 4.38 g (16.7 mmol), 52%).

Synthesis from the Intermediates a and b

The intermediate a of 2.00 g (7.63 mmol) was reacted with 0.655 g (1.27 mmol) of triphenylphosphine oxide as the intermediate b, in 13.0 ml of DMSO serving as a solvent at 100° C. in the presence of 57.2 mg (0.254 mmol) of Pd(OAc)$_2$, 157 mg (0.381 mmol) of dppp, and 2.3 ml of edpa. The target compound was extracted with chloroform/distilled water from the solution, and the chloroform phase was separated and concentrated. The remaining viscous liquid was dissolved in a small amount of chloroform, and the resulting solution was subjected to column chromatography that used silica gel as a filler, to separate the target compound. After the separation, the target compound was recrystallized from methanol/toluene to obtain a white crystal. The crystals obtained were subjected to FAB mass analysis, whereby it was confirmed that (molecular weight)=1059, and that the crystals obtained were the target TPPO-(o-OCH$_3$)Burst (yield 0.80 g (0.755 mmol), 56%).

EXAMPLE 10

Synthesis of tris-(4'-diphenylphosphinyl-biphenyl-4-yl)-phosphine oxide [TBPO-(DPPO)Burst]

TBPO-(DPPO)Burst was synthesized as shown in the following reaction scheme. First, phosphine oxide (intermediate a) was synthesized, and then from the intermediate a, the TBPO-(DPPO)Burst was synthesized.

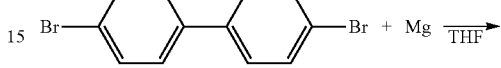

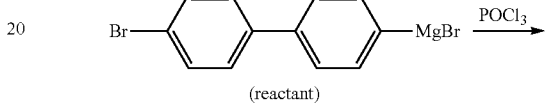

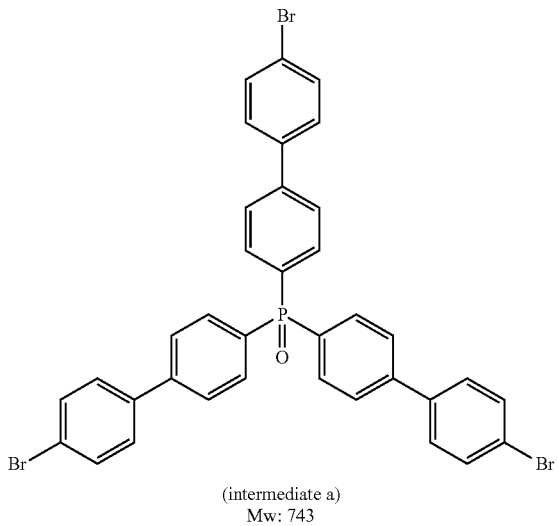

(intermediate a)
Mw: 743

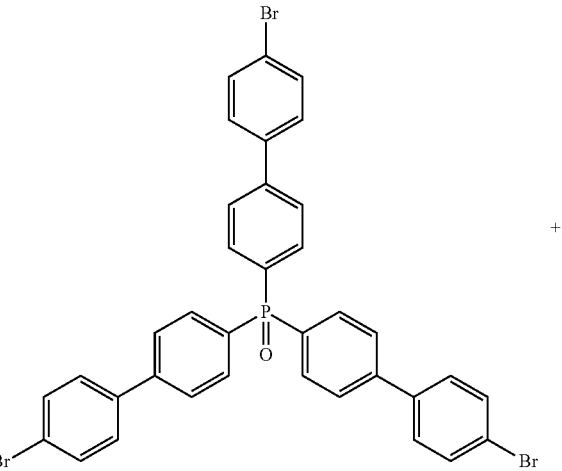

(intermediate a)

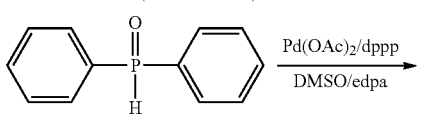

-continued

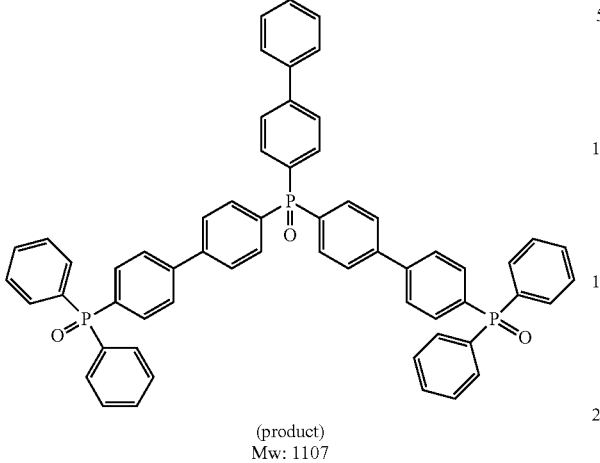

(product)
Mw: 1107

Synthesis of the Intermediate a

A solution of 74.9 g (240 mmol) of 4,4'-dibromobiphenyl in absolute THF was dripped onto 4.8 g (197.5 mmol) of a magnesium metal piece in an atmosphere of nitrogen, to prepare a Grignard reagent (reactant). To the solution, a solution of 10.2 g (66.6 mmol) of phosphoryl chloride (reactant) in absolute THF was slowly dropwise added. After completion of the addition, the resulting solution was stirred overnight. To the solution, 50 nil of a hydrochloric acid solution (concentration 36%) was added dropwise. The target compound was extracted with distilled water/chloroform from the solution, and the chloroform phase was separated, and concentrated by a rotary evaporator. The remaining viscous liquid was dissolved in a small amount of chloroform, and the resulting solution was subjected to column chromatography that used silica gel as a filler, to separate the target compound. After the separation, the target compound was recrystallized from cyclohexane. The crystals obtained were subjected to FAB mass analysis, whereby it was confirmed that (molecular weight)=743, (molecular weight)+2=745, and (molecular weight)+4=747, and that the crystals obtained were the target intermediate a (yield 38.1 g (51.3 mmol), 77%).

Synthesis from the Intermediate a

The intermediate a of 0.6 g (1.16 mmol) was reacted with 1.4 g (6.69 mmol) of diphenylphosphine oxide, in 11.6 ml DMSO serving as a solvent at 100° C. in the presence of 52.4 mg (0.233 mmol) of Pd(OAc)$_2$, 144 mg (0.349 mmol) of dppp, and 2.1 ml of edpa. The target compound was extracted with distilled water/chloroform from the solution and concentrated. The remaining viscous liquid was dissolved in a small amount of chloroform, and the resulting solution was subjected to column chromatography that used silica gel as a filler, to separate the target compound. After the separation, the target compound was recrystallized from methanol/toluene. The crystals obtained were subjected to FAB mass analysis, whereby it was confirmed that (molecular weight)=1107, and that the crystals obtained were the tar tTBPO-(DPPO) Burst (yield 0.618 g (0.70 mmol), 61%).

EXAMPLE 11

Synthesis of 4,4',4"-tris-(1-naphthyl-phenyl-phosphinyl)-triphenylphosphine oxide[TPPO-(α-NPPO) Burst]

TPPO-(α-NPPO)Burst was synthesized as shown in the following reaction scheme. First, 1-naphthyl-phenyl-phosphine oxide (intermediate a) was synthesized, and the from the intermediate a and the intermediate b, the TPPO-(α-NPPO)Burst was synthesized.

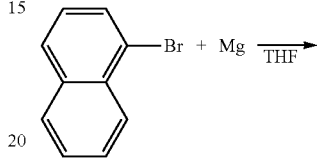

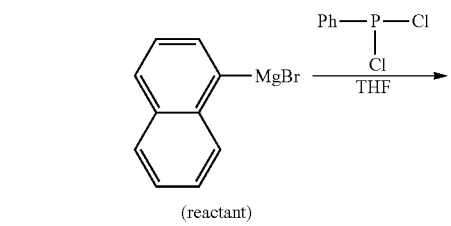

(reactant)

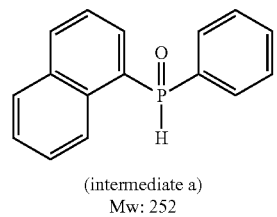

(intermediate a)
Mw: 252

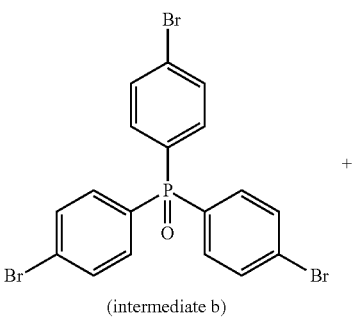

(intermediate b)

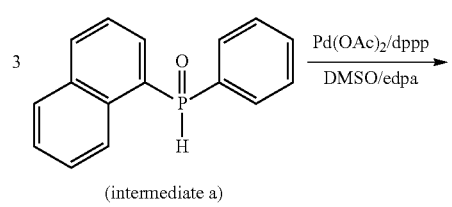

(intermediate a)

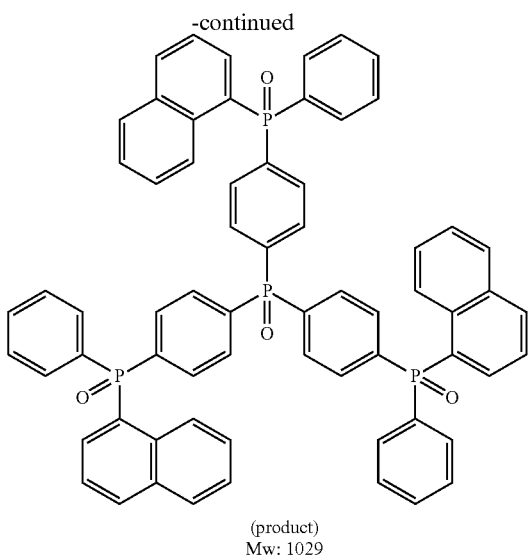

(product)
Mw: 1029

Synthesis of the Intermediate a

A solution of 28.35 g (137 mmol) of 1-bromonaphthalene in absolute THF was dripped onto 3.15 g (129.6 mmol) of a magnesium metal piece in an atmosphere of nitrogen, to prepare a Grignard reagent (reactant). To the solution, a solution of 26.0 g (145 mmol) of dichlorophenylphosphine in absolute THF was slowly dropwise added. After completion of the addition, the resulting solution was stirred overnight. To the solution, 21 ml of a hydrochloric acid solution (concentration 36%) was added dropwise. The target compound was extracted with distilled water/chloroform from the solution, and the chloroform phase was separated, and concentrated by a rotary evaporator. The remaining viscous liquid was dissolved in a small amount of chloroform, and the resulting solution was subjected to column chromatography that used silica gel as a filler, to separate the target compound. After the separation, the target compound was recrystallized from cyclohexane. The crystals obtained were subjected to FAB mass analysis, whereby it was confirmed that (molecular weight)+1=253, and that the crystals obtained were the target intermediate (yield 12.7 g (50.3 mmol), 36%).

Synthesis from the Intermediates a and b

The intermediate a of 4.03 g (16.0 mmol) was reacted with 1.17 g (2.28 mmol) of triphenylphosphine oxide as the intermediate b, in 22.8 ml of DMSO serving as a solvent at 100° C. in the presence of 144 mg (0.643 mmol) of $Pd(OAc)_2$, 377 mg (0.915 mmol) of dppp, and 4.2 ml of edpa. The target compound was extracted with chloroform/distilled water from the solution, and the chloroform phase was separated and concentrated. The remaining viscous liquid was dissolved in a small amount of chloroform, and the resulting solution was subjected to column chromatography that used silica gel as a filler, to separate the target compound. After the separation, the target compound was recrystallized from cyclohexane/toluene, to obtain a white crystal. The crystals obtained were subjected to FAB mass analysis, whereby it was confirmed that (molecular weight)=1029, and that the crystals obtained were the target TPPO-(α-NPPO)Burst (yield 1.75 g (1.70 mmol), 75%).

EXAMPLE 12

Synthesis of 4,4',4''-tris-(di-1-naphthyl-phosphinyl)-triphenylphosphine oxide[TPPO-(α-DNPO)Burst]

TPPO-(α-DNPO)Burst was synthesized as shown in the following reaction scheme. First, di-1-naphthylphosphine oxide(intermediate a) was synthesized, and then from the intermediate a and the intermediate b, TPPO-(α-DNPO)Burst was synthesized.

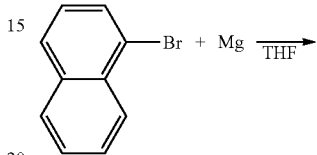

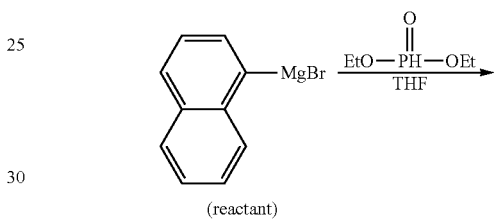

(reactant)

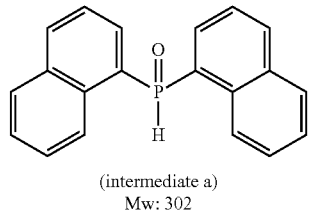

(intermediate a)
Mw: 302

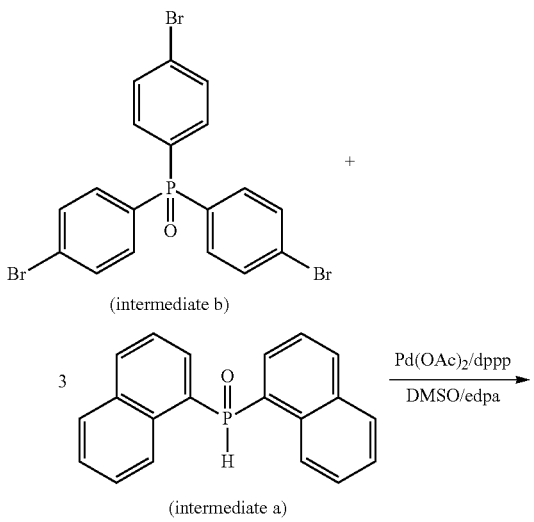

55

-continued

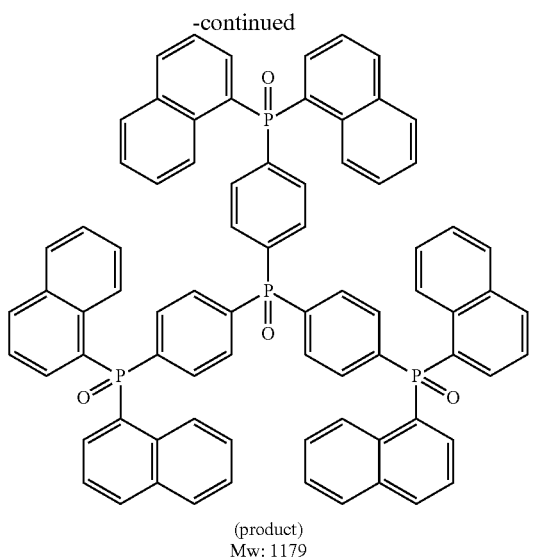

(product)
Mw: 1179

Synthesis of the Intermediate a

A solution of 114 g (551 mmol) of 1-bromonaphthalene in absolute THF was dripped onto 12.6 g (519 mmol) of a magnesium metal piece in an atmosphere of nitrogen, to prepare a Grignard reagent (reactant). To the solution, a solution of 34.0 g (246 mmol) of diethylphosphite in absolute THF was slowly dropwise added. After completion of the addition, the resulting solution was heated under reflux overnight. To the solution, 200 ml of a hydrochloric acid solution (concentration 18%) was added dropwise. The target compound was extracted with distilled water/chloroform from the solution, and the chloroform phase was separated, and concentrated by a rotary evaporator. The remaining viscous liquid was dissolved in a small amount of chloroform, and the resulting solution was subjected to column chromatography that used silica gel as a filler, to separate the target compound. After the separation, the target compound was recrystallized from ether. The crystals obtained were subjected to FAB mass analysis, whereby it was confirmed that (molecular weight)+1=303, and that the crystals obtained were the target intermediate a (yield 52.8 g (175 mmol), 71%).

Synthesis from the Intermediates a and b

The intermediate a of 13.59 g (45 mmol) was reacted with 3.86 g (7.5 mmol) of triphenylphosphine oxide serving as the intermediate b, in 75 ml of DMSO serving as a solvent at 100° C. in the presence of 338 mg (1.5 mmol) of Pd(OAc)$_2$, 927 mg (2.25 mmol) of dppp, 13.5 ml of edpa. The target compound was extracted with distilled water/chloroform from the solution and concentrated. The remaining viscous liquid was dissolved in a small amount of chloroform, and the resulting solution was subjected to column chromatography that used silica gel as a filler, to separate the target compound. After the separation, the target compound was recrystallized from methanol/toluene to obtain a white crystal. The crystals obtained were subjected to FAB mass analysis, whereby it was confirmed that (molecular weight)=1179, and that the crystals obtained were the target TPPO-(DNPO)Burst (yield 6.03 g (5.11 mmol), 68%).

56

EXAMPLE 13

Synthesis of 1,3,5-tris(diphenylphosphinyl)benzene [referred to as TDPPOB]

TDPPOB was synthesized from 1,3,5-tribromobenzene (reactant 1a) and diphenylphosphine oxide (intermediate 1), as shown in the following reaction scheme.

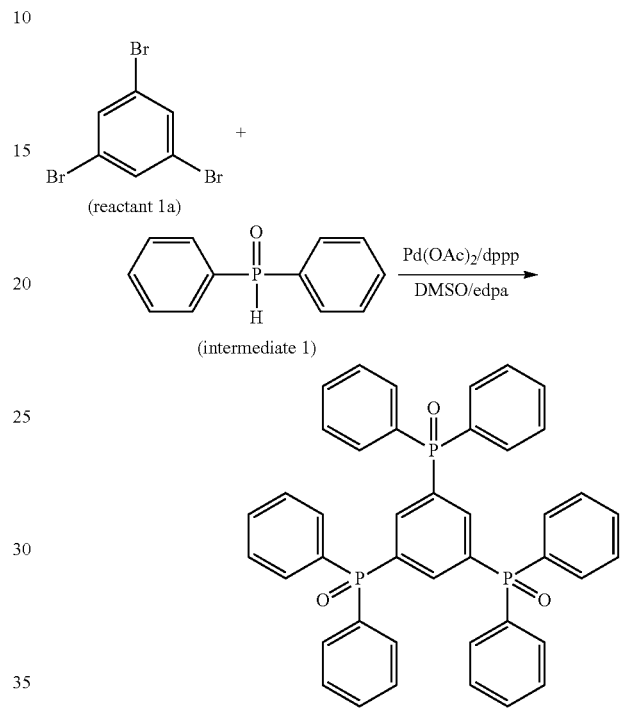

Commercially available 1,3,5-Tribromobenzene (reactant 1a) of 0.63 g (2 mmol) was reacted with 1.21 g (6.0 mmol) of diphenylphosphine oxide (intermediate 1), in 20 ml of DMSO serving as a solvent at 100° C. in the presence of 93 mg (0.41 mmol) of Pd(OAc)$_2$, 3.7 ml of edpa, and 261 mg (0.63 mmol) of dppp. The target compound was extracted with chloroform/distilled water from the solution, and the chloroform phase was separated and concentrated. The remaining viscous liquid was dissolved in a small amount of chloroform, and the resulting solution was subjected to column chromatography that used silica gel as a filler, to separate the target compound. After the separation, the target compound was recrystallized, and purified by sublimation in a vacuum. The target compound obtained was subjected to FAB mass analysis, whereby it was confirmed that (molecular weight)=679, and that the crystals obtained were the target TDPPOB (product) (yield 0.64 g (0.94 mmol), 47%, Tg 79.7° C.).

EXAMPLE 14

Synthesis of tris-(dibiphenyl-phosphinyl)triphenylphosphine oxide [TRIS-(DBPPO)-TPPO-Burst]

TRIS-(DBPPO)-TPPO-Burst was synthesized as shown in the following reaction scheme. First, OBPPO (intermediate a) was synthesized, and the from the intermediate a and the intermediate b, the TRIS-(DBPPO)-TPPO-Burst was synthesized.

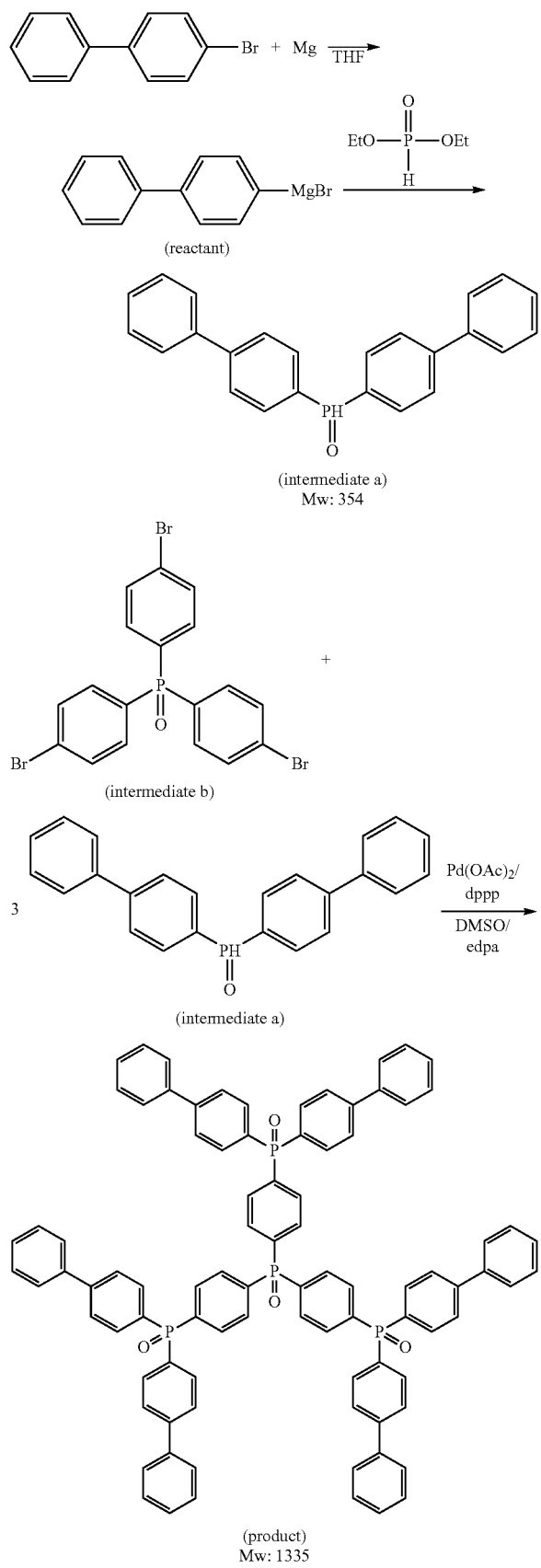

Synthesis of the Intermediate a

A solution of 100.0 g (388.5 mmol) of 4-bromobiphenyl in absolute THF was dripped onto 10.4 g (428 mmol) of a magnesium metal piece in an atmosphere of nitrogen, to prepare a Grignard reagent (reactant). To the solution, a solution of 29.5 g (213.6 mmol) of diethylphosphite in absolute THF was slowly dropwise added. After completion of the addition, the resulting solution was stirred overnight. To the solution, 40 ml of a hydrochloric acid solution (concentration 36%) was added dropwise. The target compound was extracted with distilled water/chloroform from the solution, and the chloroform phase was separated, and concentrated by a rotary evaporator. The remaining viscous liquid was dissolved in a small amount of chloroform, and the resulting solution was subjected to column chromatography that used silica gel as a filler, to separate the target compound. After the separation, the target compound was recrystallized from diethyl ether. The crystals obtained were subjected to FAB mass analysis, whereby it was confirmed that (molecular weight)+1-355, and that the crystals obtained were the target intermediate a (yield 22.73 g (64.2 mmol), 30%).

Synthesis from the Intermediates a and b

The intermediate a of 18.5 g (52.3 mmol) was reacted with 3.9 g (7.6 mmol) of triphenylphosphine oxide serving as the intermediate b, in DMSO serving as a solvent at 100 t in the presence of 250 mg (1.1 mmol) of Pd(OAc)$_2$, 460 mg (1.1 mmol) of dppp, and 7.7 ml of edpa. The target compound was extracted with distilled water/chloroform from the solution and concentrated. The remaining viscous liquid was dissolved in a small amount of chloroform, and the resulting solution was subjected to column chromatography that used silica gel as a filler, to separate the target compound. After the separation, the target compound was recrystallized from cyclohexane, to obtain a white crystal. The crystals obtained were subjected to FAB mass analysis, whereby it was confirmed that (molecular weight)=1335, and that the crystals obtained were the target TRIS-(DBPPO)-TPPO-Burst (yield 2.8 g (2.1 mmol), 28%).

EXAMPLE 15

Synthesis of bis-(dibiphenyl-phosphinyl)-biphenylene [BIS(OBPPO)-BP]

BIS(OBPPO)-BP was synthesized from OBPPO (intermediate a) and 4,4'-dibromobiphenyl, as shown in the following reaction scheme.

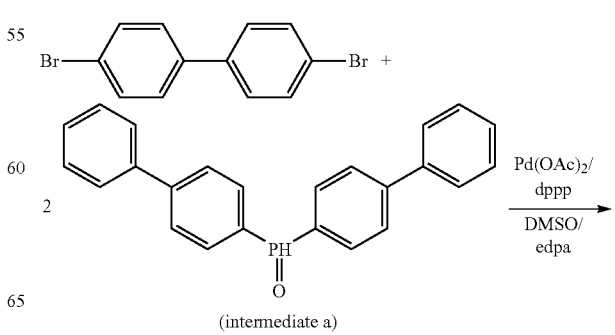

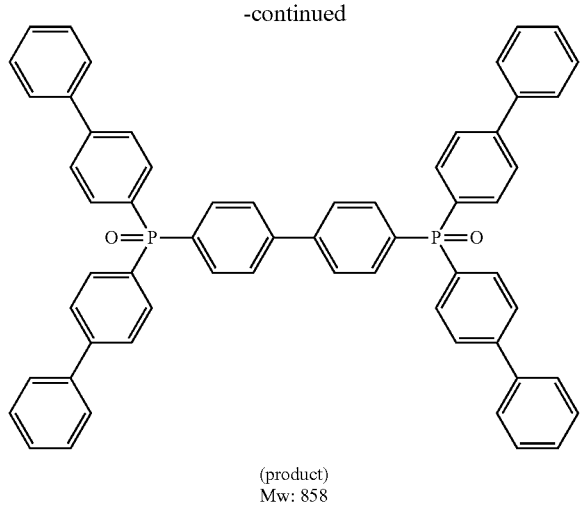

(product)
Mw: 858

Synthesis of the intermediate a and 4,4'-dibromobiphenyl

The intermediate a of 18.49 g (52.2 mmol) was reacted with 3.61 g (11.6 mmol) of 4,4'-dibromobiphenyl, in DMSO serving as a solvent at 100° C., in the presence of 250 mg (1.1 mmol) of Pd(OAc)$_2$, 460 mg (1.1 mmol) of dppp, and 7.9 ml of edpa. The target compound was extracted with distilled water/chloroform from the solution and concentrated. The remaining viscous liquid was dissolved in a small amount of chloroform, and the resulting solution was subjected to column chromatography that used silica gel as a filler, to separate the target compound. After the separation, the target compound was recrystallized. The crystals obtained were subjected to FAB mass analysis, whereby it was confirmed that (molecular weight)=858, and that the crystals obtained were the target BIS(OBPPO)-BP (yield 7.7 g (9.0 mmol), 77%).

EXAMPLE 16

Synthesis of tris-(t-butyl-diphenyl-phosphinyl)triphenylphosphine oxide[TRIS-(t-Bu-DPPO)-TPPO-Burst]

TRIS-(t-Bu-DPPO)-TPPO-Burst was synthesized as shown in the following reaction scheme. First, t-Bu-DPPO (intermediate c) was synthesized, and then from the intermediate c and the intermediate b, the TRIS-(t-Bu-DPPO)-TPPO-Burst was synthesized.

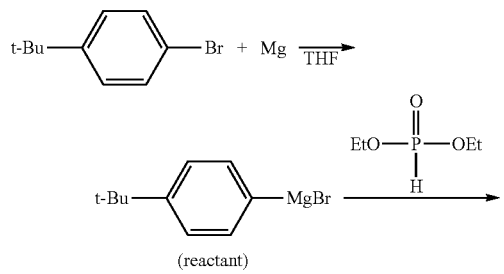

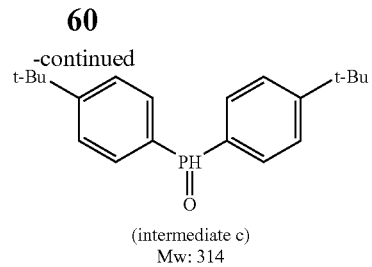

(intermediate c)
Mw: 314

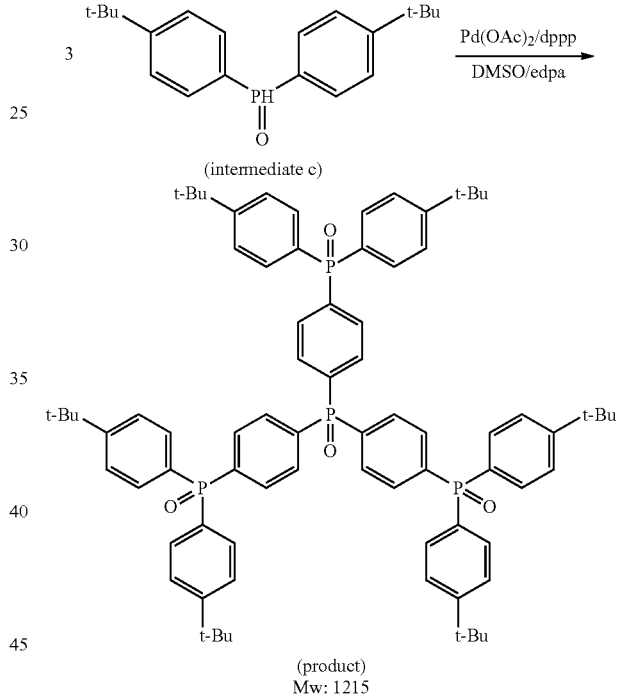

(product)
Mw: 1215

Synthesis of the Intermediate c

A solution of 25.0 g (117.3 mmol) of 4-t-butyl-bromobenzene in absolute THF was dripped onto 2.85 g (117.3 mmol) of a magnesium metal piece in an atmosphere of nitrogen, to prepare a Grignard reagent (reactant). To the solution, a solution of 8.10 g (58.66 mmol) of diethylphosphite in absolute THF was slowly dropwise added. After completion of the addition, the resulting solution was stirred overnight. To the solution, 30 ml of a hydrochloric acid solution (concentration 36%) was added dropwise. The target compound was extracted with distilled water/chloroform from the solution, and the chloroform phase was separated, and concentrated by a rotary evaporator. The remaining viscous liquid was dissolved in a small amount of chloroform, and the resulting solution was subjected to column chromatography that used silica gel as a filler, to separate the target compound. After the separation, the target compound was recrystallized from diethyl ether. The crystals obtained were subjected to FAB mass analysis, whereby it was confirmed that (molecular weight)+1=315, and that the crystals obtained were the target intermediate c (yield 8.65 g (18.4 mmol), 47%).

Synthesis from the Intermediates c and b

The intermediate c of 15.5 g (49.4 mmol) was reacted with 4.2 g (8.2 mmol) of triphenylphosphine oxide serving as the intermediate b, in DMSO serving as a solvent at 100° C. in the presence of 270 mg (1.2 mmol) of Pd(OAc)$_2$, 510 mg (1.2 mmol) of dppp, and 8.4 ml of edpa. The target compound was extracted with distilled water/chloroform from the solution and concentrated. The remaining viscous liquid was dissolved in a small amount of chloroform, and the resulting solution was subjected to column chromatography that used silica gel as a filler, to separate the target compound. After the separation, the target compound was recrystallized from toluene-chloroform, to obtain a, white crystal. The crystals obtained were subjected to FAB mass analysis, whereby it was confirmed that (molecular weight)=1215 and that the crystals obtained were the target TRIS-(t-Bu-DPPO)-TPPO-Burst (yield 1.5 g (1.2 mmol), 15%).

EXAMPLE 17

Synthesis of 4,4'-bis(diphenylphosphinyl)-biphenyl [TPPO-Dimer]

TPPO-Dimer was synthesized as shown in the following reaction scheme. First, diphenylphosphine oxide as an intermediate 1 was synthesized, and then from the intermediate 1, the TPPO-Dimer was synthesized.

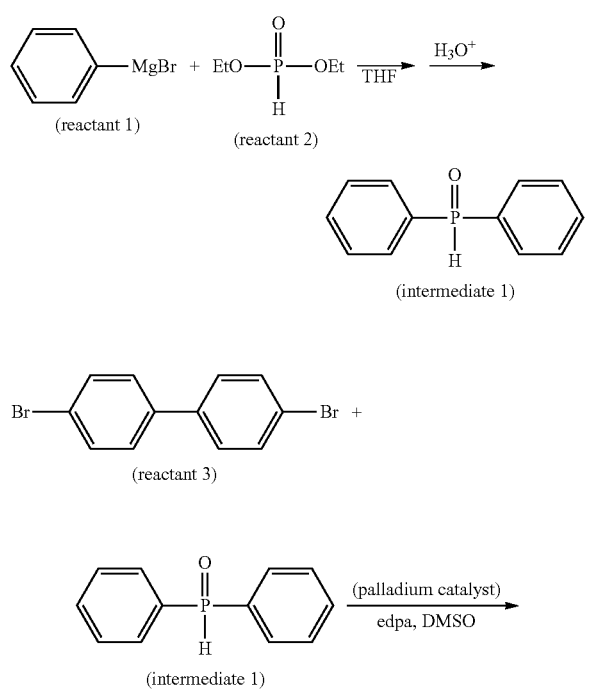

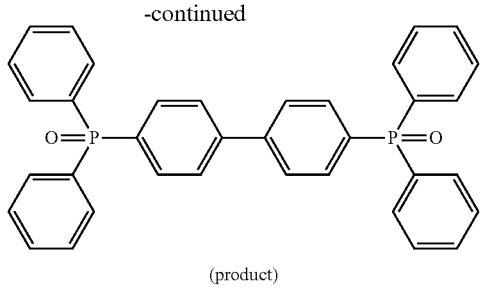

(product)

Synthesis of the Intermediate 1

A solution of 17.2 g (110 mmol) of bromobenzene in absolute THF was dripped onto 2.4 g (98.8 mmol) of a magnesium metal piece in an atmosphere of nitrogen while cooling the solution to prevent reflux of the solvent, to prepare a Grignard reagent (reactant 1). To the solution, 5.18 g (37.5 mmol) of diethylphosphite (reactant 2) in absolute THF was slowly dropwise added. After completion of the addition, the resulting solution was stirred overnight. To the solution, 1 mol/l hydrochloric acid was added dropwise. The target compound was extracted with distilled water/chloroform from the solution, and the chloroform phase was separated, and concentrated by a rotary evaporator. The remaining viscous liquid was dissolved in a small amount of chloroform, and the resulting solution was subjected to column chromatography that used silica gel as a filler, to separate the target compound. After the separation, the target compound was recrystallized from diethyl ether. The crystals obtained were subjected to FAB mass analysis, whereby it was confirmed that (molecular weight)+1=203 and that the crystals obtained were the target intermediate 1 (yield 3.57 g (17.7 mmol), 47%).

Synthesis from the Intermediate 1

The intermediate 1 of 4.04 g (20 mmol) was reacted with 3.12 g (10 mmol) of commercially available 4,4'-dibromobiphenyl (reactant 3), in DMSO serving as a solvent at 100° C. in the presence of 89.8 mg (0.4 mmol) of Pd(OAc)$_2$, 247 mg (0.6 mmol) of dppp, and 9 ml of edpa. The target compound was extracted with chloroform/distilled water from the solution, and the chloroform phase was separated and concentrated. The remaining viscous liquid was dissolved in a small amount of chloroform, and the resulting solution was subjected to column chromatography that used silica gel as a filler, to separate the target compound. After the separation, the target compound was recrystallized, and purified by sublimation in a vacuum. The target compound obtained was subjected to FAB mass analysis, whereby it was confirmed that (molecular weight)=555, and that the crystals obtained were the target TPPO-Dimer (product) (yield 4.56 g (8.22 mmol), 82%)

EXAMPLE 18

Synthesis of [4,4'-bis[1-naphthyl)-phenyl-phosphinyl]]-biphenyl[α-NPPOB]

α-NPPOB was synthesized as shown in the following reaction scheme. First, (1-naphthyl)-phenyl-phosphine oxide (intermediate 1d) was synthesized, and then from the intermediate 1d, the α-NPPOB was synthesized.

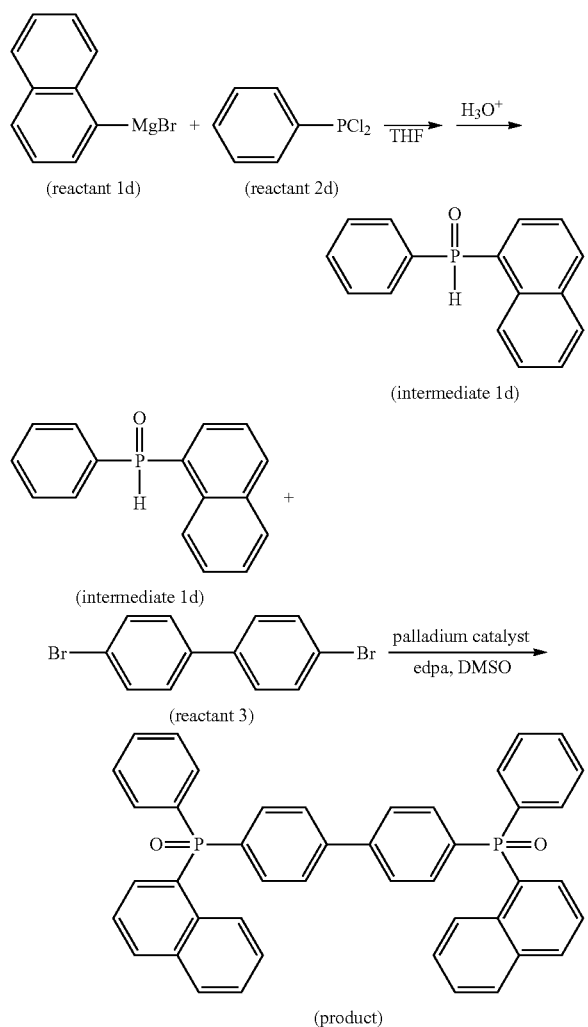

Synthesis of the Intermediate 1d

A solution of 28.35 g (137 mmol) of 1-bromonaphthalene in absolute THF was dripped onto 3.15 g (129.6 mmol) of a magnesium metal piece in an atmosphere of nitrogen, to prepare a Grignard reagent (reactant 1d). The solution was slowly dropwise added to a solution of 26.0 g (145 mmol) of dichlorophenylphosphine (reactant 2d) in absolute THF. After completion of the addition, the resulting solution was stirred overnight To the solution, 21 ml of a hydrochloric acid solution (concentration 36%) was added dropwise. The target compound was extracted with distilled water/chloroform from the solution, and the chloroform phase was separated, and concentrated by a rotary evaporator. The remaining viscous liquid was dissolved in a small amount of chloroform, and the resulting solution was subjected to column chromatography that used silica gel as a filler, to separate the target compound. After the separation, the target compound was recrystallized from cyclohexane. The crystals obtained were subjected to FAB mass analysis, whereby it was confirmed that (molecular weight)+1=253, and that the crystals obtained were the target intermediate 1d (yield 12.7 g (50.3 mmol), 36%).

Synthesis from the Intermediate 1d

The intermediate 1 of 5.04 g (20 mmol) was reacted with 3.12 g (10 mmol) of commercially available 4,4'-dibromobiphenyl (reactant 3), in DMSO serving as a solvent at 100° C. in the presence of 89.8 mg (0.4 mmol) of Pd(OAc)$_2$, 247 mg (0.6 mmol) of dppp, and 9 ml of edpa. The target compound was extracted with chloroform/distilled water from the solution, and the chloroform phase was separated and concentrated. The remaining viscous liquid was dissolved in a small amount of chloroform, and the resulting solution was subjected to column chromatography that used silica gel as a filler, to separate the target compound. After the separation, the target compound was recrystallized, and purified by sublimation in a vacuum. The target compound obtained was subjected to FAB mass analysis, whereby it was confirmed that (molecular weight)=655, and that the crystals obtained were the target α-NPPOB (product) (yield 5.15 g (7.87 mmol), 79%).

EXAMPLE 19

The TPPO-Dimer prepared in Example 17 was evaluated.
[Properties of the TPPO-Dimer]
(Ionization Potential and Band Gap)

The ionization potential of the TPPO-Dimer obtained was measured by an ultraviolet-ray electron spectrometer (AC-2) manufactured by RIKENKEIKI Co., Ltd. and found to be beyond 6.8 eV because the threshold was not detected up to the measurement limit of 6.8 eV. The band gap was 4.07 eV. Thus, it was noted that the TPPO-Dimer had a higher ionization potential and a larger band gap than the ionization potential and band gap of bathocuproin which was in general use as an electron-transporting material, as an hole-blocking material and as an exciton-confining material (the ionization potential of bathocuproin: 6.8 eV, the band gap thereof: 3.7 eV). This indicates that TPPO-Dimer has a high capability to block holes and a great effect of confining excitons and is promising as a hole-blocking material and as an exciton-confining material for a phosphorescent element.
(Glass Transition Temperature)

The Tg of the TPPO-Dimer was measured by DSC-6200 manufactured by Seiko Instruments & Electronics Ltd. according to differential thermal analysis, and found to be as high as 90.8° C. The Tg of 90.8° C. is higher than the Tg (63° C.) of N,N'-bis(3-methylphenyl)-N,N'-bis(phenyl)-benzidine (TPD) which is in general use as a hole-transporting material. This indicates that TPPO-Dimer has excellent heat resistance.
[Manufacture of an Organic Electroluminescent Element Using TPPO-Dimer]

An organic electroluminescent element was manufactured using TPPO-Dimer as an electron-transporting material. The following are details of the constitution of the element.

transparent electrode (ITO)/hole-transporting layer (TPD)/luminescent layer (Alq$_3$)/electron-transporting layer (TPPO-Dimer)/cathode(MgAg)

More specifically, TPD was vacuum-deposited on a glass substrate having a transparent electrode (100 nm) of ITO, to form a hole-transporting layer thereon. The degree of vacuum was 2.0×10$^{-4}$ Pa (ditto with Example 20 and later Examples), and the thickness of the hole-transporting layer was 55 nm. On the hole-transporting layer, Alga was deposited to form a luminescent layer having a thickness of 20 nm. The deposition speed was 0.2 nm/sec. On the luminescent layer, TPPO-Dimer was deposited to form an electron-transporting layer having a thickness of 30 nm. On the electron-transporting layer, Mg and Ag were deposited to a thickness of 100 nm to form a cathode.

COMPARATIVE EXAMPLE 4

An element according to Comparative Example 4 was manufactured in the same manner as in Example 19, except that TPPO-Dimer was not employed as the electron-transporting material and that the luminescent layer (Alq$_3$) formed had a thickness of 50 nm.
[Luminance-voltage Characteristics of the Organic Electroluminescent Elements]

A voltage was applied to each of the elements according to Example 19 and Comparative Example 4, to evaluate their luminance-voltage characteristics.

Figure 13:
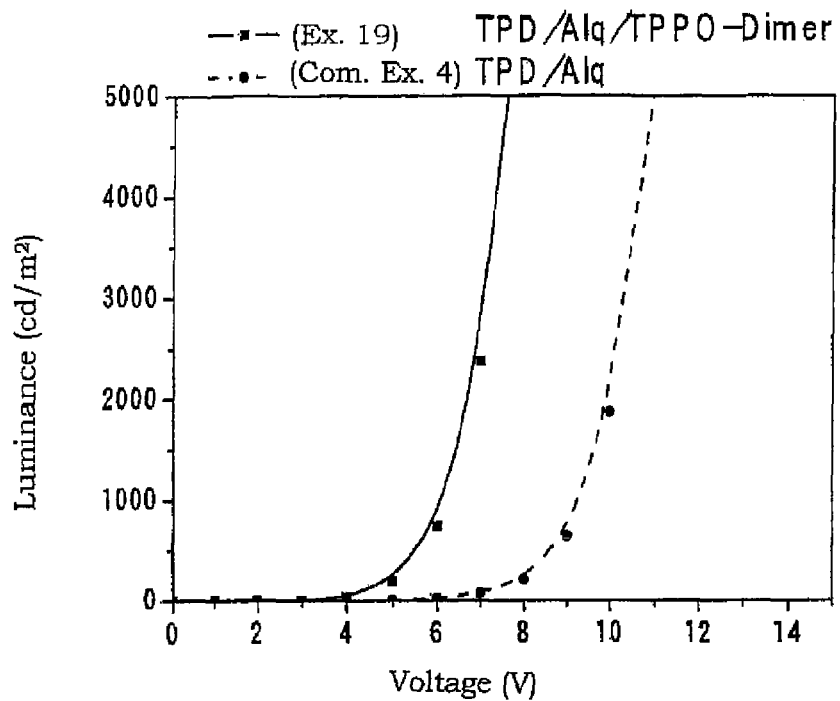
FIG. 13 is a characteristic view showing the luminance-voltage relationships of the elements according to Example 19 and Comparative Example 4.

FIG. 13 is a characteristic view showing the luminance-voltage relationships of the elements according to Example 19 and Comparative Example 4.

As seen in FIG. 13, the element according to Example 19 emitted light at a lower voltage than the element according to Comparative Example 4. This indicates that TPPO-Dimer has a high capability to transport electrons.

EXAMPLE 20

The characteristics of the TDPPOB prepared in Example 13 were evaluated.
[Properties of the TDPPOB]
(Ionization Potential and Band Gap)

The ionization potential of the TDPPOB was measured by an ultraviolet-ray electron spectrometer (AC-2) manufactured by RIKENKEIKI Co., Ltd. and found to be beyond 6.8 eV because the threshold was not detected up to the measurement limit of 6.8 eV. The band gap was 3.98 eV. Thus, it was noted that the TDPPOB had a higher ionization potential and a larger band gap than the ionization potential and band gap of bathocuproin which was in general use as an electron-transporting material, as an hole-blocking material and as an exciton-confining material (the ionization potential of bathocuproin: 6.8 eV, the band gap thereof: 3.7 eV). This indicates that TDPPOB has a high capability to block holes and a great effect of confining excitons and is promising as a hole-blocking material and as an exciton-confining material for a phosphorescent element.
(Glass Transition Temperature)

The Tg of the TDPPOB obtained was measured by DSC-6200 manufactured by Seiko Instruments & Electronics Ltd. according to differential thermal analysis, and found to be as high as 79.7° C. The Tg of 79.7° C. is higher than the Tg (63 t) of TPD which is in general use as a hole-transporting material. This indicates that TDPPOB has excellent heat resistance.
[Manufacture of an Organic Electroluminescent Element Using TDPPOB]

An organic electroluminescent element was manufactured using TDPPOB as an electron-transporting material. The following are details of the constitution of the element.
    transparent electrode (ITO)/hole-transporting layer (TPD)/luminescent layer (Alq$_3$)/electron-transporting layer (TDPPOB)/cathode (MgAg)

More specifically, the element was manufactured in the same manner as used to obtain the element according to Example 19, except that the TDPPOB was used as the electron-transporting material (thickness 30 nm).

[Luminance-voltage Charactertistic of the Organic Electroluminescent Element]

Figure 14:
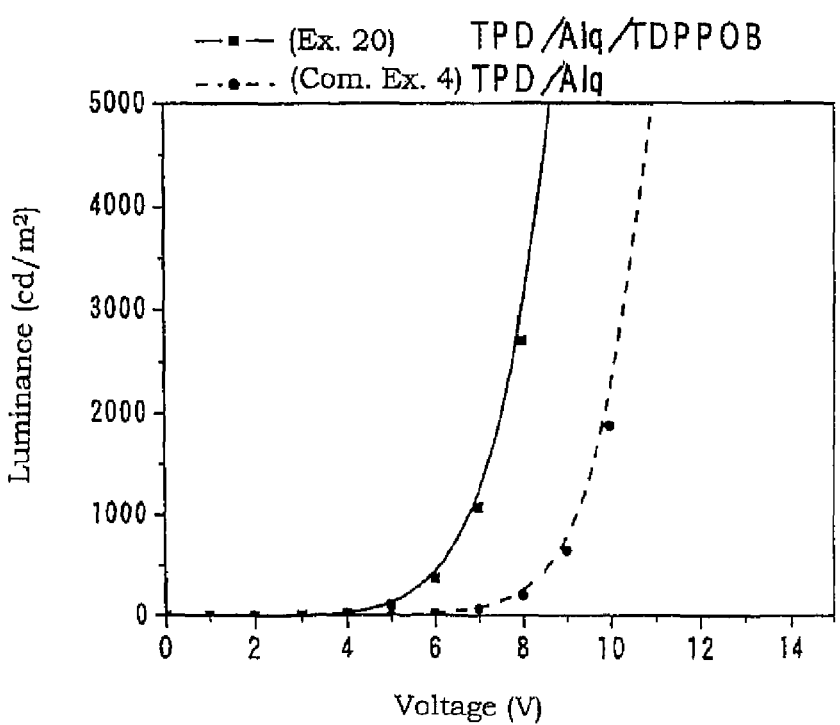
FIG. 14 is a characteristic view showing the luminance-voltage relationships of the elements according to Example 20 and Comparative Example 4.

A voltage was applied to the organic electroluminescent element according to Example 20, to evaluate its luminance-voltage characteristic. FIG. 14 is a characteristic view showing the luminance-voltage relationship of the element according to Example 20, together with the above-mentioned luminance-voltage relationship of the element according to Comparative Example 4.

As seen in FIG. 14, the element according to Example 20 emitted light at a lower voltage than the element according to Comparative Example 4. This indicates that TDPPOB has a high capability to transport electrons.

EXAMPLE 21

The characteristics of the TPPO-Trimer prepared in Example 4 were evaluated.
[Properties of the TPPO-Trimer]
(Ionization Potential and Band Gap)

The ionization potential of the TPPO-Trimer was measured by an ultraviolet-ray electron spectrometer (AC-2) manufactured by RIKENKEIKI Co., Ltd. and found to be beyond 6.8 eV because the threshold was not detected up to the measurement limit of 6.8 eV. The band gap was 4.02 eV. Thus, it was noted that the TPPO-Trimer had a higher ionization potential and a larger band gap than the ionization potential and band gap of bathocuproin which was in general use as an electron-transporting material, as an hole-blocking material and as an exciton-confining material (the ionization potential of bathocuproin: 6.8 eV, the band gap thereof: 3.7 eV). This indicates that the TPPO-Trimer has a high capability to block holes and a great effect of confining excitons and is promising as a hole-blocking material and as an exciton-confining material for a phosphorescent element.
(Glass Transition Temperature)

The Tg of the TPPO-Trimer obtained was measured by DSC-6200 manufactured by Seiko Instruments & Electronics Ltd. according to differential thermal analysis, and found to be as high as 105° C. The Tg of 105° C. is higher than the Tg (63° C.) of TPD (N,N'-bis(3-methylphenyl)-N,N'-bis(phenyl)-benzidine) which is in general use as a hole-transporting material. This indicates that TPPO-Trimer has excellent heat resistance.
[Manufacture of an Organic Electroluminescent Element Using TPPO-Trimer]

An organic electroluminescent element was manufactured using TPPO-Trimer as an electron-transporting material. The following are details of the constitution of the element.
    transparent electrode (ITO)/hole-transporting layer(TPD)/luminescent layer(Alq$_3$)/electron-transporting layer (TPPO-Dimer)/cathode (MgAg)

More specifically, the element was manufactured in the same manner as used to obtain the element according to Example 19, except that the TPPO-Trimer was used as the electron-transporting material to form the electron-transporting layer (thickness 30 nm).
[Luminance-voltage Charactertistic of the Organic Electroluminescent Element]

Figure 15:
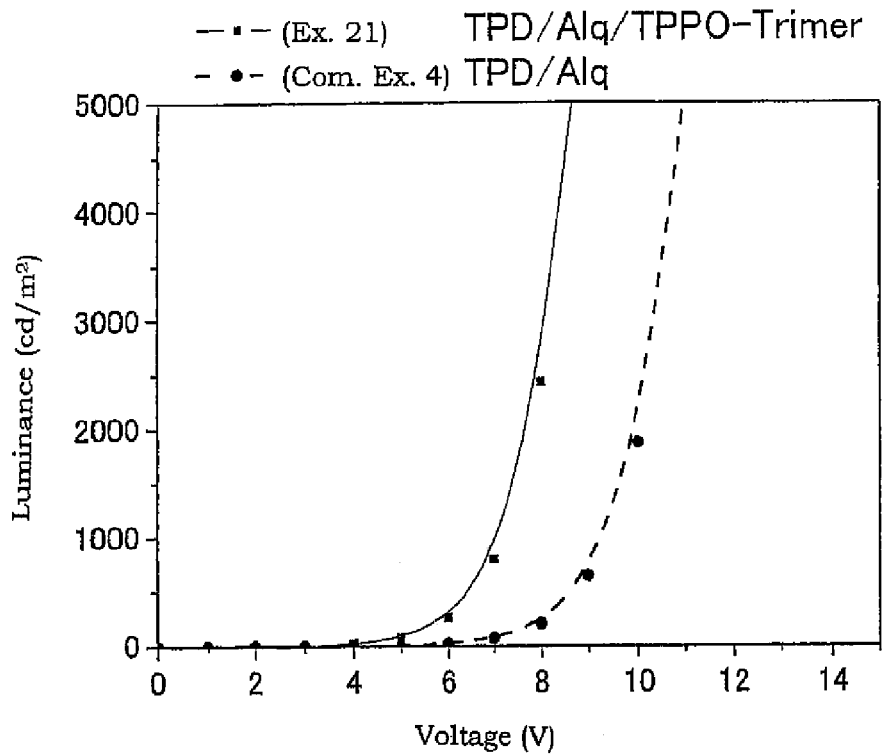
FIG. 15 is a characteristic view showing the luminance-voltage relationships of the elements according to Example 21 and Comparative Example 4.

A voltage was applied to the element according to Example 21, to evaluate its luminance-voltage characteristic. FIG. 15 is a characteristic view showing the luminance-voltage relationship of the element according to Example 21, together with the above-mentioned luminance-voltage relationship of the element according to Comparative Example 4.

As seen in FIG. 15, the element according to Example 21 emitted light at a lower voltage than the element according to Comparative Example 4. This indicates that TPPO-Trimer has a high capability to transport electrons.

EXAMPLE 22

The characteristics of the α-NPPOB prepared in Example 18 were evaluated.
[Characteristics of the α-NPPOB]
(Ionization Potential and Band Gap)

The ionization potential of the α-NPPOB obtained was measured by an ultraviolet-ray electron spectrometer (AC-2) manufactured by RIKENKEIKI Co., Ltd. and found to be beyond 6.8 eV because the threshold was not detected up to the measurement limit of 6.8 eV. The band gap was 3.92 eV. Thus, it was noted that the α-NPPOB had a higher ionization potential and a larger band gap than the ionization potential and band gap of bathocuproin which was in general use as an electron-transporting material, as an hole-blocking material and as an exciton-confining material (the ionization potential of bathocuproin: 6.8 eV, the band gap thereof: 3.7 eV). This indicates that α-NPPOB has a high capability to block holes and a great effect of confining excitons and is promising as a hole-blocking material and as an exciton-confining material for a phosphorescent element.
(Glass Transition Temperature)

The Tg of the α-NPPOB obtained was measured by DSC-6200 manufactured by Seiko Instruments & Electronics Ltd. according to differential thermal analysis, and found to be as high as 125° C. The Tg of 125° C. is higher than the Tg (63° C.) of TPD (N,N'-bis(3-methylphenyl)-N,N'-bis(phenyl)-benzidine) which is in general use as a hole-transporting material. This indicates that α-NPPOB has excellent heat resistance.
[Manufacture of an Organic Electroluminescent Element Using α-NPPOB]

An organic electroluminescent element was manufactured using NPPOB as an electron-transporting material. The following are details of the constitution of the element.

transparent electrode (ITO)/hole-transporting layer (TPD)/luminescent layer ($Alq_3$)/electron-transporting layer (α-NPPOB)/cathode (MgAg)

More specifically, the element was manufactured in the same manner as used to obtain the element according to Example 19, except that the α-NPPOB was used as the electron-transporting material to form an electron-transporting layer (thickness 30 nm).
[Luminance-voltage Characteristic of the Organic Electroluminescent Element]

Figure 16:
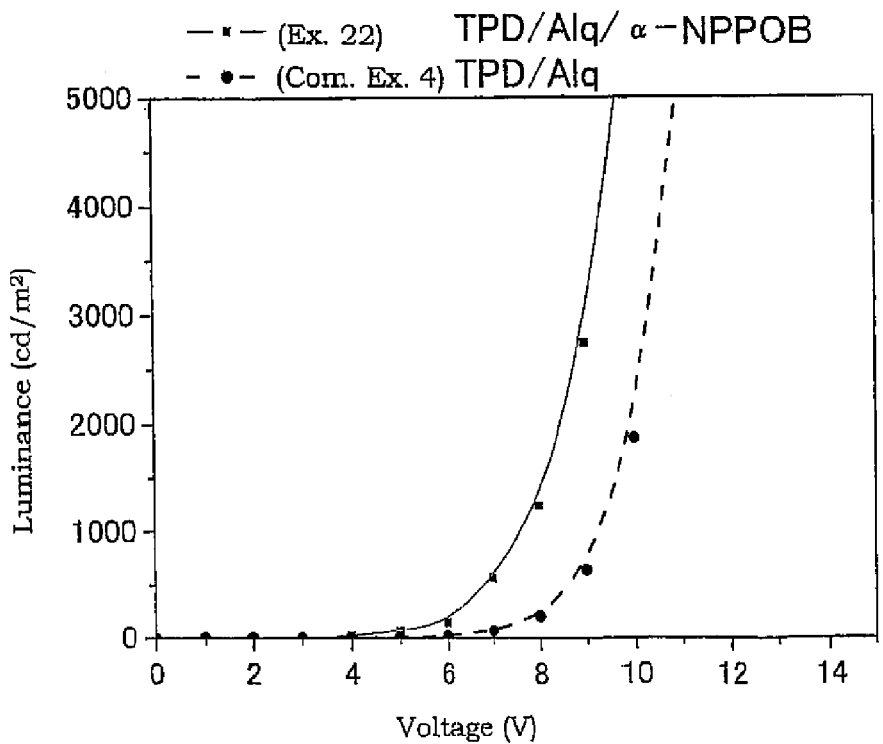
FIG. 16 is a characteristic view showing the luminance-voltage relationships of the elements according to Example 22 and Comparative Example 4.

A voltage was applied to the element according to Example 22, to evaluate its luminance-voltage characteristic. FIG. 16 is a characteristic view showing the luminance-voltage relationship of the element according to Example 22, together with the above-mentioned luminance-voltage relationship of the element according to Comparative Example 4.

As seen in FIG. 16, the element according to Example 22 emitted light at a lower voltage than the element according to Comparative Example 4. This indicates that α-NPPOB has a high capability to transport electrons.

The invention claimed is:

1. A manufacturing method of an organic electroluminescent element including an anode, a cathode and a plurality of organic compound layers sandwiched between the anode and cathode, the process comprising the steps of:

forming a hole-transporting layer using an organic compound insoluble in alcohols; and forming an electron-transporting layer directly on the hole-transporting layer by a wet method using as an electron transporting layer material a phosphorus-containing organic compound dissolved in an alcohol;

wherein the phosphorus-containing organic compound is represented by the general formula (1):

wherein $Ar^1$-$Ar^3$, the same or different from each other, represent an aromatic ring residue optionally containing a substituent.

2. The manufacturing method of an organic electroluminescent element according to claim 1, wherein the alcohol is a linear or branched $C_1$-$C_6$ aliphatic alcohol.

3. The manufacturing method of claim 1, wherein the atomic ring residue is:

a monocyclic aromatic ring or heterocycle chosen from a benzene ring, a thiophene ring, a triazine ring, a furan ring, a pyrazine ring or a pyridine ring;

a condensed polycyclic aromatic ring or heterocycle chosen from a naphthalene ring, an anthracene ring, a thieno[3,2-b]thiophene ring, a phenanthrene ring, a fluorene ring or a furo[3,2-b]furan ring;

a ring-aggregated aromatic ring or heterocycle chosen from a biphenyl ring, a terphenyl ring, a bithiophene ring or a bifuran ring; and an aromatic ring or heterocycle chosen from a acridine ring, an isoquinoline ring, an indole ring, a carbazole ring, a carboline ring, a quinoline ring, a dibenzofuran furan ring, a cinnoline ring, a thionaphthene ring, a 1,10-phenanthroline ring, a phenothiazine ring, a purine ring, a benzofuran ring or a silol ring.

4. The method of claim 1, wherein $Ar^1$-$Ar^3$ are independently optionally substituted by one or more of an alkyl group, an alkoxy group, a halogen atom, cyano group, nitro group, amino group, an aryl group and a diarylphosphinyl group.

5. The method of claim 3, wherein the atomic ring residue is independently optionally substituted by one or more of an alkyl group, an alkoxy group, a halogen atom, cyano group, nitro group, amino group, an aryl group and a diarylphosphinyl group.

6. A manufacturing method of an organic electroluminescent element including an anode, a cathode and a plurality of organic compound layers sandwiched between the anode and cathode, the process comprising the steps of:

forming a hole-transporting layer using an organic compound insoluble in alcohols; and forming an electron-transporting layer directly on the hole-transporting layer by a wet method using as an electron transporting layer material a phosphorus-containing organic compound dissolved in an alcohol;

wherein the phosphorus-containing organic compound is represented by the general formula (2):

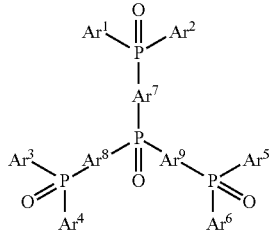
(2)

wherein $Ar^1$-$Ar^6$, the same or different from each other, represent an aromatic ring residue optionally containing a substituent; and $Ar^7$-$Ar^9$, the same or different from each other, represent an arylene group optionally containing a substituent.

7. The manufacturing method of an organic electroluminescent element according to claim 6, wherein the alcohol is a linear or branched $C_1$-$C_6$ aliphatic alcohol.

8. A manufacturing method of an organic electroluminescent element including an anode, a cathode and a plurality of organic compound layers sandwiched between the anode and cathode, the process comprising the steps of:

forming a hole-transporting layer using an organic compound insoluble in alcohols; and forming an electron-transporting layer directly on the hole-transporting layer by a wet method using as an electron transporting layer material a phosphorus-containing organic compound dissolved in an alcohol;

wherein the phosphorus-containing organic compound is represented by the general formula (3):

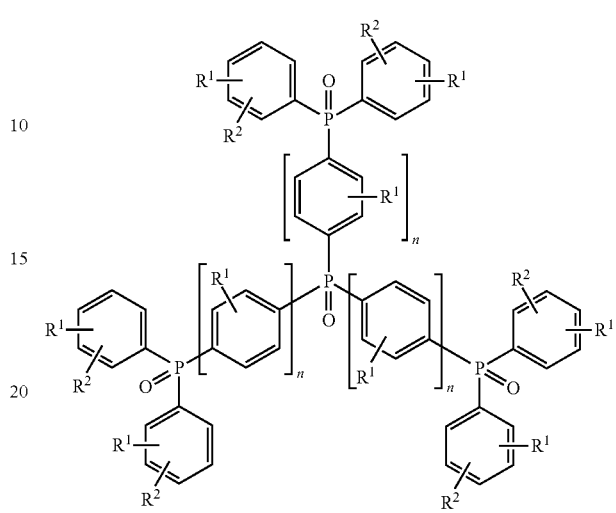
(3)

wherein $R^1$ or $R^2$, the same or different from each other, represents a hydrogen atom, an alkyl group, a halogen atom, cyano group, nitro group, amino group, an aryl group or a diarylphosphinyl group, and $R^1$ and $R^2$ can form, together with a carbon atom of a benzene ring to which they are linked, a substituted or unsubstituted aromatic ring; and n is 1 or 2.

9. The manufacturing method of an organic electroluminescent element according to claim 8, wherein the alcohol is a linear or branched $C_1$-$C_6$ aliphatic alcohol.

* * * * *